United States Patent
Yoon et al.

(10) Patent No.: US 7,179,807 B2
(45) Date of Patent: Feb. 20, 2007

(54) 5-SUBSTITUTED-2-ARYLPYRAZINES

(75) Inventors: Taeyoung Yoon, Guilford, CT (US); Ping Ge, Durham, CT (US); Stéphane De Lombaert, Madison, CT (US); Raymond F. Horvath, Guilford, CT (US); Dario Doller, Wallingford, CT (US); Kevin J. Hodgetts, Kilingworth, CT (US); Lu Yan Zhang, Branford, CT (US); Bernd Kaiser, Wallingford, CT (US); Xuechun Zhang, Branford, CT (US); Yasuchika Yamaguchi, Guilford, CT (US); Cunyu Zhang, Morrisville, NC (US); Jim Darrow, Wallingford, CT (US)

(73) Assignee: Neurogen Corporation, Branford, CT (US)

( * ) Notice: Subject to any disclaimer, the term of this patent is extended or adjusted under 35 U.S.C. 154(b) by 354 days.

(21) Appl. No.: 10/645,312

(22) Filed: Aug. 20, 2003

(65) Prior Publication Data

US 2004/0106620 A1    Jun. 3, 2004

Related U.S. Application Data

(60) Provisional application No. 60/405,013, filed on Aug. 20, 2002.

(51) Int. Cl.
| | |
|---|---|
| A61K 31/535 | (2006.01) |
| A61K 31/497 | (2006.01) |
| A61K 31/4965 | (2006.01) |
| C07D 413/00 | (2006.01) |
| C07D 403/00 | (2006.01) |

(52) U.S. Cl. .............. 514/235.8; 514/252.11; 514/255.05; 514/255.06; 544/120; 544/295; 544/405; 544/408

(58) Field of Classification Search ............ None
See application file for complete search history.

(56) References Cited

U.S. PATENT DOCUMENTS

| | | | |
|---|---|---|---|
| 4,083,977 A | 4/1978 | Miesel | 424/250 |
| 4,160,834 A | 7/1979 | Miesel | 424/250 |
| 4,211,870 A | 7/1980 | Barnett et al. | 544/336 |
| 4,293,552 A | 10/1981 | Miesel | 424/250 |
| 4,788,197 A | 11/1988 | Wakabayashi et al. | 514/255 |
| 2003/0018035 A1 | 1/2003 | Yoon et al. | |
| 2005/0215559 A1 | 9/2003 | Yoon et al. | |

FOREIGN PATENT DOCUMENTS

| | | |
|---|---|---|
| DE | 1 499 768 | 2/1978 |
| DE | 2 272 216 A | 5/1994 |
| JP | 3048666 | 3/1991 |
| JP | 10-77286 | 3/1998 |
| WO | WO-95/10506 | 4/1995 |
| WO | WO-99/38829 | 1/1998 |
| WO | WO-98/11075 | 3/1998 |
| WO | WO 98/38174 | 9/1998 |
| WO | WO 98/43641 | 10/1998 |
| WO | WO 00/12488 | 3/2000 |
| WO | WO 00/45800 | 8/2000 |
| WO | WO 01/60806 A2 | 8/2001 |

OTHER PUBLICATIONS

Dautzenberg and Hauger, "The CRF peptide family and their receptors: yet more partners discovered" Trends in Phamacological Sciences, vol. 23(2), pp. 71-77 (Feb. 2002).*

Kehne and De Lombaert, "Non-Peptide CRF1 Receptor Antagonists for the Treatment of Anxiety, Depression and Stress Disorders" Current Drug Targets—CNS & Neurological Disorders, vol. 1(5), pp. 467-493 (2002).*

Akita et al., "Cross-coupling Reaction of Chloropyrazines with Acetylenes," Chem. Pharm. Bull. 34:1447-1458 (1986).

(Continued)

Primary Examiner—James O. Wilson
Assistant Examiner—Zachary C. Tucker
(74) Attorney, Agent, or Firm—Peter F. Corless; Dwight D. Kim; Edwards, Angell, Palmer & Dodge, LLP

(57) ABSTRACT

Novel 5-substituted-2-arylpyrazine compounds are provided. Such compounds can act as selective modulators or CRF receptors. Compounds of the invention are provided by the following formula:

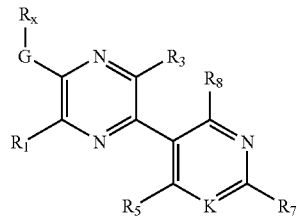

The 5-substituted-2-arylpyrazine compounds provided herein are useful in the treatment of a number of CNS and periphercal disorders, particularly stress, anxiety, depression, cardiovascular disorders, and eating disorders. Methods of treatment of such disorders and well as packaged pharmaceutical compositions are also provided.

Compounds provided are also useful as probes for the localization of CRF receptors and as standards in assays for CRF receptor binding. Methods of using the compounds in receptor localization studies are given.

15 Claims, No Drawings

OTHER PUBLICATIONS

Alvernhe et al., "Action De L'Acide Fluorhydrique Sur Les Azirines: Synthase D'a-Fluoroacetines et de Difluoroamines—Etude de L'Orientation de la Reaction," Tetrahedron Letters 21:1437-1440 (1980).

Badiger et al., "Oxidative Cyclization Using Fetizone's Reagent," Indian J. Chem. 16B:71-75 (1978).

Benincori et al., "Studies on the Fischer Indole Synthesis: Rearrangements of Five-, Six- and Seven-membered Cyclic Hydrazones of Pyrazoline, Tetrahydropyridazine and Tetrahydro-1,2-diazepine Series in Polyphosphoric Acid," J. Chem. Soc. Perkin Trans. 1:2139-2145 (1991).

Bremmer et al., "Elevated CSF Corticotropin-Releasing Factor Concentrations in Posttraumatic Stress Disorder," Am. J. Psychiatry 154:624-629 (1997).

Chellappa et al., "PMR Spectra of Some Substituted Pyrazines & 2,3-Dihydropyrazines," Indian Journal of Chemistry 21B:778-779 (1982).

Hamazaki et al., "The Photoreaction of 5-Aryl-2, 3-dicyanopyrazine in the Presence of Diethylamine," Bulletin of Science and Engineering Research Laboratory Waseda University 103:35-38 (1983).

Heinrichs et al., "Anti-Stress Action of a Corticotropin-Releasing Factor Antagonist on Behavioral Reactivity to Stressors of Varying Type and Intensity," Neuropsychopharmacology 11:179-186 (1994).

Iredale et al., "Differential Regulation of Corticotropin-Releasing Factor$_1$ Receptor Expression by Stress and Agonist Treatments in Brain and Cultured Cells," Molecular Pharmacology 50:1103-1110 (1996).

Kalin et al., "Restraint stress increases corticotropin-releasing hormone mRNA content in the amygdala and paraventricular nucleus," Brain Research 656:182-186 (1994).

Menzaghi et al., "Characterization of a Novel and Potent Corticotropin-Releasing Factor Antagonist in Rats[1]," Journal of Pharmacology and Experimental Therapeutics 269:564572 (1994).

Mitchell et al., "The Role of Corticotropin Releasing Factor in Depressive Illness: A Critical Review," Neuroscience and Behavioral Reviews 22:635-651 (1998).

Ohta et al., "Anti-Platelet Aggregation Activity of Some Pyrazines," Biol. Pharm. Bull 20:1076-1081 (1997).

Ohta et al., "Coupling Reaction of Chloropyrazines and their N-Oxides with Tetraphenyltin," Heterocycles 24:785-792 (1986).

Schulz et al., "CP-154,526: A potent and selective nonpeptide antagonist of corticotropin releasing factor receptors," Proc. Natl. Acad. Sci. USA 93:10477-10482 (1996).

Smagin et al., "Corticotropin-releasing factor receptor antagonist infused into the locus coeruleus attenuates immobilization stress-induced defensive withdrawal in rats," Neuroscience Letters 220:167-170 (1996).

Smagin et al., "CRF Receptor Antagonist Attenuates Immobilization Stres-Induced Norepinephrine Release in the Prefrontal Cortex in Rats," Brain Research Bulletin 42:431-434 (1997).

Taylor et al., "Intramolecular Diels-Alder Reactions of 1, 2, 4-Triazines. Routes to Condensed Pyrazines via Cycloaddition of Nitrile Dienophiles," J. Org. Chem. 54:1245-1249 (1989).

Taylor et al., "Synthesis of Pyridines by Diels-Alder Reactions of Hetero-Substituted 1, 2, 4-Triazines with Enamines and an Enaminone," J. Org. Chem. 54:1249-1256 (1989).

Vinot et al., "No. 797.—Synthase de pyrazines," Bulletin de la Societe Chimique de France 12:4970-4974 (1968).

Yamagami et al., "Measurement and Prediction of Hydrophobicity Parameters for Highly Lipophilic Compounds: Application of the HPLC Column-Switching Technique to Measurement of log P of Diarylpyraines," Journal of Pharmaceutical Sciences 88;1299-1304 (1999).

CAS Printout of Hamazald et al., Chem Abs. 100:5477, (1984).
CAS Printout of Hori et al., Chem. Abs. 80:890 (1974).
CAS Printout of Inoue et al., Chem. Abs. 93:11448, (1980).
CAS Printout of McCarpra et al., Chem. Abs. 79:125387, (1973).
CAS Printout of Miescl et al., Chem. Abs. 96:35307, (1982).
CAS Printout of Rees et al., (WO 08/43641).
CAS Printout of Teranishi et al. (JP 10077286) (1998).
CAS Printout of Teranishi et al. (JP 1998-184331).
CAS Printout of Teranishi et al., Chem Abs. 114:101506, (1991).

* cited by examiner

5-SUBSTITUTED-2-ARYLPYRAZINES

The present application claims the benefit of U.S. provisional application No. 60/405,013, filed Aug. 20, 2002, which is incorporated herein by reference in its entirety.

BACKGROUND

1. Field of the Invention

The present invention relates to 5-substituted-2-arylpyrazine compounds. Such compounds bind with high selectivity and/or high affinity to CRF1 receptors (Corticotropin Releasing Factor 1 Receptors). Preferred compounds block, inhibit, activate, or otherwise modulate the activity of the receptors to which they bind. This invention also relates to pharmaceutical compositions comprising such compounds and to the use of such compounds in treatment of psychiatric disorders and neurological diseases, including major depression, anxiety-related disorders, post-traumatic stress disorder, supranuclear palsy and feeding disorders, as well as treatment of immunological, cardiovascular or heart-related diseases, irritable bowel syndrome, and colonic hypersensitivity associated with psychopathological disturbance and stress. Additionally this invention relates to the use such compounds as probes for the localization of CRF1 receptors in cells and tissues.

2. Background of the Invention

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

CRF acts by binding to and modulating the signal transduction activities of specific cell surface receptors, including CRF1 receptors and CRF2 receptors. These receptors are found at high concentrations in the central nervous system (CNS), particularly in certain regions of the brain. CRF1 receptors are also found outside the CNS.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders.

CRF has been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF activity has also been implicated in the pathogeneisis of certain cardiovascular or heart-related, digestive, degenerative, dermatological, and immunological, diseases and disorders such as hypertension, tachycardia and congestive heart failure, stroke, acne and osteoporosis, as well as in premature birth, psychosocial dwarfism, stress-induced fever, ulcer, diarrhea, post-operative ileus and colonic hypersensitivity, e.g., associated with psychopathological disturbance and stress.

SUMMARY OF THE INVENTION

The invention provides novel compounds of Formula I (shown below). The invention also comprises pharmaceutical compositions comprising compounds of Formula I and at least one pharmaceutically acceptable carrier or excipient. Such 5-substituted-2-arylpyrazines bind to cell surface receptors, preferably G-coupled protein receptors, especially CRF receptors and most preferably CRF1 receptors. Preferred compounds of Formula I exhibit high affinity for CRF1 receptors, i.e., they bind to, activate, inhibit, or otherwise modulate the activity of receptors other than CRF receptors with affinity constants of less than 1 micromolar, preferably less than 100 nanomolar, and most preferably less than 10 nanomolar. Additionally, preferred compounds of Formula I also exhibit high selectivity for CRF1 receptors.

The invention further comprises methods of treating patients suffering from certain diseases or disorders by administering to such patients an amount of a compound of Formula I effective to reduce signs or symptoms of the disease or disorder. These diseases and disorders include CNS disorders, particularly affective disorders, anxiety, stress, depression, and eating disorders and also include certain digestive disorders, particularly irritable bowel syndrome and Crohn's disease. These diseases or disorders further include cardiovascular or heart-related, digestive, degenerative, dermatological, and immunological, diseases and disorders such as hypertension, tachycardia and congestive heart failure, stroke, acne and osteoporosis, as well as premature birth, psychosocial dwarfism, stress-induced fever, ulcer, diarrhea, post-operative ileus and colonic hypersensitivity. The patient suffering from such diseases or disorders may be a human or other animal (preferably a mammal), such as a domesticated companion animal (pet) or a livestock animal.

According to yet another aspect, the present invention provides pharmaceutical compositions comprising a compound of Formula I or pharmaceutically acceptable salts or solvates thereof together with at least one pharmaceutically acceptable carrier or excipient, which compositions are useful for the treatment of the disorders recited above. The invention further provides methods of treating patients suffering from any of these disorders with an effective amount of a compound or composition of Formula I.

Additionally this invention relates to the use of labeled compounds of Formula I (particularly radiolabeled compounds of this invention) as probes for the localization of receptors in cells and tissues and as standards and reagents for use in determining the receptor-binding characteristics of test compounds.

Thus, in a first aspect, the invention is directed to compounds of Formula I

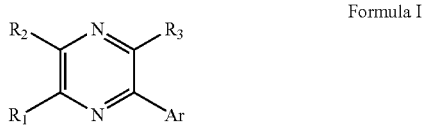

Formula I and the pharmaceutically acceptable salts thereof.

Ar is substituted phenyl, optionally substituted naphthyl, or an optionally substituted heteroaryl group having from 1 to 3 rings, and 3 to 8 ring members in each ring and from 1 to about 3 heteroatoms in at least one of said rings.

$R_2$ is optionally substituted alkyl, optionally substituted alkenyl, optionally substituted alkynyl, optionally substituted alkylamino, optionally substituted alkoxy, optionally substituted alkylthio, optionally substituted alkylsulfinyl, or optionally substituted alkylsulfonyl.

$R_1$ and $R_3$ are each independently hydrogen, halogen, cyano, nitro, amino, optionally substituted alkyl, optionally substituted alkenyl, optionally substituted alkynyl, optionally substituted mono or dialkylamino, optionally substituted alkoxy, optionally substituted alkylthio, optionally substituted alkylsulfinyl, or optionally substituted alkylsulfonyl.

If Ar is phenyl substituted with halogen, naphthyl, or naphthyl substituted with halogen, then $R_3$ is not hydrogen or amino.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature. Certain compounds are described herein using a general formula that includes variables. Unless otherwise specified, each variable within such a formula is defined independently of other variables.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Where a compound exists in various tautomeric forms, the invention is not limited to any one of the specific tautomers, but rather includes all tautomeric forms. In these situations, the single enantiomers, i.e. optically active forms, can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom is replaced with a selection from the indicated group, provided that the designated atom's normal valence is not exceeded, and that the substitution results in a stable compound. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a dihydropyridone.

As indicated above, various substituents of Formula I and Formula IA and Formula I-Formula E (described below) are "optionally substituted". The phrase "optionally substituted" indicates that such groups may either be unsubstituted or substituted at one or more of any of the available positions, typically 1, 2, 3, or 4 positions, by one or more suitable groups such as those disclosed herein.

When substituents such as Ar, $R_1$, $R_2$, $R_3$, and $R_4$, are further substituted, they may be so substituted at one or more available positions, typically 1 to 3 or 4 positions, by one or more suitable groups such as those disclosed herein. Suitable groups that may be present on a "substituted" Ar or other group include e.g., halogen; cyano; hydroxyl; nitro; azido; alkanoyl (such as a $C_{1-6}$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_{1-6}$ alkyl as used herein includes alkyl groups consisting of 1 to 6 carbon atoms. When $C_0$–$C_n$alkyl is used herein in conjunction with another group, for example, aryl$C_0$–$C_4$alkyl, the indicated group, in this case aryl, is either directly bound by a single covalent bond, or attached by an alkyl chain having the specified number of carbon atoms, in this case from 1 to 4 carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_{1-8}$ and $C_{1-6}$ alkyl groups. Especially preferred alkyl groups are methyl, ethyl, propyl, butyl, and 3-pentyl. "Carbhydryl" is intended to include both branched and straight-chain hydrocarbon groups, which are saturated or unsaturated, having the specified number of carbon atoms.

"Alkenyl" is intended to include hydrocarbon chains of either a straight or branched configuration comprising one or more unsaturated carbon-carbon bonds, which may occur in any stable point along the chain, such as ethenyl and propenyl.

"Alkynyl" is intended to include hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkoxycarbonyl" indicates a group of the formula:

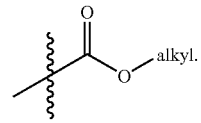

The number of carbons listed, e.g. $C_{1-2}$alkoxycarbonyl, indicates the number of carbon atoms in the alkyl chain.

"Alkylcarboxamide" is a group of the formula —C(=O)NHalkyl.

As used herein, the term "mono- and di-alkylamino" includes secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, methylpropyl-amino. The term "mono- and di-alkylaminoalkyl" is used to indicate and alkyl group, as described above, substituted by a mono- or di-alkylamino group, as described above.

As used herein, the term "aminoalkyl" indicates an alkyl group substituted at the terminal position by $NH_2$, e.g. a 3-propylamine group.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylthio" includes those groups having one or more thioether linkages and preferably from 1 to about 8 carbon atoms, more typically 1 to about 6 carbon atoms.

As used herein, the term "aryl" indicates aromatic groups containing only carbon in the aromatic ring. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Specifically preferred aryl groups include phenyl, naphthyl, including 1-naphthyl and 2-naphthyl, and biphenyl. The definition of the term "aryl" is not identical to that of the variable "Ar".

As used herein, "carbocyclic group" is intended to mean any stable 3- to 7-membered monocyclic group, which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, cyclohexenyl, and phenyl.

"Cycloalkyl" is intended to include saturated hydrocarbon ring groups, having the specified number of carbon atoms, usually from 3 to about 8 ring carbon atoms. Preferred cycloalkyl groups have from 3 to 7 ring carbon atoms. Examples of cycloalkyl groups include cyclopropyl, cyclobutyl, cyclopentyl, or cyclohexyl and bridged or caged saturated ring groups such as norbornane or adamantane and the like.

In the term "(cycloalkyl)alkyl", cycloalkyl and alkyl are as defined above, and the point of attachment is on the alkyl group. This term encompasses, but is not limited to, cyclopropylmethyl, cyclohexylmethyl, and cyclohexylmethyl. Likewise, in the term "(cycloalkyl)alkoxy", cycloalkyl and alkoxy are as define above, and the point of attachment in the oxygen of the alkoxy group. The term "cycloalkyloxy" indicates a cycloalkyl group, as defined above, attached through an oxygen bridge.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, the terms "heteroaryl" is intended to indicate a stable 5- to 7-membered monocyclic or bicyclic or 7- to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, it is understood that these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

The term "heterocycloalkyl" is used to indicate saturated cyclic groups containing from 1 to about 3 heteroatoms selected from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, and pyrrolidinyl groups.

As used herein, the term "heterocyclic group" is intended to include 3 to 7 membered saturated, partially unsaturated, or aromatic monocyclic groups having at least one atom selected from N, O or S. The remaining ring atoms are carbon. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen atom in the heterocycle may optionally be quaternized. It is preferred that the total number of heteroatoms in the heterocyclic groups is not more than 4 and that the total number of S and O atoms in the heterocyclic group is not more than 2, more preferably not more than 1.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl.

As used herein, "pharmaceutically acceptable salts" refer to derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, dibesylic, sulfanilic, 2-acetoxybenzoic, fumaric, toluenesulfonic, methanesulfonic, ethane disulfonic, oxalic, isethionic, HOOC—$(CH_2)_n$—COOH where n is 0–4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

"Prodrugs" are intended to include any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to antagonize the effects of pathogenic levels of CRF or to treat the symptoms of stress disorders, affective disorder, anxiety or depression.

CRF1 Receptor Ligands

The present invention is based, in part, on the discovery that small molecules having the general Formula I, shown above (as well as pharmaceutically acceptable salts and prodrugs thereof) act as antagonists and/or inverse agonists of CRF1 receptors.

In addition to compounds and pharmaceutically acceptable salts of Formula I set forth above, the invention provides certain compounds of Formula I, which will be referred to as compounds of Formula IA, in which $R_1$, $R_2$, $R_3$, and Ar carry the values set forth below.

Ar, in compounds of Formula IA, is phenyl, mono-, di-, or tri-substituted with $R_A$, or Ar is selected from the group consisting of: naphthyl, pyridyl, pyridonyl, pyrimidinyl, and thiophenyl, each of which is unsubstituted or mono-, di-, or tri-substituted with $R_A$.

$R_1$ is selected from H, $C_{1-4}$ alkyl, $C_{2-4}$ alkenyl, $C_{2-4}$ alkynyl, halogen, CN, $C_{1-4}$ haloalkyl, $C_{1-4}$haloalkoxy, mono- and di-$C_{1-4}$alkylamino, $C_{1-4}$alkoxy, and $S(O)_n(C_{1-4}$ alkyl).

$R_2$ is selected from the group consisting of —$XR_C$ and Y, wherein —X, $R_C$, and Y are defined below.

$R_3$ is selected from the group consisting of hydrogen, halogen, $C_{1-4}$ alkyl, $C_{1-4}$ alkoxy, mono- and di-$C_{1-4}$alkylamino, and —$S(O)_n(C_{1-4}$ alkyl), $C_{1-4}$ haloalkyl, $C_{1-4}$haloalkoxy, and —$XR_C$.

$R_4$ is independently selected at each occurrence from the group consisting of halogen, cyano, $C_{1-4}$haloalkyl, $C_{1-4}$haloalkoxy, hydroxy, amino, and $C_{1-6}$alkyl optionally substituted with 0–2 $R_B$, $C_{2-6}$ alkenyl substituted with 0–2 $R_B$, $C_{1-4}$ alkynyl substituted with 0–2 $R_B$, $C_{3-7}$ cycloalkyl substituted with 0–2 $R_B$, ($C_{3-7}$ cycloalkyl)$C_{1-4}$ alkyl substituted with 0–2 $R_B$, $C_{1-4}$ alkoxy substituted with 0–2 $R_B$, —NH($C_{1-4}$ alkyl) substituted with 0–2 $R_B$, —N($C_{1-4}$alkyl)($C_{1-4}$ alkyl) each independently substituted with 0–2 $R_B$, —$XR_C$, and Y.

$R_B$ is independently selected at each occurrence the group consisting of halogen, hydroxy, cyano, $C_{1-4}$alkyl, $C_1$–$C_4$alkoxy, mono- and di-($C_1$–$C_4$alkyl)amino, —$S(O)_n$(alkyl), halo($C_1$–$C_4$)alkyl, halo($C_1$–$C_4$)alkoxy, morpholino, pyrrolidino, piperidino, thiomorpholino, piperazino, 4-hydroxypiperidino, —$S(O)_n(C_{1-4}$alkyl), —$CO(C_{1-4}$alkyl), —$CONH(C_{1-4}$alkyl), —$CON(C_{1-4}$alkyl)($C_{1-4}$alkyl), —$XR_C$, and Y.

$R_C$ and $R_D$, are the same or different, and are independently selected at each occurrence from hydrogen, and straight, branched, and cyclic alkyl groups and (cycloalkyl) alkyl groups, having 1 to 8 carbon atoms, and containing zero or one or more double or triple bonds, each of which 1 to 8 carbon atoms may be further substituted with one or more substituent (s) selected from oxo, hydroxy, halogen, $C_{1-4}$ alkoxy, mono- and di-$C_{1-4}$alkylamino, —NHC(=O)($C_{1-4}$ alkyl), —N($C_{1-4}$ alkyl)C(=O)($C_{1-4}$ alkyl), —NHS(O)$_n$ ($C_{1-4}$ alkyl), —$S(O)_n(C_{1-4}$ alkyl), —$S(O)_n$NH($C_{1-4}$ alkyl), —$S(O)_n$N($C_{1-4}$ alkyl)($C_{1-4}$ alkyl), and Z.

X is independently selected at each occurrence from the group consisting of —$CH_2$—, —$CHR_D$—, —O—, —C(=O)—, —C(=O)O—, —$S(O)_n$—, —NH—, —$NR_D$—, —C(=O)NH—, —C(=O)$NR_D$—, —$S(O)_n$NH—, —$S(O)_nNR_D$—, —OC(=S)S—, —NHC(=O)—, —$NR_DC(=O)$—, —NHS(O)$_n$—, and —$NR_DS(O)_n$—.

Y and Z are independently selected at each occurrence from 3- to 7-membered carbocyclic and heterocyclic groups, which are saturated, partially unsaturated, or aromatic, which may be substituted with one or more substituents selected from halogen, hydroxy, haloalkyl, oxo, hydroxy, amino, $C_{1-4}$ alkyl, $C_{1-4}$alkoxy, mono- and di-($C_{1-4}$alkyl)amino, and —$S(O)_n$(alkyl), wherein said 3- to 7-membered heterocyclic groups contain from 1 to 3 heteroatom(s) selected from N, O, and S, with remaining ring atoms being carbon.

The variable "n" is independently selected at each occurrence from 0, 1, and 2.

If Ar, in a compound of Formula IA, is phenyl substituted with halogen, naphthyl, or naphthyl substituted with halogen, then $R_3$ is not hydrogen.

In certain preferred compounds of the invention include compounds and salts of Formula I of Formula IA in which Ar is substituted phenyl, preferably mono-, di-, or tri-substituted with $R_4$.

The invention also includes compounds and salts of Formula I and Formula IA in which Ar is phenyl, mono-, di-, or tri-substituted with $R_4$, and $R_1$ and $R_3$ are independently selected from the group consisting of hydrogen, halogen, methyl, ethyl, ethoxy and methoxy.

The invention includes compounds of Formula I and Formula IA in which Ar is phenyl, mono-, di-, or tri-substituted with $R_4$; and $R_C$ and $R_D$, are the same or different, and are independently straight, branched, or cyclic alkyl groups having from 1 to 8 carbon atoms, which contain 0 or one or more double or triple bonds. In certain preferred compounds and salts of this type $R_1$ and $R_3$ are independently selected from the group consisting of hydrogen, halogen, methyl, ethyl, ethoxy, and methoxy.

In addition, the invention includes certain compounds and pharmaceutically acceptable salts of Formula A

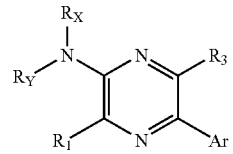

Formula A $R_1$, $R_3$, and Ar in Formula A carry the definitions set forth for Formula IA.

$R_X$ and $R_Y$, in Formula A, are the same or different and are independently selected from straight, branched, and cyclic alkyl groups and (cycloalkyl)alkyl group, having 1 to 8 carbon atoms, and containing zero or one or more double or triple bonds, each of which 1 to 8 carbon atoms may be further substituted with one or more substituent(s) independently selected from hydroxy, halogen, $C_{1-4}$ alkoxy, mono- and di-($C_{1-4}$ alkyl)amino, and optionally substituted phenyl.

The invention further provides compounds of Formula A in which:

$R_X$ and $R_Y$ carry the definitions set forth above for compounds of Formula A.

Ar is phenyl, mono-, di-, or tri-substituted with $R_4$ (which carries the definition set forth above for Formula IA).

$R_1$ and $R_3$ in these compounds are independently selected from the group consisting of hydrogen, halogen, methyl, ethyl, ethoxy and methoxy.

The invention also provides compounds of Formula A in which:

Ar is phenyl, which is mono-, di-, or tri-substituted with one or more substituent(s) independently selected from: halogen, cyano, $C_{1-2}$haloalkyl (preferably trifluoromethyl), $C_{1-2}$haloalkoxy (preferably trifluoromethoxy), hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- and di-($C_{1-4}$ alkyl)amino.

More preferably Ar is a phenyl group of the formula:

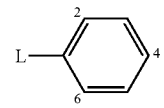

wherein L indicates a bond to the pyrazine ring in Formula A; and the phenyl group is substituted with the substituents list above for Ar groups of Formula A at one, two or three of positions 2, 4, and 6.

$R_1$ and $R_3$, in these compounds, are independently chosen from halogen, $C_{1-4}$ alkyl, $C_{1-4}$ alkoxy, mono- and di-($C_{1-4}$ alkyl)amino, $C_1$–$C_2$haloalkyl (preferably trifluoromethyl), $C_{1-2}$haloalkoxy (preferably trifluoromethoxy).

$R_X$, for certain preferred compounds is hydrogen; and $R_Y$ is chosen from the group consisting of: straight, branched, or cyclic alkyl groups and (cycloalkyl)alkyl groups having 1 to 8 carbon atoms, and containing one or more double or triple bonds.

The invention provides compounds and pharmaceutically acceptable salts of Formula A in which $R_1$, $R_3$, and Ar carry the definitions set forth for compounds of Formula IA and $R_X$ and $R_Y$ are independently hydrogen or $C_{1-8}$ alkyl; or $R_X$ and $R_Y$ are joined to form a group of the Formula

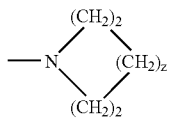

wherein z is 0 or 1.

Further provided by the invention are compounds and pharmaceutically acceptable salts of Formula B

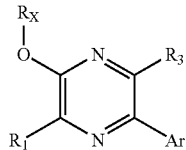

Formula B $R_1$, $R_3$, and Ar in Formula B carry the definitions set forth for Formula IA.

$R_X$, in Formula B is chosen from the group consisting of: straight, branched, or cyclic alkyl groups and (cycloalkyl) alkyl groups, having from 1 to 8 carbon atoms, containing zero or one or more double or triple bonds, each of which may be further substituted with one or more substituent(s) independently selected from (a) hydroxy, halogen, —$C_{1-4}$ alkoxy, and mono- and di-($C_{1-4}$alkyl)amino, and (b) 3- to 7-membered carbocyclic and heterocyclic groups, which are saturated, partially unsaturated, or aromatic, which may be substituted with one or more substituents selected from halogen, haloalkyl, oxo, hydroxy, amino, $C_{1-4}$ alkyl, —$C_{1-4}$ alkoxy, and mono- and di-($C_{1-4}$alkyl)amino and wherein said 3- to 7-membered heterocyclic groups contain one or more heteroatom(s) selected from N, O, and S.

Preferred compounds of Formula B provided by the invention include those compounds in which:

$R_X$ is selected from straight, branched, and cyclic alkyl groups and (cycloalkyl)alkyl groups containing of 1 to 8 carbon atoms, having zero or one or more double or triple bonds.

$R_1$ and $R_3$, in these compounds of Formula C, are independently chosen at each occurrence from halogen, $C_{1-4}$ alkyl, $C_{1-4}$ alkoxy, mono- and di-($C_{1-4}$ alkyl)amino, —$C_1$–$C_2$haloalkyl (preferably trifluoromethyl), and $C_{1-2}$haloalkoxy (preferably trifluoromethoxy).

Ar is phenyl, which is mono-, di-, or tri-substituted with one or more substituent(s) independently selected from: halogen, cyano, $C_1$–$C_2$haloalkyl (preferably trifluoromethyl), $C_{1-2}$haloalkoxy (preferably trifluoromethoxy), hydroxy, amino, and $C_{1-6}$ alkyl, $C_{1-4}$alkoxy, $C_{1-4}$alkoxy($C_{1-4}$ alkoxy), mono- or di($C_4$)amino($C_{1-4}$alkoxy), and mono- and di-($C_{1-4}$ alkyl)amino.

More preferably Ar is a phenyl group of the formula:

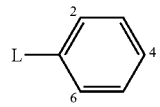

wherein L indicates a bond to the pyrazine ring in Formula B; and the phenyl group is substituted at one, two or three of positions 2, 4, and 6 with substituents independently chosen from those listed above for Ar group of compounds of Formula B. Other preferred compounds of Formula B include those wherein Ar is a phenyl group of the formula shown immediately above, substituted positions 2 and 4 with substituents independently chosen from those listed above for Ar group of compounds of Formula B.

The invention also provides compounds and pharmaceutically acceptable salts of Formula C and Formula D

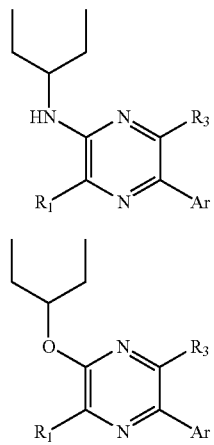

Formula C

Formula D $R_1$ and $R_3$, in Formula C and Formula D, are independently chosen at each occurrence from halogen, $C_{1-4}$ alkyl, $C_{1-4}$ alkoxy, mono- and di-($C_{1-4}$ alkyl)amino, —$C_1$–$C_2$haloalkyl (preferably trifluoromethyl), and $C_{1-2}$haloalkoxy (preferably trifluoromethoxy). Preferably $R_1$ and $R_3$ are independently selected from the group consisting of hydrogen, halogen, methyl, ethyl, ethoxy and methoxy.

Ar, in Formula C and Formula D, is a phenyl group of the formula:

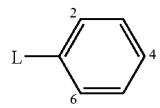

wherein L indicates a bond to the pyrazine ring in Formula C and Formula D; and the phenyl group is substituted at one, two or three of positions 2, 4, and 6 with substituent(s) independently selected from: halogen, cyano, —$C_1$–$C_2$haloalkyl (preferably trifluoromethyl), and $C_{1-2}$haloalkoxy (preferably trifluoromethoxy),hydroxy, amino, and $C_{1-6}$ alkyl, $C_{1-4}$alkoxy, $C_{1-4}$alkoxy($C_{1-4}$alkoxy), mono- or di($C_{1-4}$alkyl)amino($C_{1-4}$alkoxy), and mono- or di($C_{1-4}$ alkyl) amino. Other preferred compounds of Formula C and Formula D include those wherein Ar is a phenyl group of the formula shown immediately above, substituted positions 2 and 4 with substituents independently chosen from those listed above for Ar group of Formula C or Formula D.

The invention further provides compounds and pharmaceutically acceptable salts of Formula E

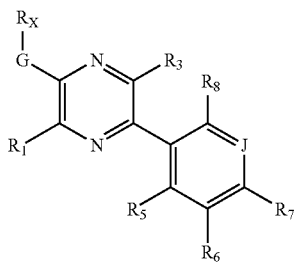

Formula E

G, in Formula E, is oxygen or NH.

$R_X$ is straight or branched chain $C_{1-8}$alkyl.

$R_1$ and $R_3$ are independently selected from hydrogen, $C_{1-4}$ alkyl, halogen, $C_{1-2}$ haloalkyl, $C_{1-2}$haloalkoxy, mono- and di-$C_{1-4}$alkylamino, $C_{1-4}$alkoxy, and $C_{1-4}$ alkylthio.

$R_5$ is halogen, $C_{1-6}$alkyl, preferably $C_{1-4}$alkyl, or $C_{1-6}$alkoxy, preferably $C_{1-4}$alkoxy, each of which may be optionally substituted with one or more groups such as hydroxy, $C_{1-4}$alkoxy or the like.

$R_6$ is hydrogen, halogen, $C_{1-6}$alkyl, preferably $C_{1-2}$alkyl, or $C_{1-6}$alkoxy, preferably $C_{1-2}$alkoxy, each of which may be optionally substituted with one or more groups such as hydroxy, $C_{1-4}$alkoxy or the like.

$R_7$ is halogen, halogen, cyano, $C_{1-4}$alkyl, $C_{1-4}$alkoxy, $C_{1-2}$ haloalkyl, $C_{1-2}$haloalkoxy, mono- and di-$C_{1-4}$alkylamino, mono- and di-($C_{1-2}$alkyl)amino$C_{1-4}$alkyl, $C_{1-2}$alkoxy$C_{1-4}$ alkyl, $C_{1-2}$alkoxycarbonyl, $C_{1-2}$alkylcarboxaminde, —C(=O)NH$_2$, hydroxy$C_{1-2}$alkyl, trifluoromethylsulfonyl, 2,2,2-trifluoroethanol, or a 4–7 membered heterocycloalkyl group containing 1 or 2 atoms independently chosen from N, O, and S, each of which may be optionally substituted with one or more groups such as hydroxy, $C_{1-4}$alkoxy or the like.

$R_8$ is hydrogen, halogen, $C_{1-4}$alkyl, preferably $C_{1-2}$alkyl, $C_{1-2}$alkoxy, preferably $C_{1-2}$alkoxy, or mono or di$C_{1-6}$alkylamino which may be optionally substituted with one or more groups selected from halogen, hydroxy, $C_{1-4}$alkoxy, or a 4–7 membered heterocycloalkyl group containing 1 or 2 atoms independently chosen from N, O, and S J is N or CR$_9$ where R$_9$ is hydrogen, halogen or $C_{1-2}$alkyl.

Certain preferred compounds and salts according to Formula E include those compounds in which $R_1$ and $R_3$ are not hydrogen. The invention comprises compounds and salts of Formula E in which J is nitrogen and $R_6$ is hydrogen. The invention also comprises compounds and salts of Formula E in which J is CH and $R_6$ is hydrogen.

The invention further provides compounds or salts of Formula E wherein G is NH and $R_X$ is 1-ethyl propyl. Particularly preferred compounds and salts of Formula E include those compounds in which $R_1$ is cyano, methoxy, or methylthio and $R_3$ is methyl or ethyl when G is NH and $R_X$ is 1-ethylpropyl.

The invention also provides compounds and salts of Formula E wherein G is oxygen and $R_X$ is 1-ethylpropyl, 1-isopropyl-2-methypropyl, 1-propylbutyl, or 1-ethylbutyl. It is preferred that $R_3$ is halogen, $C_{1-2}$alkyl, or methylamino for compounds and salts of these compounds. It is also preferred that $R_1$ is halogen, methyl, methoxy, ethyl, ethoxy, or $C_{1-2}$alkylamino for compounds and salts of these compounds of Formula E. Compounds and salts of Formula E in which G is oxygen, Rx is a branched chain alkyl, e.g. -ethylpropyl, 1 isopropyl-2-methypropyl, 1-propylbutyl, or 1-ethylbutyl, and $R_1$ is methylamino are also preferred.

Certain preferred Ar groups for compounds of Formula I, IA, and A–D, include, but are not limited to 2-methoxy-4-(trifluoromethoxy)phenyl, 4-tert-butyl-2-methoxyphenyl, 4-isopropyl-2-methoxyphenyl, 2,6-dimethoxypyridin-3-yl (i.e. the numbering of the pyridine ring begins at 1 on the nitrogen and the pyridine is attached to the pyrazine core at the 3 position), 4-ethyl-2-methoxyphenyl, 2-chloro-4-(difluoromethoxy)phenyl, 2-fluoro-4,6-dimethoxyphenyl, 4-(difluoromethoxy)-2-methoxyphenyl, 2-methoxy-6-dimethylamino-pyridin-3-yl, 2,5-diethyl-3-(1-ethylpropoxy)-6-(4-isopropyl-2-methoxyphenyl)pyrazine, and the like.

Preferred compounds of Formula I exhibit a $K_i$ value of 1 micromolar or less in a standard in vitro CRF receptor binding assay. More preferred compounds exhibit a $K_i$ value of 100 nanomolar or less in a standard in vitro CRF receptor binding assay. Particularly preferred compounds of Formula I exhibit a $K_i$ value of 10 nanomolar or less in a standard in vitro CRF receptor binding assay. A standard in vitro CRF1 receptor binding assay is disclosed in Example 30, below.

The invention further provides intermediates useful in the preparation of compounds of Formula I, Formula IA, any the particular subformula thereof (e.g., Formula II-Formula E), or any of the compounds of Formula I specifically disclosed herein. Intermediates useful in the synthesis of compounds in the invention are described in Schemes I–IV below, and further illustrated in Examples 1–28. For example, useful intermediates provided by the invention include aryl metallo compounds and aryl boronic acids useful for coupling to the pyridine core of Formula I. Particular examples of such intermediates include, for example 4-methoxy-2-methylbenzeneboronic acid, 2-Methoxy-6-isopropyl-3-pyridylboronic acid (step 3, example 4), and 4-Trifluoromethoxy-2-methoxy-phenylboronic acid (see step 6, example 5).

The invention also provides pharmaceutical compositions comprising a compound, pharmaceutically acceptable salt, or prodrug of Formula I, Formula IA, any the particular subformula thereof (e.g., Formula A-Formula E), or any of the compounds of Formula I specifically disclosed herein, together with a pharmaceutically acceptable carrier or excipient. Pharmaceutically acceptable carriers suitable for use in a composition provided by the invention may be inert, or may modulate the bioavailability or stability of the active compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polyacetate, polyglycolate, poly(lactide-co-glycolide), polyacrylate, starch, cellulose or dextran. The pharmaceutical composition, may be prepared in a variety of forms, for example, as an injectable fluid, an aerosol, a cream, a gel, a pill, a capsule, a syrup, or a transdermal patch.

The invention also provides packages comprising a pharmaceutical composition as described immediately above in a container and instructions for using the composition to treat a patient suffering from anxiety, or instructions for using the composition to treat a patient suffering from stress, or instructions for using the composition to treat a patient suffering from depression, or instructions for using the composition to treat a patient suffering from irritable bowel syndrome or instructions for using the composition to treat a patient suffering from Crohn's disease.

The CRF binding compounds provided by this invention and labeled derivatives thereof are also useful as standards and reagents in determining the ability of other compounds (e.g., a potential pharmaceutical agent) to bind to the CRF receptor.

The invention provides a method for demonstrating the presence of CRF receptors (preferably CRF1 receptors) in a biological sample (e.g., a tissue section or homogenate), said method comprising contacting the biological sample with a labeled compound of Formula I under conditions that permit binding of the labeled compound to a CRF receptor and detecting the labeled compound in the biological sample. Unbound labeled compound is preferably at least partially removed from the biological sample prior to detecting the bound labeled compound in the sample.

For detection purposes the compound may be labeled, for example, with a fluorescent, isotopic, or radiolabel. Radiolabeled and isotopically labeled compounds of Formula I, IA, and A–D, which are also included in the invention, are identical to the compounds recited in Formulae I, IA, and A–D, with one or more atoms replaced by an atom having an atomic mass or mass number different from the most highly abundant isotope of that atom. Examples of isotopes that can be incorporated into compounds of Formula I in accordance with this aspect of the invention includes isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$. PREPARATION OF such radiolabeled compounds of Formula I is described below in Example 31. The labeled compound may be detected if radiolabeled, e.g., autoradiographically, and if otherwise isotopically labeled, e.g., by NMR. Labeled derivatives of the CRF antagonist compounds of Formula I are also useful as radiotracers for positron emission tomography (PET) imaging or for single photon emission computerized tomography (SPECT).

The present invention also pertains to methods of inhibiting the binding of CRF to CRF receptors which methods involve contacting a solution containing a compound of Formula I with at least one cell (e.g., a neuronal cell) expressing CRF receptors (e.g., preferably CRF1 receptors), wherein the compound is present in the solution at a concentration sufficient to inhibit CRF binding to CRF receptors in vitro. This method includes inhibiting the binding of CRF to CRF receptors in vivo in an animal (e.g., preferably a human patient). The animal is given an amount of a compound of Formula I that results in a concentration in a relevant body fluid (e.g., blood, plasma, serum, CSF, interstitial fluid) of the animal, which concentration is at least sufficient to inhibit the binding of CRF to CRF receptors in vitro.

The present invention also pertains to methods of altering (i.e. increasing or decreasing) the CRF-stimulated activity of CRF receptors, which methods involve contacting a solution containing a compound Formula I with at least one cell (e.g., a neuronal cell) expressing CRF receptors (e.g., preferably CRF1 receptors), wherein the compound is present in the solution at a concentration sufficient to alter the CRF-stimulated signal transduction activity of CRF receptors in cells expressing CRF receptors (preferably cells expressing such receptors at levels above those found in naturally occurring CRF receptor-expressing cells) in vitro. This method includes altering the CRF-stimulated activity of CRF receptors in vivo in an animal (e.g., preferably a human patient). The animal is given an amount of a compound of Formula I that results in a compound a concentration in a relevant body fluid (e.g., blood, plasma, serum, CSF, interstitial fluid) of the animal, which concentration is at least sufficient to alter the CRF-stimulated activity of CRF receptors in vitro.

Certain preferred methods of the invention are useful in treating physiological disorders associated with excess concentrations of CRF in a patient (e.g., in a body fluid of the patient). The amount of a compound that would be sufficient to inhibit the binding of a CRF to a CRF receptor or to alter the CRF-stimulated activity of CRF receptors may be readily determined via a CRF receptor binding assay (see Example 30), or from the $EC_{50}$ of a CRF receptor functional assay. CRF receptors that may be used to determine in vitro binding are found in a variety of sources, for example in cells that autologously express CRF receptors, e.g. IMR32 cells, or in a cell expressing a CRF receptor as a result of the expression of an exogenous CRF receptor-encoding polynucleotide comprised by the cell.

Methods of Treatment

Compounds of Formula I are useful in treating a variety of conditions including affective disorders, anxiety disorders, stress disorders, eating disorders, digestive disorders, and drug addiction.

Affective disorders include all types of depression, bipolar disorder, cyclothymia, and dysthymia.

Anxiety disorders include generalized anxiety disorder, panic, phobias and obsessive-compulsive disorder.

Stress, includes, for example, post-traumatic stress disorder, hemorrhagic stress, stress-induced psychotic episodes, psychosocial dwarfism, stress headaches, stress-induced immune systems disorders such as stress-induced fever, and stress-related sleep disorders.

Eating disorders include anorexia nervosa, bulimia nervosa, and obesity.

Digestive disorders include, but are not limited to, irritable bowel syndrome and Crohn's disease.

Modulators of the CRF receptors may also be useful in the treatment of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy.

Additionally compounds of Formula I are useful as modulators of the CRF receptor in the treatment of a number of gastrointestinal, cardiovascular, hormonal, autoimmune and inflammatory conditions. Such conditions include ulcers, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies.

Compounds of Formula I are also useful as modulators of the CRF1 receptor in the treatment of animal disorders associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia.

Typical subjects to which compounds of Formula I may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrathecal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired, other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, or flavoring or coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile an injectable solution or suspension in a non-toxic parentally acceptable dilutent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most CNS disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of Formula I will have certain pharmacological properties. Such properties include, but are not limited to oral bioavailability, optimal volume of distribution, low toxicity, low serum protein binding, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

As discussed above, preferred arylpyrazines of Formula I exhibit activity in standard in vitro CRF receptor binding assays, specifically the assay as specified in Example 30, which follows. References herein to "standard in vitro receptor binding assay" are intended to refer to that protocol as defined in Example 30 which follows. Generally preferred arylpyrazines of Formula I have a $K_i$ of about 1 micromolar or less, still more preferably a $K_i$ of about 100 nanomolar or less even more preferably a $K_i$ of about 10 nanomolar or less or even 1 nanomolar or less in such a defined standard in vitro CRF receptor binding assay as exemplified by Example 30 which follows.

EXAMPLES

PREPARATION OF 5-SUBSTITUTED-2-ARYLPYRAZINES

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. Preferred methods for the preparation of compounds of the present invention include, but are not limited to, those described in Schemes I–IV. Those who are skilled in the art will recognize that the starting materials may be varied and additional steps employed to produce compounds encompassed by the present invention. All references cited herein are hereby incorporated in their entirety herein by reference. The following abbreviations are used herein:

| | |
|---|---|
| AcOH | acetic acid |
| DMF | N,N-dimethylformamide |
| Et$_2$O | diethyl ether |
| EtOAc | ethyl acetate |
| EtOH | ethanol |
| NaH | sodium hydride |
| NaHMDS | sodium bis(trimethylsilyl)amide |
| THF | tetrahydrofuran |
| CPD# | compound number |

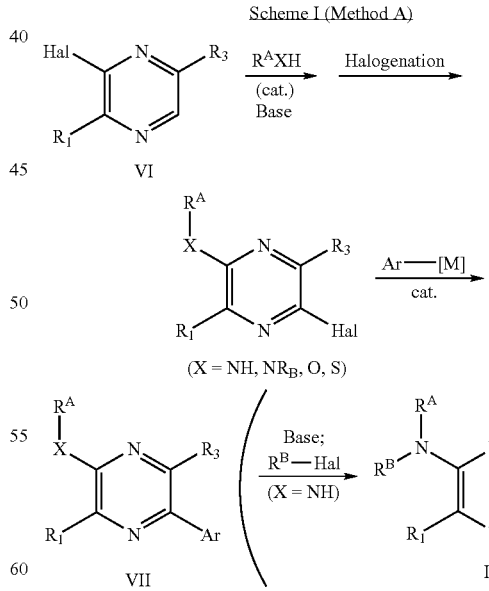

According to the general method A, wherein $R_1$ and $R_3$ are as defined for Formula I and Hal represents a halogen atom, suitably chloride or bromide, the halide in VI can be displaced by an amine or (thio)alkoxide nucleophile. Thus, aminopyrazine can be prepared from VI and an amine in the presence of a suitable transition metal catalyst such as but not limited to palladium(II) acetate or tris(dibenzylideneacetone)dipalladium(0), a ligand such as but not limited to 1,1'-bis(diphenylphosphine)ferrocene, 2,2'-bis(diphenylphosphine)-1,1'-binaphthyl, dicyclohexyl(2-biphenyl) phosphine, tricyclohexylphosphine, or tri-tert-butylphosphine, and a base such as sodium or potassium tert-butoxide in inert solvents such as but not limited to toluene, ethyleneglycol dimethyl ether, diglyme, DMF, or N-methylpyrrolidinone at temperatures ranging from ambient to 100° C. (Thio)alkoxypyrazines can be prepared by treating VI with a sodium or potassium salt of an alcohol or thiol in an inert solvent such as THF, DMF, N-methylpyrrolidinone, or methyl sulfoxide at ambient temperature or at elevated temperature up to the boiling point of the solvent employed. Halogenation may be accomplished by a variety of methods known in the art, including treatment with N-chlorosuccinimide, bromine, N-bromosuccinimide, pyridinium tribromide, triphenylphosphine dibromide, iodine, and N-iodosuccinimide in solvents such as but not limited to dichloromethane, acetic acid, or methyl sulfoxide. The bromopyrazine can be converted to arylpyrazine VII by a transition metal-catalyzed coupling reaction with a metalloaryl reagent (Ar-[M]). More commonly employed reagent/catalyst pairs include aryl boronic acid/palladium(0) (Suzuki reaction; N. Miyaura and A. Suzuki, Chemical Review 1995, 95, 2457), aryl trialkylstannane/palladium(0) (Stille reaction; T. N. Mitchell, Synthesis 1992, 803), arylzinc/palladium(0) and aryl Grignard/nickel(II). Palladium(0) represents a catalytic system made of a various combination of metal/ligand pair which includes, but not limited to, tetrakis(triphenylphosphine)palladium(0), palladium(II) acetate/tri(o-tolyl)phosphine, tris(dibenzylideneacetone)dipalladium (0)/tri-tert-butylphosphine and dichloro[1,1'-bis(diphenylphosphine)ferrocene]palladium(0). Nickel(II) represents a nickel-containing catalyst such as [1,2-bis(diphenylphosphino)ethane]dichloronickel(II) and [1,3-bis(diphenylphosphino)propane]dichloronickel(II). The arylpyrazine VII, when X is NH, may be further transformed to VIII by N-alkylation. The N—H group is deprotonated by a strong base such as but not limited to alkali metal hydride, alkali metal amide, or alkali metal alkoxide in inert solvents such as but not limited to THF, DMF, or methyl sulfoxide. Alkylation may be conducted using alkyl halide, suitably bromide or iodide, at temperatures ranging from 0° C. to 100° C.

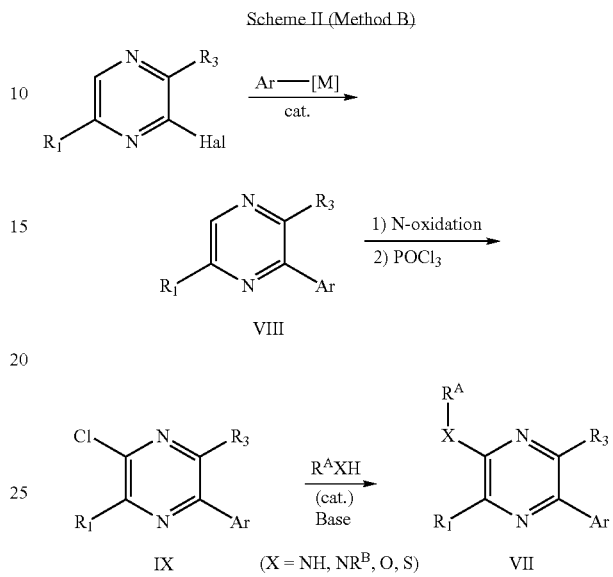

In an alternative way, compounds of Formula VII can be prepared as outlined in Scheme II. Transition metal-catalyzed coupling of the halo pyrazine VI as described in the Method A can provide the intermediate VIII. Oxidation of sterically less hindered nitrogen can be effected by using a variety of oxidizing agents known in the art, which includes m-chloroperoxybenzoic acid, trifluoroperacetic acid, hydrogen peroxide, and monoperoxyphthalic acid. The N-oxide can undergo rearrangement to give chloropyrazine IX upon the action of phosphorus oxychloride at temperatures ranging from ambient to 100° C. Displacement of the chloride with a nitrogen, oxygen, or sulfur nucleophile as described in the Method A can furnish the compounds of Formula VII.

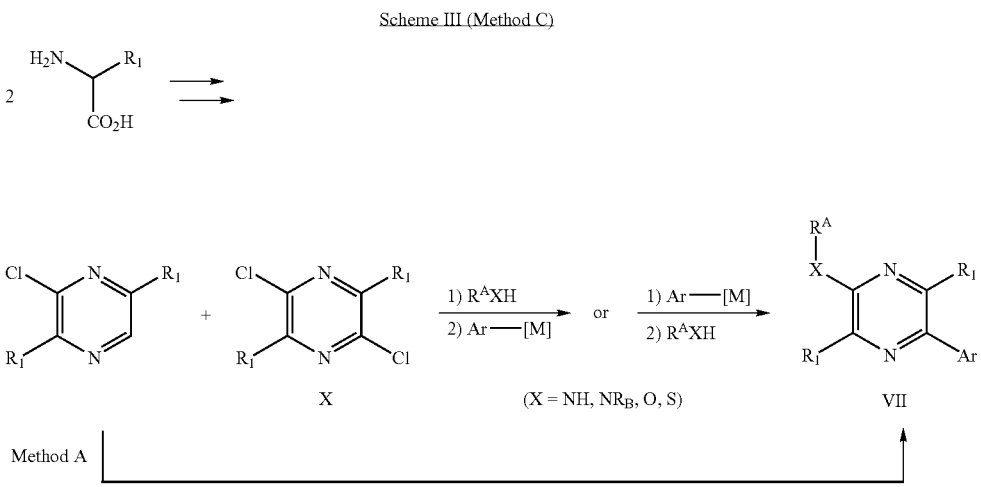

Yet another way of preparing compounds of Formula VII is illustrated in the Scheme III. Compounds of Formula X, 3,6-dialkyl-2,5-dichloropyrazines, can be prepared from 2-alkylglycine according to a known literature procedure (Ref: *Chemical and Pharmaceutical Bulletin of Japan* 1979, 27, 2027). Nucleophilic displacement of one chloride followed by Suzuki-type coupling at the other, as described in the Method A, can furnish the compounds of Formula VII.

VII by changing the order of the transformation sequence. Those who are skilled in the art will also recognize that one can further change the order of transformations to prepare the compounds of Formula VII by way of the intermediate XIII.

The preparation of the compounds of the present invention is illustrated further by the following examples, which

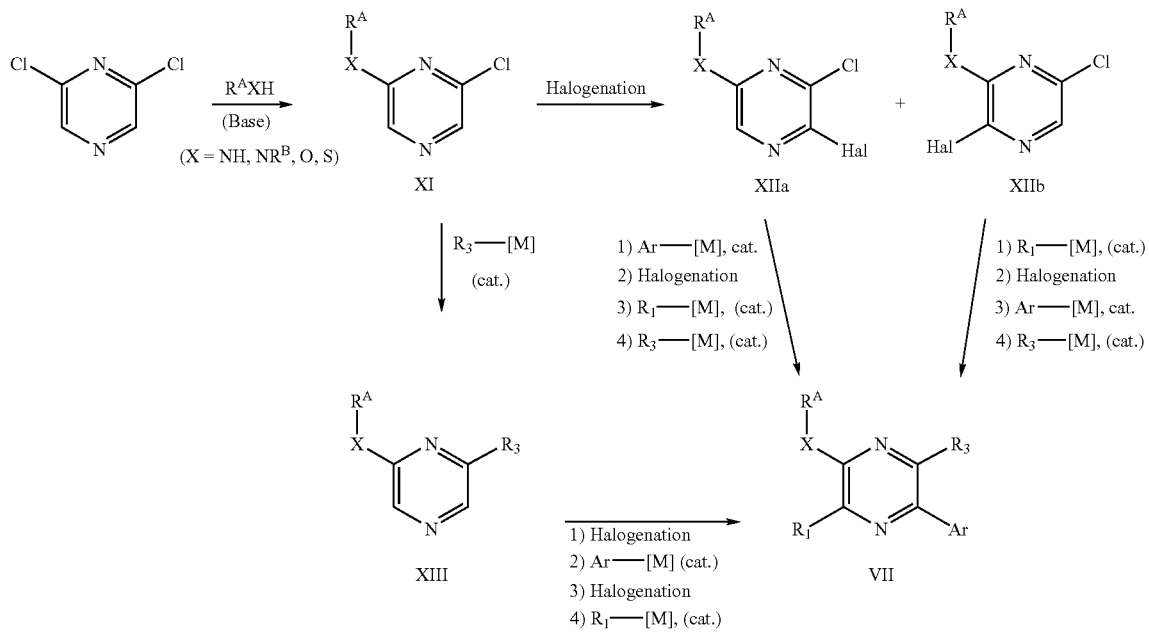

Still another way of preparing compounds of Formula VII is illustrated in Scheme IV. Commercially available 2,6-Dichloropyrazine can undergo monosubstitution with nitrogen, oxygen, or sulfur nucleophile to give XI. Thus, X may react with an amine in solvents such as but not limited to dichloromethane, acetonitrile, THF, DMF, N-methylpyrrolidinone, methyl sulfoxide, methanol, ethanol, and isopropanol at temperatures ranging from 0° C. to the boiling point of the solvent. In addition, X may react with a sodium or potassium (thio)alkoxide in inert solvents such as but not limited to THF, DMF, N-methylpyrrolidinone, or methyl sulfoxide at temperatures ranging from 0° C. to ambient temperature. Resulting monochloropyrazine XI can be halogenated by using the conditions described in the Method A to give a mixture of regioisomeric bromides XIIa and XIIb. Transition metal-catalyzed (hetero)aryl-aryl coupling of XIIa, as described in the Method A, followed by another halogenation can provide VII ($R_1$=Hal, $R_3$=Cl) which can be further converted to VII by displacing one or both of the halogen atoms, either sequentially or simultaneously, with a variety of nucleophiles ($R_1$-[M] and $R_3$-[M]), same or different, in the presence or absence of a transition metal catalyst. The aforementioned nucleophiles may include sodium or potassium (thio)alkoxide, alkylamine, and organometallic reagent such as but not limited to alkyl Grignard reagents, alkylboronic acids or its ester, or alkylstannanes. The aforementioned transition metal catalyst may represent palladium or nickel catalysts described in the Method A. The other regioisomeric bromide XIb can also be converted to are not to be construed as limiting the invention in scope or spirit to the specific procedures and compounds described in them.

Commercial reagents were used without further purification. Room or ambient temperature refers to 20 to 25° C. Concentration in vacuo implies the use of a rotary evaporator. TLC refers to thin layer chromatography. Proton nuclear magnetic resonance ($^1$H NMR) spectral data were obtained at 300 or 400 MHz. Mass spectral data were obtained either by CI or APCI methods.

Example 1

PREPARATION OF [N-(1-ETHYL)PROPYL]-5-(2,4-DIMETHOXYPHENYL)-3,6-DIMETHYLPYRAZINE-2-AMINE [Formula I: Ar=2,4-dimethoxyphenyl; $R_2$=—N-(1-ethyl)propyl; $R_1$=$R_3$=$CH_3$]

A. 1-ethylpropylamine (1.0 mmol) followed by sodium tert-butoxide (1.25 mmol) is added to a mixture of 2-chloro-3,6-dimethylpyrazine (0.83 mmol), tris(dibenzylideneacetone)dipalladium(0) (2 mol %), and BINAP (6 mol %) in ethyleneglycol dimethyl ether (2 mL) under nitrogen. The mixture is stirred at 70–80° C. for 2.5 hours, diluted with aqueous ammonium chloride, and extracted 1:1 hexane-$Et_2O$. Combined extracts are dried (sodium sulfate), filtered, concentrated, and chromatographed on silica gel (10:1 to 4:1 hexane-EtOAc eluent) to give the aminopyrazine.

B. A solution of N-(1-ethyl)propyl-3,6-dimethylpyrazine-2-amine (0.72 g; 3.7 mmol) in dichloromethane (20 mL) is cooled to 0° C. and N-bromosuccinimide (0.72 g; 4.1 mmol) is added in portions. After the addition, the mixture is further stirred for 1 hour while being allowed to warm to room temperature. The mixture is then concentrated to a small volume in vacuo, triturated with hexane, filtered, washed with hexane, and the filtrate is concentrated and chromatographed on silica gel to give the bromide (1.07 g).

C. A mixed solution of 5-bromo-[N-(1-ethyl)propyl]-3,6-dimethylpyrazine-2-amine (0.40 g; 1.47 mmol) and tetrakis(triphenylphosphine)palladium(0) (33 mg; 2 mol %) in ethyleneglycol dimethyl ether (8 mL) is stirred at room temperature for 15 minutes, after which 2,4-dimethoxybenzeneboronic acid (1.76 mmol) and an aqueous solution of sodium carbonate (1.0M, 4 mL) are added sequentially. The mixture is heated to 75 C. with stirring for 1.5 hours, then diluted with 0.1N sodium hydroxide and extracted twice with 1:1 hexane-ethyl ether. Combined extracts are dried (sodium sulfate), filtered, concentrated, and chromatographed on silica (4:1 to 1:1 hexane-EtOAc) to give the title compound (0.50 g): 1H NMR (CDCl3, 400 MHz) δ 0.95 (t, 6H), 1.6 (m, 4H), 2.2 (s, 3H), 2.4 (s, 3H), 3.75 (s, 3H), 3.85 (s, 3H), 3.95 (br d, 1H), 4.1 (br q, 1H), 6.5 (s, 1H), 6.55 (d, 1H) 7.2 (d, 1H); MS (CI) 330.

Example 2

Preparation of [N-(1-ethyl)propyl]-3,6-dimethyl-5-(2,4,6-trimethylphenyl) pyrazine-2-amine. [Formula I: Ar=2,4,6-trimethylphenyl; $R_2$=—N-(1-ethyl(propyl; $R_1$=$R_3$=$CH_3$]

[1,3-bis(diphenylphosphino)propane]dichloronickel(II) (40 mg) is added to a solution of 5-bromo-[N-(1-ethyl(propyl]-3,6-dimethylpyrazine-2-amine (200 mg) obtained as in Example 1B in THF (4 mL) at room temperature is added. After 10 minutes, 2,4,6-trimethylphenylmagnesium bromide (1.0M in THF, 4 mL) is added dropwise and slowly. The mixture is stirred at room temperature for 1 day, and then refluxed overnight. The resulting dark solution is poured into aqueous ammonium chloride and extracted twice with ether. Combined extracts are dried (sodium sulfate), filtered, concentrated, and chromatographed to give the desired product (87 mg): $^1$H NMR (CDCl$_3$, 400 MHz) δ 1.0 (t, 6H), 1.5–1.7 (m, 4H), 1.95 (s, 3H), 2.1 (s, 3H), 2.3 (s, 3H), 2.35 (s, 3H), 3.95 (br, 1H), 4.1 (br, 1H), 6.9 (s, 2H).

Example 3

Preparation of 3-ethyl-[N-(1-ethyl(propyl]-6-methyl-5-(2,4,6-trimethylphenyl) pyrazine-2-amine [Formula I: Ar=2,4,6-trimethylphenyl; $R_2$=—N(1-ethyl(propyl; $R_1$=$CH_2CH_3$; $R_3$=$CH_3$]

N-butyllithium (2.5M in hexane, 0.24 mL) is added to a solution of [N-(1-ethyl(propyl)-3,6-dimethyl-5-(2,4,6-trimethylphenyl)pyrazine-2-amine (74 mg; 0.24 mmol) in THF (2 mL) at 0° C. After 10 minutes at 0° C., iodomethane (0.020 mL) is added. The mixture is stirred at 0° C. for 10 minutes, before being poured into aqueous ammonium chloride and extracted with Et$_2$O. The extract is dried (sodium sulfate), filtered, concentrated and the residue is purified by preparative TLC (10% EtOAc in hexane, developed 3 times) to give the title compound (17 mg): $^1$H NMR (CDCl$_3$, 400 MHz) δ 1.0 (t, 6H), 1.25 (t. 3H), 1.5–1.7 (m, 4H), 1.95 (s, 3H), 2.05 (s, 3H), 2.3 (s, 3H), 2.65 (q, 2H), 4.05 (m, 2H), 6.9 (s, 2H).

Example 4

Preparation of 3,6-diethyl-5-(2,4-dimethoxyphenyl)-[N-(1-ethylpropyl)]pyrazine-2-amine [Formula I: Ar=2,4-dimethoxyphenyl; $R_2$=—N(1-ethyl(propyl; $R_1$=$R_3$=$CH_2CH_3$]

2-Chloro-3,6-diethylpyrazine (Chem. Pharm. Bull. Jap., 27, 2027 (1979)) is converted to the desired product following the procedures described in Example 1: $^1$H NMR (CDCl$_3$, 300 MHz) δ 0.95 (t, 6H), 1.15 (t, 3H), 1.25 (t, 3H), 1.5–1.7 (m, 4H), 2.45 (q, 2H), 2.65 (q, 2H), 3.75 (s, 3H), 3.85 (s, 3H), 4.0–4.2 (br, 2H), 6.5 (s, 1H), 6.55 (d, 1H), 7.2 (d, 1H).LC-MS: 358

Example 5

Preparation of 3,6-diethyl-5-(2,4-diethoxy)phenyl-[N-(1-ethylpropyl)]pyrazine-2-amine [Formula I: Ar=2,4-diethoxyphenyl; $R_2$=—N(1-ethyl(propyl; $R_1$=$R_3$=$CH_2CH_3$]

A: BBr$_3$ is added to a solution of 3,6-diethyl-5-(2,4-dimethoxyphenyl)-[N-(1-ethylpropyl)]pyrazine-2-amine (910 mg, 2.54 mmol). (obtained in example 4) in dichloromethane (1N, 6 ml) at −78° C. The mixture is stirred for 10 minutes, then gradually warmed to room temperature and stirred for 3 hours before being poured into ice-water and extracted with dichloromethane. The aqueous layer is basified with saturated NaHCO$_3$ and extracted with dichloromethane. The combined extracts are dried (sodium sulfate), filtered, concentrated and the residue is purified by column chromatography (20% EtOAc in hexane) to give 3,6-diethyl-5-(2,4-dihydroxyphenyl)-[N-(1-ethylpropyl)]pyrazine-2-amine as a yellow oil (590 mg, 71%): $^1$H NMR (CDCl$_3$, 400 MHz) δ 0.94 (t,6H), 1.30(t,3H), 1.36(t,3H), 1.57(m,2H), 1.67(m,2H), 2.62(q,2H), 2.86(q,2H), 4.15(m, 2H), 6.41(d,1H) 6.51(d,1H), 7.27(d,1H). LC-MS: 330 (M+1).

B: The above yellow oil (60 mg, 0.182 mmol) is dissolved in DMF (2 ml) and alkylated with iodoethane (0.072 ml, 0.9 mmol) in the presence of K$_2$CO$_3$ (125 mg) at 75° C. for 2 hours. The reaction mixture is then diluted with water and extracted with EtOAc. The extracts are dried (sodium sulfate), filtered, concentrated and the residue is purified by column (2.5% MeOH in dichloromethane) to give the title compound as an oil (49 mg, 70%): $^1$H NMR (CDCl$_3$, 400 MHz) δ 0.96 (t,6H), 1.13(t,3H), 1.27(m,6H), 1.42(t,3H), 1.57(m,2H), 1.67(m,2H), 2.47(m,2H), 2.66(q,2H), 3.95–4.15(m, 6H), 6.49(s,1H), 6.53(d,1H), 7.15(d,1H). LC-MS: 387 (M+1).

Example 6

Preparation of [N-(1-ethyl(propyl)-5-(2-methoxy-4,6-dimethylphenyl)-3,6-dimethylpyrazine-2-amine. [Formula I: Ar=2-methoxy4,6-dimethylphenyl; $R_2$=—N-(1-ethyl)propyl; $R_1$=$R_3$=$CH_3$]

A. 2-Methoxy-4,6-dimethylbenzeneboronic acid (1.08 g, 6.0 mmol) is added to a solution of 2-chloro-3,6-dimethylpyrazine (0.71 g, 5.0 mmol) and tetrakis(triphenylphosphine) palladium(0) (140 mg, 2.5 mol %) in ethylene glycol dimethyl ether (30 mL), followed by the addition of 1 M aqueous sodium carbonate solution (15 mL). The mixture is stirred at 70–75° C. overnight, allowed to cool, diluted by saturated aqueous sodium bicarbonate solution, and extracted twice with Et$_2$O. Combined extracts are dried (sodium sulfate), filtered, and concentrated in vacuo. The residue is purified by filtration through a short pad of silica gel to give 1.4 g of crude product.

B. The crude material obtained in step A is dissolved in dichloromethane (20 mL), cooled to 0° C. M-chloroperoxybenzoic acid (70%, 1.2 g) is added in portions. After 4 hours at ambient temperature, the mixture is diluted by n-hexane (20 mL) and washed with 1 M aqueous sodium hydroxide solution. The organic phase is separated, dried (sodium sulfate), filtered, concentrated in vacuo, and the residue is used directly in the next step without further purification.

C. The crude N-oxide is dissolved in phosphorus oxychloride (10 mL) and the solution is heated at 80° C. overnight. Evaporation of phosphorus oxychloride and aqueous work-up of the residue followed by chromatography on silica yields 2-aryl-5-chloro-3,6-dimethylpyrazine as a white solid (0.76 g).

D. A 0.2 M solution of tri-tert-butylphosphine in toluene (0.10 mL) is added to a solution of the chloropyrazine obtained in step C (260 mg, 0.94 mmol) and tris(dibenzylideneacetone)dipalladium(0) (11 mg) in toluene (10 mL). After 15 minutes at ambient temperature, 1-ethylpropylamine (0.14 mL) and potassium t-butoxide (1.0 M in THF, 1.4 mL) are added successively and the reaction mixture is heated at 80° C. for 4 hours. The mixture is allowed to cool to room temperature, diluted by ether, washed with aqueous ammonium chloride solution, dried (sodium sulfate), filtered, concentrated, and chromatographed on silica to give the desired product as a white solid (250 mg): $^1$H NMR (CDCl$_3$, 400 MHz) δ 0.95 (t, 6H), 1.5–1.7 (m, 4H), 2.0 (s, 3H), 2.1 (s, 3H), 2,4 (s,6H), 3.7 (s,3H), 3.95 (br d, 1H), 4.1 (br q, 1H), 6.6 (s, 1H), 6.7 (s, 1H).

Example 7

PREPARATION OF 5-(2-METHOXY-2,4-DIMETHYLPHENYL)-3, 6-dimethyl-2-(3-PENTYLOXY)PYRAZINE [Formula I: Ar=2-methoxy-4,6-dimethylphenyl; R$_2$=—OCH (CH$_2$CH$_3$)$_2$; R$_1$=R$_3$=CH$_3$]

3-Pentanol (0.1 mL) is added to a suspension of NaH (60% in mineral oil, 40 mg) in DMF (0.5 mL) The mixture is stirred at ambient temperature until hydrogen evolution ceased. An N-methylpyrrolidinone solution of 2-aryl-5-chloro-3,6-dimethylpyrazine (20 mg in 0.5 mL solvent) is added to the resulting alkoxide solution. After 1 hour at room temperature, the mixture is heated to 70° C. for another hour before being allowed to cool. The mixture is then diluted with aqueous ammonium chloride solution and extracted twice with Et$_2$O. Combined organics are dried (sodium sulfate), filtered, concentrated, and chromatographed on silica gel to give the title compound as a colorless oil (15 mg): $^1$H NMR (CDCl$_3$, 400 MHz) δ 1.0 (t, 6H), 1.75 (m, 4H), 1.95 (s, 3H), 2.15 (s, 3H), 2.35 (s, 3H), 2.45 (s, 3H), 3.7 (s, 3H), 5.1 (quint, 1H), 6.6 (s, 1H), 6.7 (s, 1H): MS (CI) 329, 259.

Example 8

PREPARATION OF [N-(1-ETHYL(PROPYL]-3,6-DIMETHYL-5-{2-[2-(4-MORPHOLINO)ETHYL]OXY-4,6-DIMETHYLPHENYL}PYRAZINE-2-AMINE [Formula I: Ar=2-[2(4-morpholino)ethyl]oxy-4,6-dimethylphenyl; R$_2$=—NHCH(CH$_2$CH$_3$)$_2$; R$_1$=R$_3$=CH$_3$]

A. A solution of 2-chloro-3,6-dimethyl-5-(2-methoxy-4, 6-dimethylphenyl)pyrazine (180 mg) in dichloromethane is cooled to 0° C. and boron tribromide (0.1 mL) is added slowly and dropwise. After the addition, the mixture is stirred at 0° C. for an additional 1.5 hours, diluted by Et$_2$O, washed with saturated aqueous sodium bicarbonate solution, dried (sodium sulfate), filtered, and concentrated in vacuo. The residue is used in the next step without further purification.

B. 4-(2-Chloroethyl)morpholine hydrochloride (200 mg) is added in one portion to a suspension of the crude phenol and potassium carbonate (400 mg) in DMF (4 mL) and the mixture is stirred at 60° C. for 4 hours. After further stirring at room temperature overnight, the mixture is poured into aqueous sodium bicarbonate and extracted twice with Et$_2$O-hexane. Combined extracts are dried (sodium sulfate), filtered, concentrated, and chromatographed on silica (eluent 5% triethylamine in 1:1 EtOAc-hexane) to give the product as a colorless oil (160 mg).

C. The chloropyrazine is converted to the corresponding aminopyrazine using methods: known in the art. $^1$H NMR (CDCl$_3$, 400 MHz) δ 0.95 (m, 6H), 1.6 (m, 4H), 2.0 (s, 3H), 2.1 (s, 3H), 2.3 (m, 4H), 2.35 (s, 6H), 2.6 (m, 2H), 3.6 (m, 2H), 3.9 (d, 1H), 4.0 (m, 2H), 4.05 (m, 1H), 6.55 (s, 1H), 6.7 (s, 1H); MS (CI) 427.

Example 9

PREPARATION OF 3-BROMO-6-CHLORO-5-(2,4-DICHLOROPHENYL)-[N-(1-ETHYL(PROPYL]PYRAZINE-2-AMINE [Formula I: Ar=2,4-dichlorophenyl; R$_1$=Br; R$_2$=—NHCH (CH$_2$CH$_3$)$_2$; R$_3$=Cl]

A. A solution of 2,6-dichloropyrazine (2.2 g) and 1-ethylpropylamine (5 mL) in EtOH (10 mL) is heated at 140° C. in a Teflon-sealed tube. The resulting solution is concentrated in vacuo, diluted by water, and extracted twice with hexane-ethyl ether. Combined extracts are dried (sodium sulfate), filtered, concentrated in vacuo, and the residue is filtered through a short pad of silica gel. The filtrate is concentrated to give 6-chloro-[N-(1-ethyl(propyl]pyrazine-2-amine as brownish oil that solidifies on standing (3.0 g).

B. A solution of the above amine (4.09 g; 20.48 mmol) in chloroform (80 ml) is cooled to 0° C. and N-bromosuccinimide (3.65 g; 20.48 mmol) is added in portions. The mixture is stirred at 0° C. for 30 minutes, poured into saturated aqueous NaHCO$_3$, and extracted with dichloromethane. The combined extracts are washed successively with water and brine, dried (sodium sulfate), and concentrated in vacuo. The residue is chromatographed on silica gel (6% EtOAc in hexane) to give the desired 3-bromopyrazine as a minor product (0.53 g; 9%) along with 6-chloro-5-bromo-[N-(1-ethyl(propyl]pyrazine-2-amine (4.37 g; 77%) as the major isomer.

C. 5-bromopyrazine obtained as above undergoes Suzuki coupling with 2,4-dichlorobenzeneboronic acid following the procedures in Example 1C to give 6-chloro-5-(2,4-dichlorophenyl)-[N-(1-ethyl)propyl]pyrazine-2-amine.

D. The aryl pyrazine is brominated again by using N-bromosuccinimide as described in Example 9B to give the desired product: $^1$H NMR (CDCl$_3$, 400 MHz) δ 0.97 (t, 6H), 1.58 (m,2H), 1.70 (m,2H), 4.00 (m,1H), 5.20 (d,1H), 7.30 (s, 2H), 7.50 (s,1H); MS(CI) 422.

Example 10

PREPARATION OF 6-CHLORO-5-(2,4-DICHLOROPHENYL)-[N-(1-ETHYL)PROPYL]-3-(2-PROPENYL)PYRAZINE-2-AMINE [Formula I: A=2,4-dichlorophenyl; R$_1$=CH$_2$CH=CH$_2$; R$_2$=—NHCH(CH$_2$CH$_3$)$_2$; R$_3$=Cl]

The bromopyrazine obtained in Example 9 is converted to the desired product by using allylboronic acid following the procedure set forth in Example 1C: $^1$H NMR (CDCl$_3$, 400 MHz) δ 0.93 (t, 6H), 1.50–1.71 (m, 4H), 3.50 (d, 2H), 4.05 (m, 1H), 4.55 (d, 1H), 5.22 (m, 2H), 5.92 (m, 1H), 7.34 (m, 2H), 7.48 (m, 1H); MS(CI) 384.

Example 11

PREPARATION OF 6-CHLORO-5-(2,4-DICHLOROPHENYL)-3-ETHYL-[N-(1-ETHYL)PROPYL]PYRAZINE-2-AMINE [Formula I: Ar=2,4-dichlorophenyl; R$_1$=CH$_2$CH$_3$; R$_2$=—NHCH(CH$_2$CH$_3$)$_2$; R$_3$=Cl]

The bromopyrazine obtained in Example 9 is converted to the desired product by using ethaneboronic acid following the same procedure as in Example 1C: $^1$H NMR (CDCl$_3$, 400 MHz) δ 0.96 (t, 6H), 1.30 (t, 3H), 1.56 (m, 2H), 1.70 (m, 2H), 2.65 (t, 2H), 4.08 (m, 1H), 4.35 (d, 1H), 7.32 (d, 1H), 7.33 (s, H), 7.48 (d, 1H); MS (CI) 372.

Example 12

PREPARATION OF 5-(2,4-DICHLOROPHENYL)-6-ETHYL-[N-(1-ETHYL)PROPYL]PYRAZINE-2-AMINE [Formula I: Ar=2,4-dichlorophenyl; R$_1$=H; R$_2$=—NHCH(CH$_2$CH$_{R3}$=CH$_2$CH$_3$]

A. 6-chloro-[N-(1-ethyl)propyl]pyrazine-2-amine obtained in Example 9A reacts with ethylmagnesium bromide as in Example 2 to give 6-ethyl-[N-(1-ethyl)propyl]pyrazine-2amine.

B. The 6-ethyl-[N-(1-ethyl)propyl]pyrazine-2-amine obtained in step A is brominated and coupled with 2,4-dichlorobenzeneboronic acid following the same procedure set forth in Examples 9B and 9C, respectively to give the title compound: $^1$H NMR (CDCl$_3$, 400 MHz) δ 0.97 (t, 6H), 1.13 (t,3H), 1.56 (m,2H), 1.65 (m,2H), 2.45 (m,2H), 3.72 (m,1H), 4.45 (d,1H), 7.25 (d, 1H), 7.30 (dd,1H), 7.48 (d,1H), 7.74 (s,1H); MS(CI) 338.

Example 13

PREPARATION OF 3-BROMO-5-(2,4-DICHLOROPHELYL)-6-ETHYL-[N-(1-ETHYL)PROPYL]PYRAZINE-2-AMINE [Formula I: Ar=2,4-dichlorophenyl; R$_1$=Br; R$_2$=—NHCH(CH$_2$CH$_3$)$_2$; R$_3$=CH$_2$CH$_3$]

The product of Example 12 is brominated via the procedure given in Example 9B to give the title compound: $^1$H NMR (CDCl$_3$, 400 MHz) δ 0.97 (t, 6H), 1.14 (t, 3H), 1.56 (m, 2H), 1.65 (m, 2H), 2.45 (m, 2H), 4.02 (m, 1H), 5.00 (d, 1H), 7.25 (d, 1H), 7.30 (dd, 1H), 7.46 (d, 1H); MS (CI) 416.

Example 14

PREPARATION OF 5-(2,4-DICHLOROPHENYL)-6-ETHYL-[N-(1-ETHYL)PROPYL]-3-METHOXYPYRAZINE-2-AMINE. [Formula I: Ar=2,4-dichlorophenyl; R$_1$=OCH$_3$; R$_2$50 —NHCH(CH$_2$CH$_3$)$_2$; R$_3$=CH$_2$CH$_3$]

3-Bromo-6-ethyl-5-(2,4-dichlorophenyl)-[N-(1-ethyl)propyl]pyrazine-2-amine, obtained by the method given in the previous example, is added to a 1 N solution of sodium methoxide in N-methylpyrrolidinone. The mixture is heated to 70° C. for 6 hours before being allowed to cool and then diluted with water and extracted with 20% EtOAc in hexane. The combined extracts are washed with water, dried (sodium sulfate), filtered, concentrated in vacuo, and chromatographed on silica gel to give the title compound: $^1$H NMR (CDCl$_3$, 400 MHz) δ 0.97 (t, 6H), 1.12 (t,3H), 1.56 (m, 2H), 1.65 (m, 2H), 2.40 (q, 2H), 3.92 (s, 3H), 4.04 (m, 1H), 4.82 (d, 1H), 7.28 (m, 2H), 7.48 (d, 1H); MS(CI) 368.

Example 15

PREPARATION OF 5-(2,4-DICHLOROPHENYL)-3-ETHYL-6-METHYL-[N-(1-ETHYL)PROPYL]PYRAZINE-2-AMINE [Formula I: Ar=2,4-dichlorophenyl; R$_1$=CH$_2$CH$_3$; R$_2$=—NHCH(CH$_{R3}$=CH$_3$]

A: [1,3-Bis(diphenylphosphino)propane]dichloronickel (II) (540 mg) is added to a solution of 2-(3-pentylamino)-6-chloropyrazine (4.26 g, 21.3 mmol) in THF (30 mL) at room temperature. After 10 minutes, methylmagnesium bromide (3.0M in diethyl ether, 15.7 mL) is added slowly and dropwise at 0° C. The mixture is stirred at room temperature for 1 hour. The resulting dark solution is poured into aqueous ammonium chloride and extracted twice with ether. Combined extracts are dried (sodium sulfate), filtered, concentrated, and chromatographed to give the desired product as a light brown oil (98%).

B: A solution of the above oil in chloroform (60 mL) is cooled to 0° C. and N-bromosuccinimide (3.8 g) is added in portions. After the addition, the mixture is further stirred for 1 hour while being allowed to warm to room temperature. The mixture is then concentrated to a small volume in vacuo, triturated with hexane, filtered, and washed with hexane. The filtrate is concentrated and chromatographed on silica gel (8% ethyl acetate in hexane elution) to give 5-bromo-[N-(1-ethyl)propyl]-6-methylpyrazine-2-amine (92%).

C. A mixed solution of the above bromide (1.2 g; 4.65 mmol) and tetrakis(triphenylphosphine)palladium(0) (4 mol %) in ethyleneglycol dimethyl ether (60 mL) is stirred at room temperature for 15 minutes. 2,4-Dichlorobenzeneboronic acid (1.3 g, 7 mmol) and an aqueous solution of sodium carbonate (1.0M, 12 mL) are then added sequentially. The mixture is heated to 75° C. with stirring for 1.5 hour, then diluted with 0.1N sodium hydroxide and extracted twice with 1:1 hexane-ethyl ether. Combined extracts are dried (sodium sulfate), filtered, concentrated, and chromatographed on silica (4:1 hexane-EtOAc) to give 5-(2,4-dichlorophenyl)-6-methyl-[N-(1-ethyl)propyl]pyrazine-2-amine as a yellow oil (1.46 g, 97%): 1H NMR (CDCl$_3$, 400 MHz) δ 0.97 (t,6H), 1.54(m,2H), 1.67(m,2H), 2.22(s,3H), 3.65(m, 1H), 4.50(br, 1H), 7.27(d,1H), 7.31(dd,1H), 7.48(d,1H), 7.76(s, 1H).

D: A solution of the above oil (1.27 g, 3.92 mmol) in chloroform (40 mL) is cooled to 0° C. and N-bromosuccinimide (770 mg) is added in portions. After the addition, the mixture is further stirred for 1 hour while being allowed to warm to room temperature. The mixture is then concentrated to a small volume in vacuo, triturated with hexane, filtered, and washed with hexane. The filtrate is concentrated and chromatographed on silica gel (3% ethyl acetate in hexane elution) to give 3-bromo-5-(2,4-dichlorophenyl)-6-methyl-[N-(1-ethyl)propyl]pyrazine-2-amine (1.56 g, 98%).

E: A mixed solution of 3-bromo-5-(2,4-dichlorophenyl)-6-methyl-[N-(1-ethyl)propyl]pyrazine-2-amine (960 mg; 2.38 mmol) and tetrakis(triphenylphosphine) palladium(0)(4 mol %) in ethyleneglycol dimethyl ether (25 mL) is stirred at room temperature for 15 minutes. Ethaneboronic acid (1.0 g) and an aqueous solution of sodium carbonate (1.0M, 8.5 mL) are then added sequentially. The mixture is heated to 75° C. with stirring for 12 hours, then diluted with 0.1N sodium hydroxide and extracted twice with 1:1 hexane-ethyl ether. Combined extracts are dried (sodium sulfate), filtered, concentrated, and chromatographed on silica (10:1 hexane-EtOAc) to give the title compound as a yellow oil (460 mg, 55%): 1H NMR (CDCl3, 400 MHz) δ 0.95 (t, 6H), 1.28(t, 3H), 1.54(m, 2H), 1.67(m, 2H), 2.20(s, 3H), 2.65(q, 2H), 4.13(m, 2H), 7.27(d, 1H), 7.31(d, 1H), 7.48(s, 1H).LC-MS: 352 (M+1).

Example 16

PREPARATION OF 5-(2,4-DICHLOROPHENYL)-3-ETHOXY-6-ETHYL-[N-(1-ETHYL)PROPYL]PYRAZINE-2-AMINE [Formula I: Ar=2,4-dichlorophenyl; $R_1$=OCH$_2$CH$_3$; $R_2$=—NHCH(CH$_2$CH$_3$)$_{R3}$=CH$_{CH3}$]

The same reaction as in Example 15 with sodium ethoxide gives the title compound: $^1$H NMR (CDCl$_3$, 400 MHz)) δ 0.95 (t, 6H), 1.10 (t, 3H), 1.37 (t, 3H), 1.55 (m, 2H), 1.68 (m, 2H), 2.36 (m, 2H), 4.05 (m, 1H), 4.33 (q, 2H), 4.81 (d, 1H), 7.24 (d, 1H), 7.26 (dd, 1H), 7.46 (d, 1H); MS(CI) 382.

Example 17

5-(2,4-DICHLOROPHENYL)-6-ETHYL-[N-(1-ETHYL)PROPYL]-3-METHYLPYRAZINE-2-AMINE [Formula I: Ar=2,4-dichlorophenyl; $R_1$=CH$_3$; $R_2$=—NHCH(CH$_2$CH$_3$)$_2$; $R_3$=CH$_2$CH$_3$]

3-Bromo-5-(2,4-dichlorophenyl)-6-ethyl-[N-(1-ethyl) propyl] pyrazine-2-amine obtained from Example 9 is converted to the title compound by using methylmagnesium bromide according to the procedure set forth in Example 2: $^1$H NMR (CDCl$_3$, 400 MHz) δ 0.97 (t, 6H), 1.12 (t, 3H), 1.56 (m, 2H), 1.65 (m, 2H), 2.35 (s, 3H), 2.42 (m, 2H), 4.04 (m, 2H), 7.25 (d, 1H), 7.29 (dd, 1H), 7.46 (d, 1H); MS (CI) 352.

Example 18

PREPARATION OF 3-BROMO-5-(2,4-DICHLOROPHENYL)-[N-(1-ETHYL)PROPYL]-6-METHYLPYRAZINE-2-AMINE [Formula I: Ar=2,4-dichlorophenyl; $R_1$=Br; $R_2$=—NHCH(CH$_2$CH$_3$)$_2$; $R_3$=OCH$_3$]

6-Chloro-5-(2,4-dichlorophenyl)-[N-(1-ethyl)propyl] pyrazine-2-amine obtained in Example 9C is converted to 5-(2,4-dichlorophenyl)-6-methoxy-[N-(1-ethyl)propyl] pyrazine-2-amine according to the procedure given in Example 16. The resulting amine is converted to the title compound via the procedure given in Example 9: $^1$H NMR (CDCl$_3$, 400 MHz) δ 0.97 (t, 6H), 1.60 (m, 2H), 1.70 (m, 2H), 3.89 (s, 3H), 3.92 (m, 1H), 4.98 (d, 1H) 7.27 (dd, 1H), 7.34 (d, 1H), 7.44 (d, 1H); MS (CI) 418.

Example 19

5-(2,4-DICHLOROPHENYL)-[N-(1-ETHYL)PROPYL]-3,6-DIMETHOXYPYRAZINE-2-AMINE [Formula I: Ar=2,4-dichlorophenyl; $R_1$=$R_3$=OCH$_3$; $R_2$=—NHCH(CH$_2$CH$_3$)$_2$]

Sodium methoxide (3,0 mmole) is added to a solution of 3bromo-5(2,4-dichlorophenyl)-[N-(1-ethyl)propyl]-6-methoxypyrazine-2-amine (0.8 mmole) in 1-methyl-2pyrrolidinone (5 ml). The resulting mixture is then heated to 80° C. for three days. The mixture is diluted with water and extracted with ethyl acetate. The combined extracts are washed thoroughly with water, and then brine, and dried. After removing the solvent, the crude is purified by silica gel column (eluted with 3% EtOAc in hexane) to give the title compound as a light yellow oil (65% yield). $^1$H NMR (CDCl$_3$, 400 MHz) δ 0.97 (t, 6H), 1.56 (m, 2H), 1.68 (m, 2H), 3.86 (s, 3H), 3.94 (s,3H), 3.95(m, 1H), 4.82 (d, 1H), 7.27 (dd, 1H), 7.40 (d, 1H), 7.44 (d, 1H). MS (CI) 370.

Example 20

PREPARATION OF 3-ETHYL-5-(2,4-DICHLOROPHENYL)-[N-(1-ETHYL)PROPYL]-6-METHYLPYRAZINE-2-AMINE [Formula I: Ar=2,4-dichlorophenyl; $R_1$=CH$_2$CH$_3$; $R_3$=OCH$_3$, $R_2$=—NHCH(CH$_2$CH$_3$)$_2$]

A: A solution of sodium methoxide in methanol (5.0M, 10 ml) I s added to a solution of 2-(3-pentylamino)-6-chloropyrazine (3.3 g, 16.5 mmol) in 1-methyl-2-pyrrolidinone (15 mL) at room temperature. The resulting solution is heated to 50° C. for 20 hours then evaporated and poured into water and extracted twice with ethyl acetate/hexane (1:1). Combined extracts are dried (sodium sulfate), filtered, concentrated, and chromatographed to give N-(1-ethyl)propyl-6-methoxypyrazine-2-amine as a light yellow solid (98%).

B: A solution of the above solid in chloroform (60 mL) is cooled to 0° C. and N-bromosuccinimide (3.0 g) is added in portions. After the addition, the mixture is further stirred for 1 hour while being allowed to warm to room temperature. The mixture is then diluted with dichloromethane, washed with saturated NaHCO$_3$, water, and brine, and then dried and filtered. The filtrate is concentrated and chromatographed on silica gel (dichloromethane/hexane 1:1 elution) to give 3-bromo-[N-(1-ethyl)propyl]-6-methoxypyrazine-2-amine as a yellow oil (35%). $^1$H NMR (CDCl$_3$, 400 MHz) δ 0.93 (t, 6H), 1.56 (m, 2H), 1.66 (m, 2H), 3.87 (s, 3H), 3.92(m, 1H), 4.85 (d, 1H), 7.18 (s, 1H).

C: To a solution of above 3-bromo-[N-(1-ethyl)propyl]-6-methoxypyrazine-2-amine (1.27 g, 4.63 mmol) in THF (30 mL) is added [1,3-bis(diphenylphosphino)propane] dichloronickel(II) (125 mg). After 10 minutes, ethylmagnesium bromide (1.0M in THF, 9.7 mL) is added slowly and dropwise at 0° C. The mixture is stirred at room temperature for 1 hour. The resulting dark solution is poured into aqueous ammonium chloride and extracted twice with ether. Combined extracts are dried (sodium sulfate), filtered, concentrated, and chromatographed (2.5% MeOH/CH$_2$Cl$_2$) to give the desired product 3-ethyl-[N-(1-ethyl)propyl]-6-methoxypyrazine-2-amine as a light yellow oil (55%).

D: A solution of the above oil (0.55 g, 2.46 mmol) in chloroform (10 mL) is cooled to 0° C. and N-bromosuccinimide (445 mg) is added in portions. After the addition, the mixture is r stirred for an additional 30 minutes while being allowed to warm to room temperature. The mixture is then concentrated to dryness in vacuo, and chromatographed on silica gel (5% ethyl acetate in hexane elution) to give 5-bromo-3-ethyl-6-methoxy-[N-(1-ethyl)propyl]pyrazine-2-amine (85%).

E. A mixed solution of the above bromide (100 mg; 0.33 mmol) and tetrakis (triphenylphosphine)palladium(0) (5 mol %) in ethyleneglycol dimethyl ether (3 mL) is stirred at room temperature for 15 minutes. 2,4-Dichlorobenzeneboronic acid (95 mg) and an aqueous solution of sodium carbonate (1.0M, 0.75 mL) are then added sequentially. The mixture is heated to 75° C. with stirring for 15 hoys, then diluted with water and extracted twice with 1:1 hexane-ethyl ether. Combined extracts are dried (sodium sulfate), filtered, concentrated, and chromatographed on silica (6% ethyl acetate in hexane) to give the title compound as a yellow oil (121 mg, 99%): 1H NMR (CDCl3, 400 MHz) δ 0.97 (t,6H), 1.27(t,3H), 1.56(m,2H), 1.70(m,2H), 2.62(q,2H), 3.85(s, 3H), 4.00(m, 1H) 4.18 (d,1H), 7.28(d,1H), 7.38(d,1H), 7.44 (s,1H). MS: 368.

Example 21

Preparation of 3-Ethyl-5-(2-methoxy-4-trifluoromethoxyphenyl)-[N(1-ethyl)propyl]-6-methoxypyrazine-2-amine

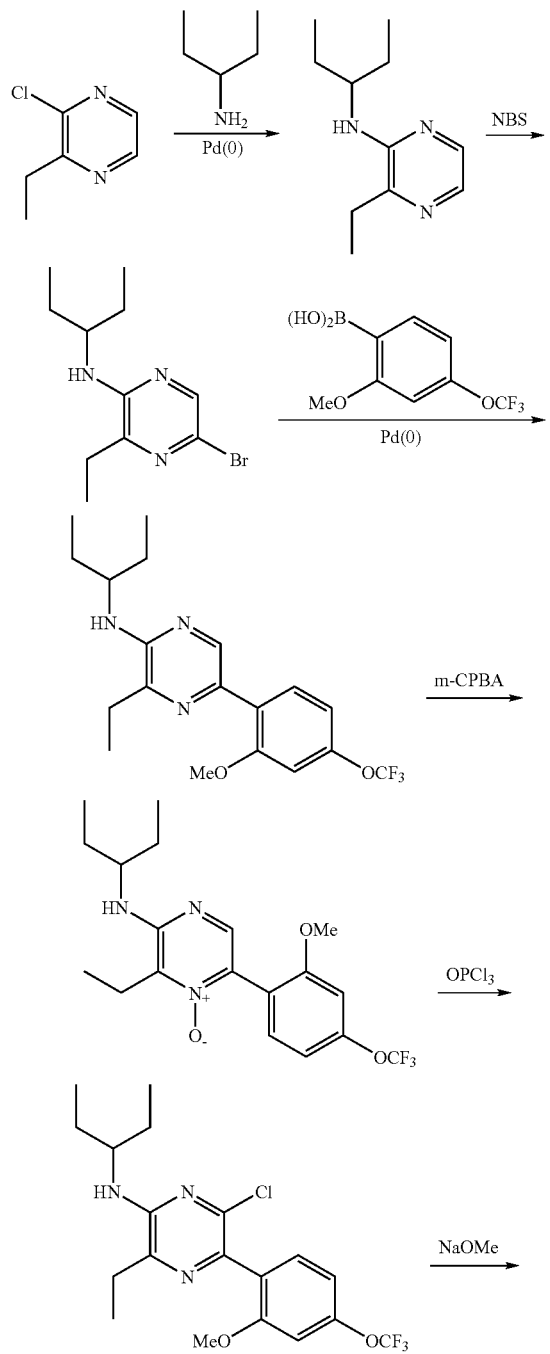

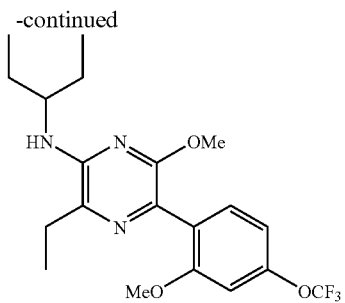

A. (1-Ethyl-propyl)-(3-ethyl-pyrazin-2-yl)-amine. In a pressure tube, 2-chloro-3-ethyl-pyrazine (1.4 g, 10 mmol), Pd$_2$(dba)$_3$ (229 mg, 0.25 mmol) and P(t-Bu)$_3$ (100 microliters, 0.4 mmol) are dissolved in toluene (15 mL) and stirred at room temperature for 30 minutes. 1-Ethyl-propylamine (1.75 mL, 15 mmol) and KOt-Bu (1M in THF, 15 mmol, 15 mL) are added, and the dark solution is stirred at 55° C. (oil bath temperature) for 90 minutes. The reaction mixture is allowed to reach room temperature, diluted with ethyl ether (100 mL) and washed with brine (3×100 mL). After drying with MgSO$_4$, the solvents are removed under reduced pressure. A dark oil is obtained. Flash chromatography (100% hexanes to 20% ethyl acetate in hexanes) produces the desired product (710 mg, 37%). H-1 NMR (CDCl$_3$, 300 MHz): 7.84 (1H, d, J=8.1 Hz), 7.68 (1H, d, J=9 Hz), 4.15 (br, 1H), 4.05 (quint, 1H), 2.6 (2H, q, J=7.4 Hz), 1.4–1.6 (m, 4H), 1.32 (t, 3H, J=7.4 Hz), 0.95 (t, 6H, J=7.4 Hz). MS: 194 (M+1, positive mode) and 192 (M−1, negative mode).

B. (5-Bromo-3-ethyl-pyrazin-2-yl)-(1-ethyl-propyl)-amine. The product from step A (650 mg, 3.4 mmol) is dissolved in chloroform (20 mL) and treated at room temperature with N-bromosuccinimide (600 mg, 3.5 mmol). After 5 minutes the mixture is diluted with chloroform (100 mL) and the organic solution washed with brine (3×100 mL), dried (MgSO$_4$), filtered, and the solvent removed under reduced pressure to produce 5-bromo-3-ethyl-pyrazin-2-yl)-(1-ethyl-propyl)-amine (700 mg, 77%). H-1 NMR (CDCl$_3$, 400 MHz): 7.94 (1H, s), 4.1 (br, 1H), 3.95 (quint, 1H), 2.60 (2H, q, J=7.4 Hz), 1.4–1.6 (m, 4H), 1.32 (t, 3H, J=7.4 Hz), 0.95 (t, 6H, J=7.4 Hz). MS: 274.1 (M+1, positive mode) and 270.3 (M−1, negative mode).

C. [3-Ethyl-5-(2-methoxy-4-trifluoromethoxy-phenyl)-pyrazin-2-yl]-(1-ethyl-propyl)amine. In a pressure tube, a mixture of the product from step B (700 mg, 2.6 mmol), 2methoxy-4-trifluoromethoxyboronic acid (1.0 g, 4.2 mmol) and Pd(PPh$_3$)$_4$ (100 mg) in toluene (10 mL), ethanol (0.5 mL), and aqueous K$_2$CO$_3$ (2M, 5 mL) is heated in oil bath at 80° C. for 16 hours. The mixture is diluted with ethyl acetate, and the organic fraction washed with NaOH (2M, 50 mL) and brine (3×50 mL), dried (MgSO$_4$) filtered, and the solvent removed under reduced pressure. Flash chromatography of the residue (100% hexanes to 4% ethyl acetate in hexanes) provides the desired product as an oil (850 mg, 85%). $^1$H NMR (CDCl$_3$, 300 MHz): 8.53 (1H, s), 7.91 (1H, d, J=8.8 Hz), 6.93 (1H, d, J=8.8 Hz), 6.80 (s, 1H), 4.18 (1H, d, J=8.2 Hz), 4.10 (quint, 1H, J=5.8 Hz), 3.88 (3H, s), 2.6 (2H, q, J=7.4 Hz), 1.4–1.6 (m, 4H), 1.37 (t, 3H, J=7.4 Hz), 0.95 (t, 6H, J=7.4 Hz). MS: 384.3 (M+1, positive mode) and 382.2 (M−1, negative mode).

D. [3-Ethyl-5-(2-methoxy-4-trifluoromethoxy-phenyl)-4-oxy-pyrazin-2-yl]-(1-ethyl-propyl)-amine. The aminopyrazine obtained in step C (370 mg, 0.97 mmol) is dissolved in dichloromethane (15 mL) and treated with solid m-chloroperoxybenzoic acid (374 mg, 1.3 eq) at room temperature. After 3 hour the reaction mixture is diluted with dichloromethane (50 mL) and washed with NaOH 2M (25 mL) and brine (3×50 mL). The organic solution is dried (MgSO$_4$), filtered and the solvent evaporated under reduced pressure. The residue is purified by preparative thin layer chromatography, eluting with 30% ethyl acetate in hexanes), to furnish the desired product (55 mg, 14%). NMR (CDCl$_3$, 400 MHz) H-1: 7.86 (1H, s), 7.38 (1H, d, J=8.4 Hz), 6.89 (1H, d, J=7.2 Hz), 6.81 (s, 1H), 4.21 (1H, d, J=8.0 Hz), 4.08 (quint, 1H, J=6.0 Hz), 3.81 (3H, s), 2.9 (2H, q, J=7.6 Hz), 1.5–1.75 (m, 4H), 1.23 (t, 3H, J=7.2 Hz), 0.96 (t, 6H, J=7.6 Hz). C-13: 158.96, 154.43, 150.64, 142.56, 132.86, 132.47, 131.32, 119.15, 112.22, 104.58, 104.58, 56.01, 53.35, 26.96, 17.89, 10.04, 8.86. F-19 NMR: −58.04 (s). (MS: 400.3 (M+1, positive mode) and 398.3 (M−1, negative mode).

E. [6-Chloro-3-ethyl-5-(2-methoxy-4-trifluoromethoxyphenyl)-pyrazin-2-yl]-(1-ethyl-propyl)-amine. The N-oxide from step D (40 mg, 0.11 mmol) is dissolved in POCl$_3$ (1.5 mL) and heated at 80° C. for 16 hours. After cooling to room temperature, the reaction mixture is diluted with ethyl ether (100 mL), washed with NaOH (2M, 50 mL) and brine (3×50 mL), dried (MgSO4), filtered, and the solvent evaporated under reduced pressure to afford the desired chloropyrazine (40 mg, 96%). NMR (CDCl$_3$, 400 MHz) H-1: 7.32 (1H, d, J=8.4 Hz), 6.89 (1H, d, J=7.2 Hz), 6.80 (s, 1H), 4.26 (1H, d, J=8.4 Hz), 4.07 (quint, 1H, J=5.6 Hz), 3.82 (3H, s), 2.64 (2H, q, J=7.6 Hz), 1.5–1.75 (m, 4H), 1.29 (t, 3H, J=7.6 Hz), 0.96 (t, 6H, J=7.2 hHz). C-13: 158.20, 150.91, 150.14, 143.80, 140.95, 134.30, 131.94, 126.07, 112.44, 104.58, 55.78, 53.01, 26.81, 25.75, 10.80, 10.02. F-19 NMR: −58.03 (s). (MS: 418.2 (M+1, positive mode) and 416.2 (M−1, negative mode).

F. [3-Ethyl-6-methoxy-5-(2-methoxy-4-trifluoromethoxy-phenyl)-pyrazin-2-yl]-(1-ethyl-propyl)-amine. In a pressure tube, the chloropyrazine from step E (30 mg) is dissolved in DMF (2 mL) and treated with sodium methoxide (100 mg) at 80° C. for 120 hours. The reaction mixture is diluted with ethyl ether (50 mL) and washed with brine. The residue is purified by preparative thin layer chromatography (15% ethyl acetate in hexanes to produce [3-ethyl-6-methoxy-5-(2-methoxy-4-trifluoromethoxy-phenyl)-pyrazin-2-yl]-(1-ethyl-propyl)-amine (10 mg, 33%).

Example 22

6-Chloro-[N-(1-ethyl)propyl]-3-methoxy-5-(2,4-dichlorophenyl) pyrazine-2-amine [Formula I: Ar=2,4-dichlorophenyl; R$_1$=OCH$_3$; R$_2$=NHCH(CH$_2$CH$_3$)$_2$; R$_3$=Cl]

A. A solution in DMF (2 mL) of 3-bromo-6chloro-[N-(1-ethyl)propyl]pyrazine-2-amine (0.50 g; 1.8 mmol) obtained as a minor product in Example 9B is added into a solution of sodium methoxide (freshly prepared from 90 mg of sodium metal in methanol; 3.9 mmol) in DMF (3 mL). The mixture is stirred at room temperature overnight, then poured into aqueous ammonium chloride solution and extracted twice with hexane-ethyl ether. Combined extracts are dried (sodium sulfate), filtered, concentrated in vacuo, and chromatographed on silica gel to give 6-chloro-3-methoxy-[N-(1-ethyl)propyl]pyrazine-2-amine (410 mg).

B. The above material is brominated according to via procedure used in Example 13 and converted to the title compound by the Suzuki coupling procedure disclosed in Example 1C: $^1$H NMR (CDCl$_3$, 400 MHz) δ 0.95 (t, 6H), 1.5–1.7 (m, 4H), 2.15 (s, 3H) 3.85 (s, 3H), 3.95 (s, 3H), 4.0 (m, 1H), 4.8 (br d, 1H), 6.55 (s, 1H), 6.55 (d, 1H), 7.3 (d, 1H).

Example 23

Preparation of 5-(2,4-dichlorophenyl)-[N-(1-ethyl)propyl]-3-methoxy-6-methylpyrazine-2-amine [Formula I: Ar=2,4-dichlorophenyl; R$_1$=OCH$_3$; R$_2$=—NHCH(CH$_2$CH$_3$)$_2$; R$_3$=CH$_3$]

A. 6-chloro-3-methoxy-[N-(1-ethyl)propyl]pyrazine-2-amine obtained in Example 22A is converted to the 6-methyl derivative and further brominated according to the same procedure used in Example 17.

B. The 5-bromopyrazine obtained in step A is converted to the title compound by the procedure used in Example 1C: $^1$H NMR (CDCl$_3$, 400 MHz) δ 0.95 (t, 6H), 1.5–1.7 (m, 4H) 2.15 (s, 3H), 3.9 (s, 3H), 4.05 (m, 1H), 4.8 (br d, 1H), 7.3 (s, 2H), 7.45 (s, 1H); MS (CI) 356.

Example 24

Preparation of {4-[6-ethyl-5-(ethylpropoxy)-3-methoxypyrazin-2-yl]-3-methoxyphenoxy}trifluoromethane

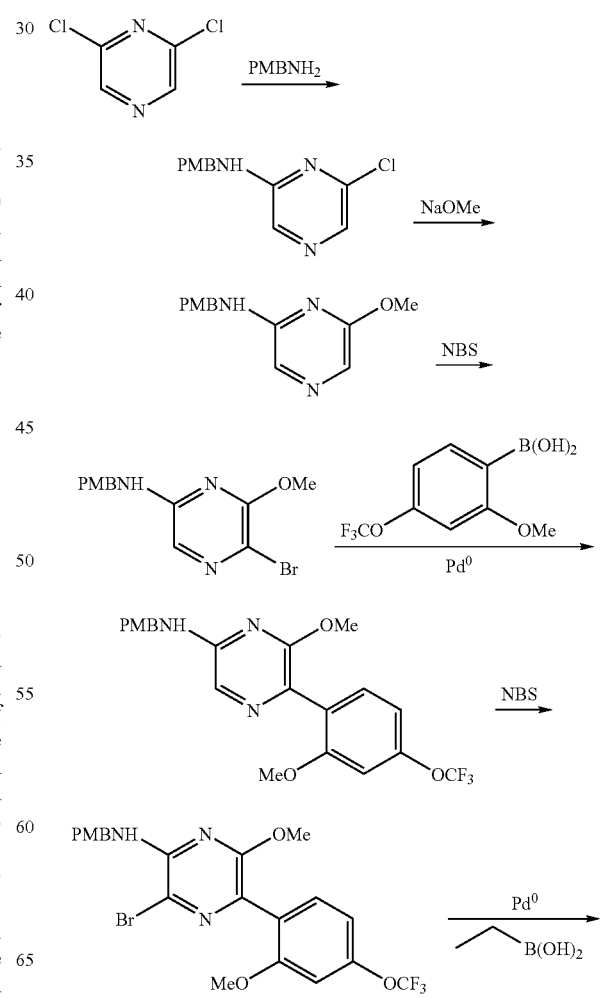

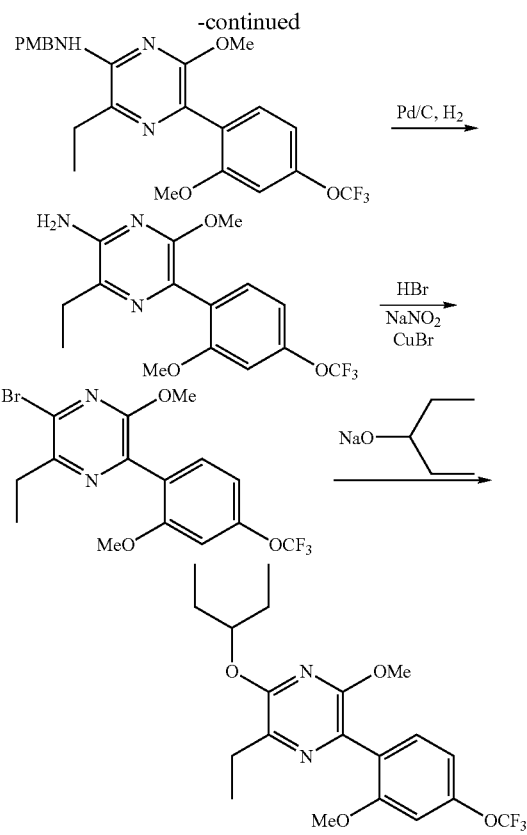

A. 4-methoxybenzylamine (68.6 g, 0.5 mol) is added to a stirred solution of 2,6-dichloropyrazine (25 g, 0.167 mol) and ethanol (120 mL) in a sealed tube. The mixture is heated to 115 C for 12 hours and cooled. The white solid is removed by filtration and the filtrate evaporated. The residue is dissolved in ethyl acetate and washed successively with 2M sodium hydroxide, water and aqueous sodium chloride. The organics are dried (magnesium sulfate), filtered, and evaporated to give (6-chloropyrazin-2-yl)[(4-methoxyphenyl)methyl]amine (35.5 g), a white solid.

B. Sodium methoxide (7.50 g, 125.0 mmol) is added to a stirred solution of (6-chloropyrazin-2-yl)[(4-methoxyphenyl)methyl]amine (5.0 g, 20.0 mmol) in DMF (30 mL). The mixture is heated at reflux for 12 hours, cooled and partitioned between ethyl acetate (100 mL) and water (100 mL). The layers are separated and the organic layer washed with water (3×100 mL). The combined extracts are dried (magnesium sulfate), filtered, and evaporated to give [(4-methoxyphenyl)methyl](6-methoxypyrain-2-yl)amine (4.65 g), a yellow solid.

C. A solution of [(4-methoxyphenyl)methyl](6-methoxypyrain-2-yl)amine (2.45 g, 10.0 mmol) in chloroform (50 mL) is cooled to 0 C and N-bromosuccinimide (1.8 g, 10.0 mmol) is added in portions. After the addition, the mixture is further stirred for 1 hour while being allowed to warm to room temperature. The mixture is washed with saturated aqueous sodium bicarbonate, aqueous sodium chloride, dried (magnesium sulfate), filtered and evaporated. The residue is purified by flash chromatography, eluting with 20% ether in hexanes to give (5-bromo-6-methoxypyrazin-2-yl)[(4-methoxyphenyl)methyl]amine (1.1 g).

D. Tetrakis(triphenylphosphine)palladium(0) (100 mg) and potassium carbonate (2.0 M, 2.0 mL) are added to a stirred solution of (5-bromo-6-methoxypyrazin-2-yl)[(4-methoxyphenyl)methyl]amine (0.80 g, 2.50 mmol) and 2-methoxy-4-trifluoromethoxy benzeneboronic acid (1.75 g, 7.5 mmol) in toluene (25 mL). The mixture is heated to 85 C for 8 hours, cooled to room temperature, diluted with 2.0 M sodium hydroxide and extracted twice with 1:1 hexane-ethyl ether. The combined extracts are dried (sodium sulfate), filtered and concentrated. The residue is purified by flash chromatography, eluting with 60% hexanes in ether to give {6-methoxy-5-[2-methoxy-4-(trifluoromethoxy)phenyl]pyrazin-2yl}[(4-methoxyphenyl)methyl]amine (967 mg).

E. A solution of {6-methoxy-5-[2-methoxy-4-(trifluoromethoxy)phenyl]pyrazin-2yl}[(4-methoxyphenyl)methyl]amine (870 mg, 2.0 mmol) in chloroform (10 mL) is cooled to 0 C and N-bromosuccinimide (356 mg, 2.0 mmol) is added in portions. After the addition, the mixture is further stirred for 1 hour while being allowed to warm to room temperature. The mixture is washed with saturated aqueous sodium bicarbonate, aqueous sodium chloride, dried (magnesium sulfate), filtered, and evaporated to give {3-bromo-6-methoxy-5-[2methoxy-4-(trifluoromethoxy)phenyl]pyrazin-2-yl} [(4-methoxyphenyl)methyl]amine (920 mg), a yellow solid.

F. Tetrakis(triphenylphosphine)palladium(0) (50 mg) and potassium carbonate (2.0 M, 1.0 mL) are added to a stirred solution of {3-bromo-6-methoxy-5-[2-methoxy-4-(trifluoromethoxy)phenyl]pyrazin-2-yl}[(4-methoxyphenyl)methyl]amine (514 mg, 1.0 mmol) and ethylboronic acid (219 mg, 3.0 mmol) in toluene (8 mL). The mixture is heated to 85 C for 8 hours, cooled to room temperature, diluted with 2.0 M sodium hydroxide and extracted twice with 1:1 hexane-ethyl ether. The combined extracts are dried (sodium sulfate), filtered and concentrated. The residue is purified by flash chromatography, eluting with 20% ether in hexanes to give {3-ethyl-6-methoxy-5-[2-methoxy-4-(trifluoromethoxy)phenyl]pyrazin-2-yl}[(4-methoxyphenyl)methyl]amine (430 mg).

G. 1M hydrochloric acid in ether (2 mL) and 10% palladium on carbon (40 mg) are added to {3-ethyl-6-methoxy-5-[2-methoxy-4-(trifluoromethoxy)phenyl]pyrazin-2-yl}[(4-methoxyphenyl)methyl]amine (115 mg, 0.25 mmol) in methanol (3 mL) under a nitrogen atmosphere. The mixture is then hydrogenated at 1 ATM for 18 hours, filtered through Celite and evaporated to give 3-ethyl-6-methoxy-5-[2-methoxy-4(trifluoromethoxy)phenyl]pyrazin-2-ylamine (80 mg).

H. A solution of sodium nitrite (21 mg, 0.3 mmol) in water (1 mL) is added to a stirred solution of 3-ethyl-6-methoxy-5-[2-methoxy-4-(trifluoromethoxy)phenyl]pyrazin-2ylamine (86 mg, 0.25 mmol) in 48% hydrogen bromide (0.3 mL) at 0 C. After 1.5 hours copper bromide (43 mg, 0.3 mmol) is added and the mixture heated to 70 C for 1 hour. The mixture is cooled to room temperature and extracted with ether. The extracts are dried (sodium sulfate), filtered and concentrated to give [4-(5-bromo-6-ethyl-3-methoxy-pyrazin-2yl)-3-methoxyphenoxy]trifluoromethane (76 mg).

I. 60% Sodium hydride (12 mg, 0.3 mmol) is added to a stirred solution of 3-pentanol (88 mg, 1 mmol) in THF (1 mL). After 0.5 hours [4-(5-bromo-6-ethyl-3-methoxy-pyrazin-2yl)-3-methoxyphenoxy]trifluoromethane (41 mg, 0.1 mmol) is added. The mixture is heated to 50 C for 12 hours, cooled and partitioned between ethyl acetate and water. The organic layer is washed with water, brine, dried (sodium sulfate), filtered and concentrated. The residue is purified by preparative TLC eluting with 50% ether in hexanes to give {4-[6-Ethyl-5-(ethylpropoxy)-3-methoxy-pyrazin-2-yl]-3-methoxyphenoxy}trifluoromethane, a colorless oil (19 mg). NMR (CDCL3, 400 MHz) δ 0.98 (t, 6H), 1.22 (t, 3H), 1.78 (m, 4H) 2.80 (q, 2H), 3.80 (s, 3H), 3.88 (s, 3H), 5.05 (quintet, 1H), 6.8 (s, 1H), 6.90 (d, 1H), 7.37 (d, 1H); MS 345 (M+1).

Example 25

SYNTHESIS OF [3-ETHYL-5-(2-METHOXY-4-TRIFLUO-ROMETHOXY-PHENYL)-6-METHYLSULFANYL-PYRAZIN-2-YL]-(1-ETHYL-PROPYL)-AMINE.

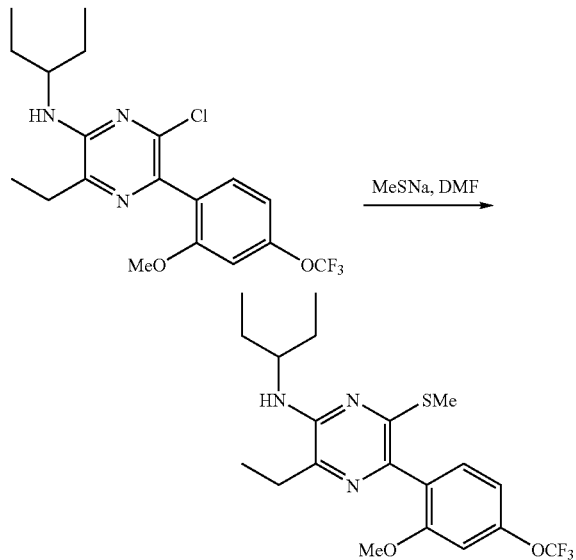

[6-chloro-3-ethyl-5-(2-methoxy-4-trifluoromethoxy-phenyl)-pyrazine-2-yl]-(1-ethyl-propyl)-amine (100 mg is combined in a pressure tube equipped with Teflon O-ring, with NaSMe (200 mg), THF (5 mL) and DMF (3 mL). The mixture is heated at 80° C. (oil bath temperature) for 72 hours. The crude mixture is diluted with ethyl acetate (40 mL) and water (40 mL), and the organic phase washed with brine (3×100 mL). After drying (MgSO$_4$), filtration, and elimination of solvents at reduced pressure, the title compound is isolated as a clear oil by preparative thin layer chromatography (10% EtOAc in hexanes). Yield: 50 mg (49%). NMR (CDCl$_3$, 400 MHz) H-1: 7.32 (1H, d, J=8.4 Hz), 6.88 (1H, m), 6.78 (s, 1H 4.18 (1H, d), 4.07 (m, 1H), 3.78 (3H, s), 2.64 (2H, q), 2.24 (s, 3H), 1.5–1.75 (m, 4H), 1.25 (t, 3H), 0.96 (t, 6H). MS: 430.2 (M+1, positive mode) and 428.4 (M−1, negative mode).

Example 26

PREPARATION OF 2-SEC-BUTYLSULFANYL-5-(2,4-DIMETHOXY-PHENYL)-3,6-DIETHYL-PYRAZINE

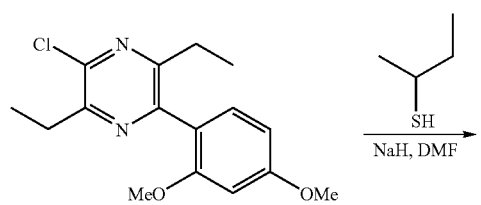

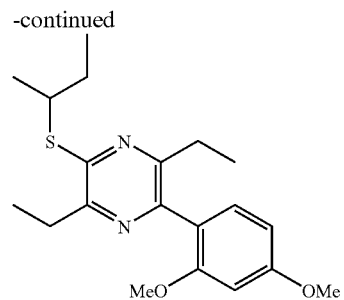

NaH (60 mg, 1.5 mmol. 60% in mineral oil) is added to a solution of butane-2-thiol (170 µL, 1.5 mmol) in THF (5 mL). After 10 minutes, 2-chloro-5-(2,4-dimethoxy-phenyl)-3,6-diethyl-pyrazine (100 mg, 0.33 mmol) in THF (1 mL) is added dropwise, and the mixture heated at 80° C. (oil bath temperature) for 16 hours. After extractive work-up, preparative thin layer chromatography (hexanes) furnishes the title compound as a clear oil (60 mg, 51%). NMR (CDCl$_3$, 400 MHz) H-1: 7.19 (1H, d, J=8.4 Hz), 6.58 (1H, dd, J=2.4, 8.4 Hz), 6.60 (s, 1H, J=2.4 Hz), 3.99 (sext, 1H, J=6.8 Hz), 3.85 (3H, s), 3.75 (3H, s), 2.81 (2H, q, J=7.4 Hz), 2.58 (2H, br q, J=6.8 Hz), 1.6–1.9 (m, 4H), 1.44 (3H, d, J=6.4 Hz), 1.28 (t, 3H, J=7.6 Hz), 1.19 (3H, t, J=7.6 Hz), 1.06 (t, 3H, J=7.2 Hz). C-13: 161.10, 157.86, 153.49, 151.79, 151.67, 144.47, 131.68, 121.18, 104.78, 98, 60, 55.44, 55.33, 40.87, 29.65, 27.54, 27.08, 20.56, 12.43, 12.09, 11.51. MS: 414.2 (+1, positive mode) and 412.2 (M−1, negative mode).

Example 27

PREPARATION OF 1-[3,6-DIETHYL-5-(2-METHYLBUTYL)PYRAZIN-2-YL]-2,4-DIMETHOXYBENZENE

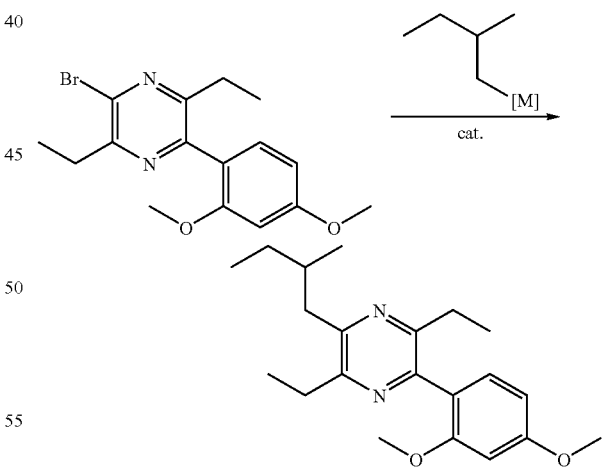

A solution of 9-BBN (9-borabicyclo[3.3.1]nonane) in THF (0.5 M, 6.0 mL, 3.0 mmol) is added to a solution of 2-methyl-1-butene (210 mg, 3.0 mmol) in THF. The mixture is heated at reflux, under a nitrogen atmosphere for 12 hours and cooled. 1-(5-Bromo-3,6-diethylpyrazin-2-yl)-2,4-dimethoxybenzene (664 mg, 2.0 mmol), tetrakis(triphenylphosphine) palladium(0) (50 mg), and sodium hydroxide (3.0 M, 3.0 mL, 3.0 mmol) are added to the solution. The mixture is heated at 50 C for 12 hours and cooled. 30%

Hydrogen peroxide (1 mL) is added, the solution stirred for 1 hour and the reaction mixture extracted with ether. The combined extracts are dried (sodium sulfate), filtered and concentrated. The residue is purified by flash chromatography, eluting with 40% ether in hexanes to give 1-[3,6-diethyl-5-(2-methylbutyl)pyrazin-2-yl]-2,4-dimethoxybenzene (393 mg).

Example 28

PREPARATION OF 2-(2-METHOXY-5-TRIFLURORMETHOXYPHENYL)-3-ETHYL-6-METHYLAMINO-5-(1-ETHYLPROPOXY)-PYRAZINE

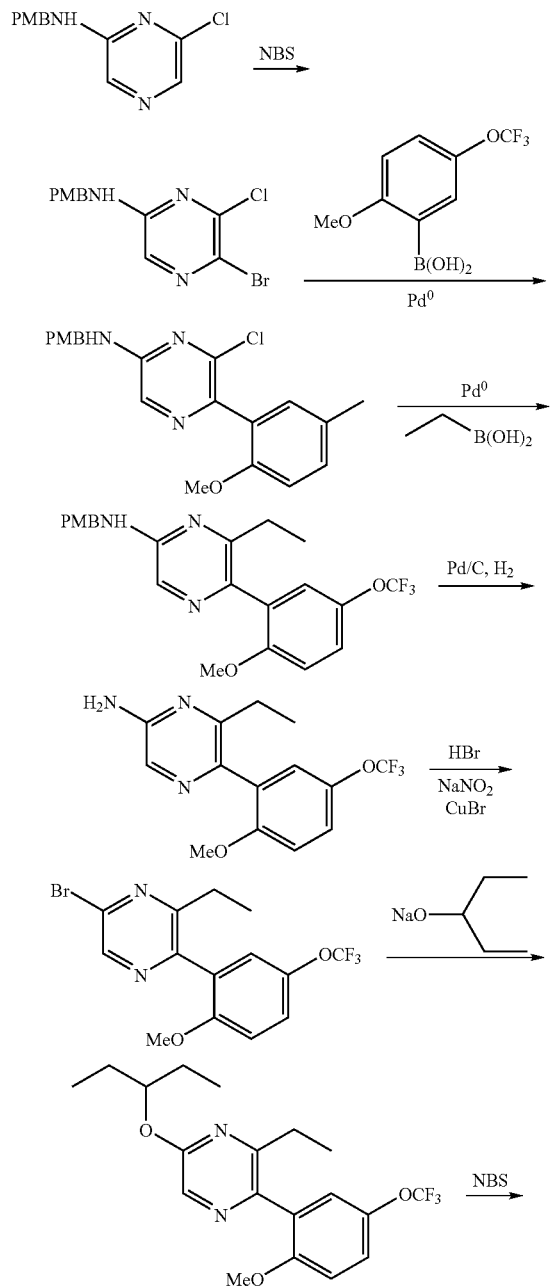

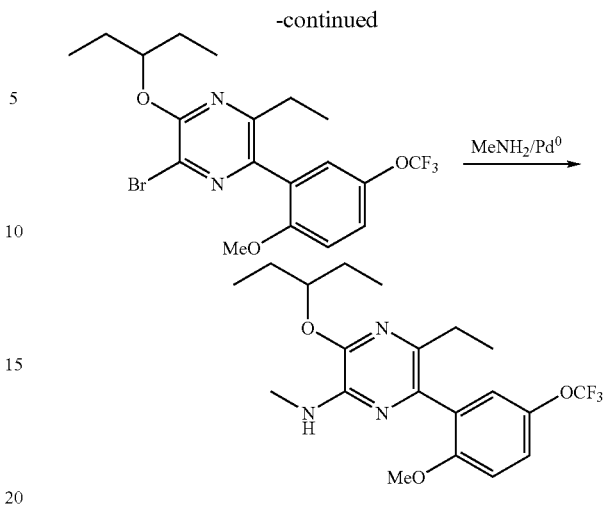

A. A solution of 6-(Chloropyrazin-2-yl)[(4-methoxyphenyl)methyl]amine in chloroform (4 mL/mmol NBS) is cooled to 0° C. and N-bromosuccinimide (1.05 eq) is added in portions while stirring the reaction mixture. After complete addition, the mixture is stirred for an additional hour while being allowed to warm to room temperature. The mixture is then diluted with dichloromethane, washed with saturated NaHCO$_3$, water, and brine, and then dried and filtered. The filtrate is concentrated and purified by chromatography on silica gel to give (5-bromo-6-chloropyrazin-2-yl)[(4-methoxyphenyl)methyl]amine.

B. In a pressure tube, a mixture of the product from step A (1 equivalent), 2-methoxy-5-trifluoromethoxyphenylboronic acid (1.6 equivalents) and Pd(PPh$_3$)$_4$ (0.04 equivalents) in toluene (4 ml/mmol of product from step A), ethanol (0.2 ml/mmol of product from step A) and aqueous K$_2$CO$_3$ (2M, 2 ml/mmol of product from step A) is heated to 80° C. for 16 hours. The mixture is diluted with ethyl acetate, and the organic fraction washed with NaOH (2M, 20 mL/mmol of product from step A) and brine (3×20 ml/mmol of product from step A), then dried (MgSO$_4$), filtered and the solvent removed under reduced pressure. Chromatography of the residue provides (3-(2-methoxy-5-trifluoromethoxyphenyl)-6-chloropyrazin-2-yl)[(4-methoxyphenyl)methyl]amine.

C. (5-(2-methoxy-5-trifluoromethoxyphenyl)-6-ethylpyrazin-2-yl)[(4-methoxyphenyl)methyl]amine can be prepared by the method of Example 1, step A by substituting (5-(2-methoxy-5-trifluoromethoxyphenyl)-6-chloropyrazin-2-yl)[(4-methoxyphenyl)methyl]amine for 2-chloro-3,6-dimethylpyrazine.

D. (5-(2-methoxy-5-trifluoromethoxyphenyl)-6-ethylpyrazin-2-yl)amine can be prepared by the hydrogenation method of Example 24, step G by substituting (5-(2-methoxy-5-trifluoromethoxyphenyl)-6-ethylpyrazin-2-yl)[(4-methoxyphenyl)methyl]amine for {3-ethyl-6-methoxy-5-[2-methoxy-4-(trifluoromethoxy)phenyl]pyrazin-2-yl} [(4-methoxyphenyl)methyl]amine.

E. 2-Bromo-5-(2-methoxy-5-trifluoromethoxyphenyl)-6-ethylpyrazine can be prepared by the halogenation method of Example 24, step H, by substituting (5-(2-methoxy-5-trifluoromethoxyphenyl)-6-ethylpyrazin-2-yl)amine for {3-ethyl-6-methoxy-5-[2-methoxy-4-(trifluoromethoxy) phenyl]pyrazin-2-yl} amine.

F. 2-(3-Pentoxy)-(5-(2-methoxy-5-trifluoromethoxyphenyl)-6-ethylpyrazine can be prepared by the method of Example 24, step I by substituting 2-bromo-(5-(2-methoxy-5-trifluoromethoxyphenyl)-6-ethylpyrazin-2-yl)[(4-methoxyphenyl)methyl]amine for [4-(5-bromo-6-ethyl-3-methoxy-pyrazin-2-yl)-3-methoxyphenoxy]trifluoromethane.

G. 2-(3-Pentoxy)-3-bromo-(5-(2-methoxy-5-trifluoromethoxyphenyl)-6-ethylpyrazine can be prepared by the method of step A of the present Example by substituting 2-(3-Pentoxy)-3-bromo-(5-(2-methoxy-5-trifluoromethoxyphenyl)-6-ethylpyrazine for (6-chloropyrazin-2-yl)[(4-methoxyphenyl)methyl]amine.

H. Methylamine (1.2 equivalents) followed by sodium tert-butoxide (1.5 equivalents) is added to a mixture of 2-(3-Pentoxy)-3-bromo-(5-(2-methoxy-5-trifluoromethoxyphenyl)-6-ethylpyrazine (1 equivalent), tris(dibenzylideneacetone)dipalladium(0) (2 mol %), and 1,1'-binaphthyl-2,2'-di(diphenylphosphine) (BINAP) (6 mol %) in ethyleneglycol dimethyl ether (2.4 mL/mmol substrate) under nitrogen. The mixture is stirred at 70–80° C. for about 2.5 hours, diluted with aqueous ammonium chloride, and extracted with 1:1 hexane-diethyl ether. The combined extracts are dried (sodium sulfate), filtered, concentrated and then purified by chromatography on silica gel to afford 2-(3-Pentoxy)-3-(N-methylamino)-(5-(2-methoxy-5-trifluoromethoxyphenyl)-6-ethylpyrazine.

Example 29

ADDITIONAL COMPOUNDS OF FORMULA I

The following compounds, shown in Tables I, II, and III were prepared using the methods shown in above Schemes I–IV, and further illustrated by Examples 1–28. Compounds shown in Table III each have a $K_i < 1$ μm

TABLE I

| CMP # | STRUCTURE | IUPAC NAME | Ki < 1 μM |
|---|---|---|---|
| 1 | 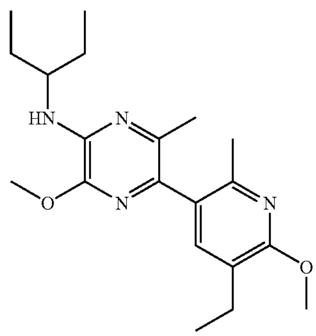 | [5-(5-Ethyl-6-methoxy-2-methyl-pyridin-3-yl)-3-methoxy-6-methyl-pyrazin-2-yl]-(1-ethyl-propyl)-amine | * |
| 2 | 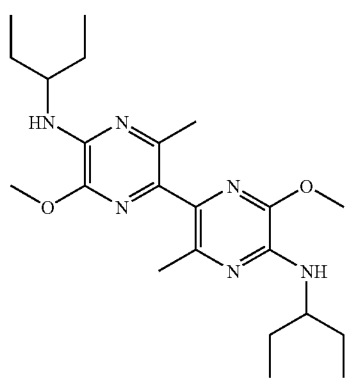 | N-5,N-5'-Bis-(1-ethyl-propyl)-6,6'-dimethoxy-3,3'-dimethyl-[2,2']bipyrazinyl-5,5'-diamine | * |
| 3 | 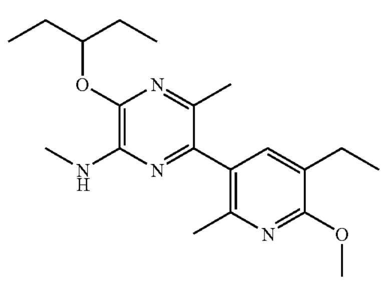 | [5-Methyl-6-(5-ethyl-6-methoxy-2-methyl-pyridin-3-yl)-3-(1-ethyl-propoxy)-pyrazin-2-yl]-methyl-amine | * |

TABLE I-continued

| CMP # | STRUCTURE | IUPAC NAME | Ki < 1 μM |
|---|---|---|---|
| 4 | 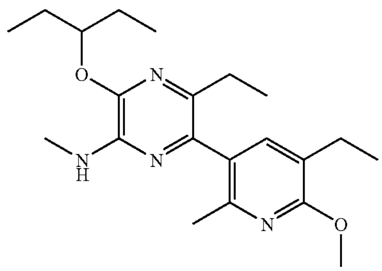 | [5-Ethyl-6-(5-ethyl-6-methoxy-2-methyl-pyridin-3-yl)-3-(1-ethyl-propoxy)-pyrazin-2-yl]-methyl-amine | * |
| 5 | 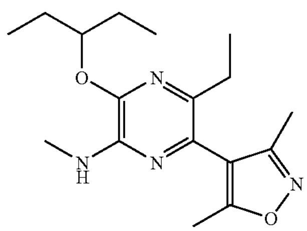 | [6-(3,5-Dimethyl-isoxazol-4-yl)-5-ethyl-3-(1-ethyl-propoxy)-pyrazin-2-yl]-methyl-amine | * |
| 6 | 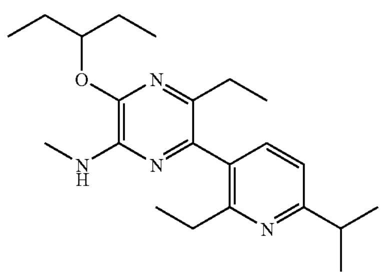 | [5-Ethyl-6-(2-ethyl-6-isopropoxy-2-pyridin-3-yl)-3-(1-ethyl-propoxy)-pyrazin-2-yl]-methyl-amine | * |
| 7 | 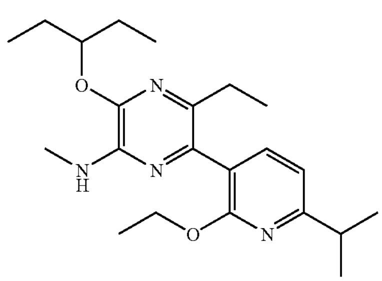 | [5-Ethyl-6-(2-ethoxy-6-isopropoxy-2-pyridin-3-yl)-3-(1-ethyl-propoxy)-pyrazin-2-yl]-methyl-amine | * |
| 8 | 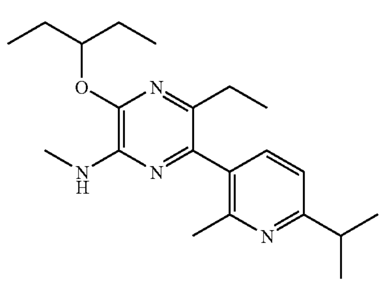 | [5-Ethyl-6-(2-methyl-6-isopropyl-2-pyridin-3-yl)-3-(1-ethyl-propoxy)-pyrazin-2-yl]-methyl-amine | * |

TABLE I-continued

| CMP # | STRUCTURE | IUPAC NAME | Ki < 1 µM |
|---|---|---|---|
| 9 | 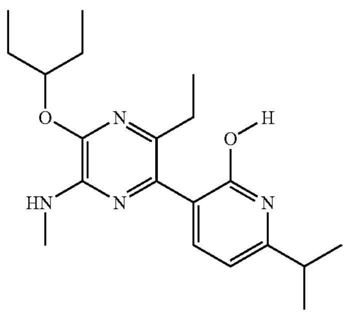 | [5-Ethyl-6-(2-hydroxy-6-isopropyl-2-pyridin-3-yl)-3-(1-ethyl-propoxy)-pyrazin-2-yl]-methyl-amine | * |
| 10 | 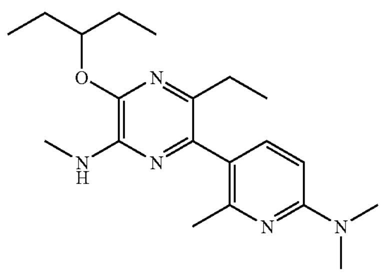 | [5-Ethyl-6-(2-methyl-6-dimethylamino-2-pyridin-3-yl)-3-(1-ethyl-propoxy)-pyrazin-2-yl]-methyl-amine | * |
| 11 | 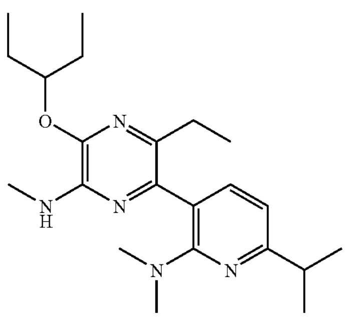 | [5-Ethyl-6-(2-dimethylamino-6-isopropyl-2-pyridin-3-yl)-3-(1-ethyl-propoxy)-pyrazin-2-yl]-methyl-amine | * |
| 12 | 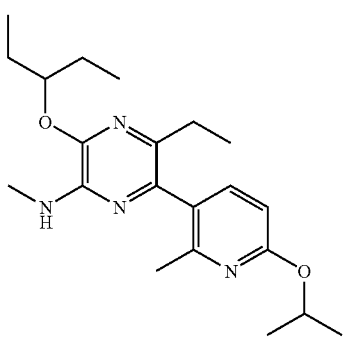 | [6-(2-methyl-6-isopropyl-pyridin-3-yl)-5-ethyl-3-(1-ethyl-propoxy)-pyrazin-2-yl]-methyl-amine | * |
| 13 | 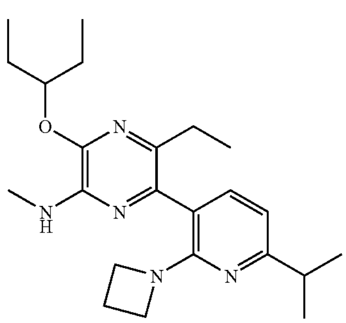 | [6-(2-Azetidin-1-yl-6-isopropyl-pyridin-3-yl)-5-ethyl-3-(1-ethyl-propoxy)-pyrazin-2-yl]-methyl-amine | * |

TABLE I-continued

| CMP # | STRUCTURE | IUPAC NAME | Ki < 1 μM |
|---|---|---|---|
| 14 | 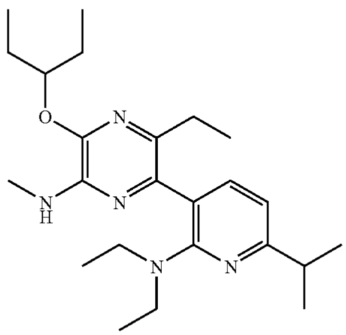 | [6-(2-Diethylamino-6-isopropyl-pyridin-3-yl)-5-ethyl-3-(1-ethyl-propoxy)-pyrazin-2-yl]-methyl-amine | * |
| 15 | 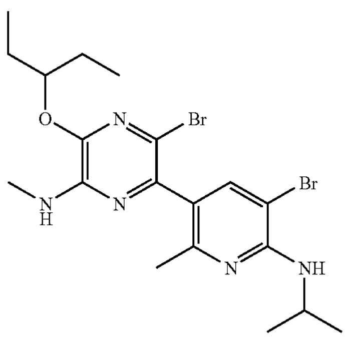 | [3-(1-Ethyl-propoxy)-6-(6-isopropyl-amino-2-methyl-5-bromo-pyridin-3-yl)-5-bromo-pyrazin-2-yl]-methyl-amine | * |
| 16 | 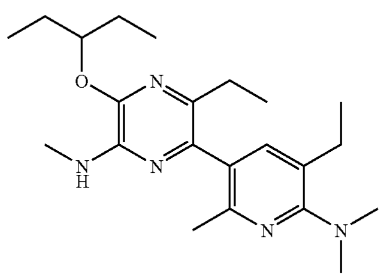 | [6-(6-Dimethylamino-5-ethyl-2-methyl-pyridin-3-yl)-5-ethyl-3-(1-ethyl-propoxy)-pyrazin-2-yl]-methyl-amine | * |
| 17 | 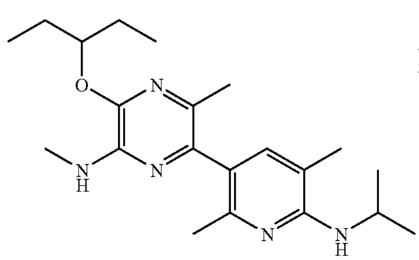 | [3-(1-Ethyl-propoxy)-6-(6-isopropyl-amino-2,5-dimethyl-pyridin-3-yl)-5-methyl-pyrazin-2-yl]-methyl-amine | * |

TABLE II

| CMP # | STRUCTURE | IUPAC NAME |
|---|---|---|
| 18 | 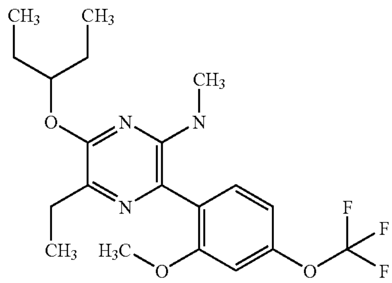 | 5-ethyl-6-(1-ethylpropoxy)-3-[2-methoxy-4-(trifluoromethoxy)phenyl]-N-methylpyrazin-2-amine |
| 19 | 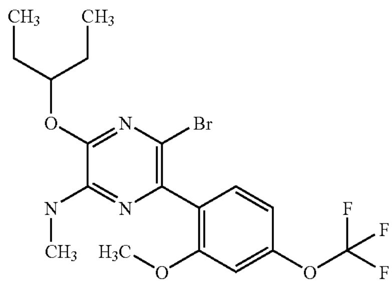 | 5-bromo-3-(1-ethylpropoxy)-6-[2-methoxy-4-(trifluoromethoxy)phenyl]-N-methylpyrazin-2-amine |
| 20 | 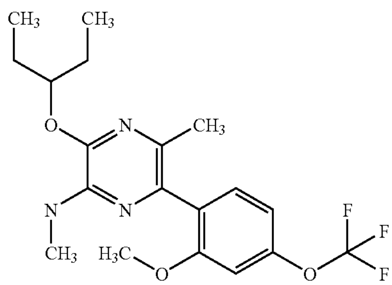 | 3-(1-ethylpropoxy)-6-[2-methoxy-4-(trifluoromethoxy)phenyl]-N,5-dimethylpyrazin-2-amine |
| 21 | 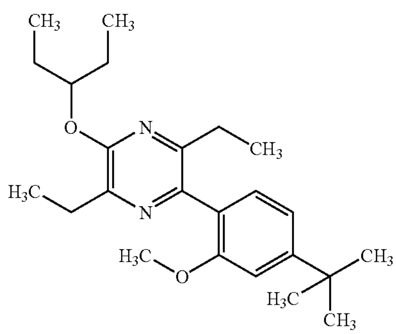 | 2-(4-tert-butyl-2-methoxyphenyl)-3,6-diethyl-5-(1-ethylpropoxy)pyrazine |
| 22 | 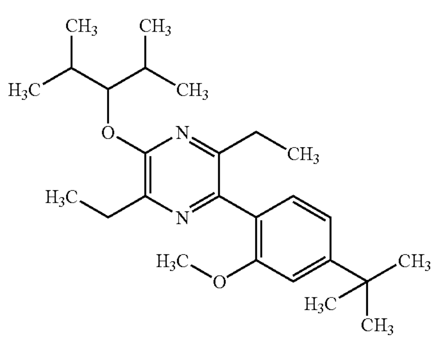 | 2-(4-tert-butyl-2-methoxyphenyl)-3,6-diethyl-5-(1-isopropyl-2-methylpropoxy)pyrazine |

TABLE II-continued

| CMP # | STRUCTURE | IUPAC NAME |
|---|---|---|
| 23 | 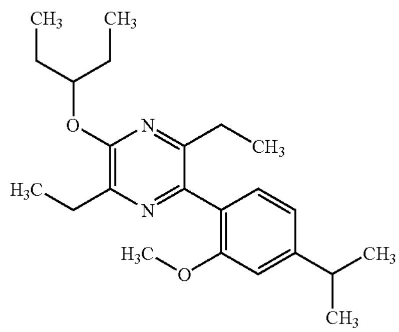 | 2,5-diethyt-3-(1-ethylpropoxy)-6-(4-isopropyl-2-methoxyphenyl)pyrazine |
| 24 | 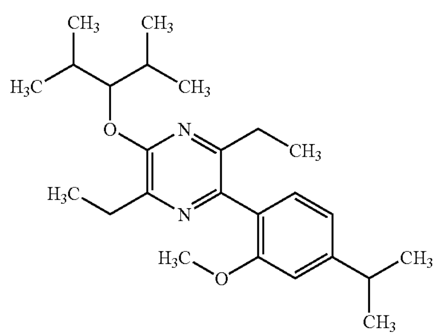 | 2,5-diethyl-3-(4-isopropyl-2-methoxyphenyl)-6-(1-isopropyl-2-methylpropoxy)pyrazine |
| 25 | 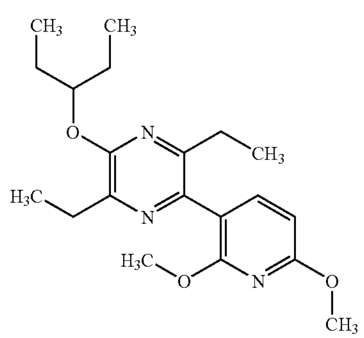 | 2-(2,6-dimethoxypyridin-3-yl)-3,6-diethyl-5-(1-ethylpropoxy)pyrazine |
| 26 | 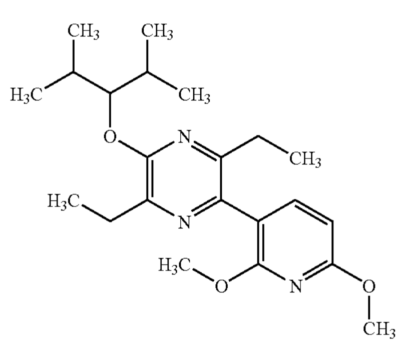 | 2-(2,6-dimethoxypyridin-3-yl)-3,6-diethyl-5-(1-isopropyl-2-methylpropoxy)pyrazine |

TABLE II-continued

| CMP # | STRUCTURE | IUPAC NAME |
|---|---|---|
| 27 | 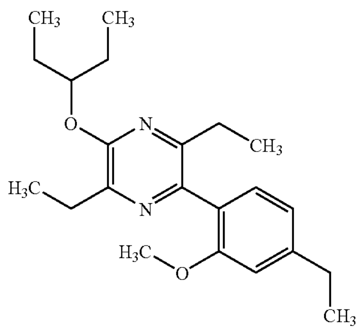 | 2,5-diethyl-3-(4-ethyl-2-methoxyphenyl)-6-(1-ethylpropoxy)pyrazine |
| 28 | 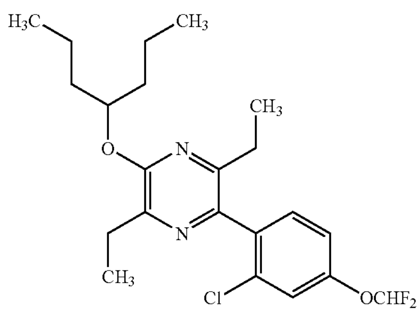 | 2-[2-chloro-4-(difluoromethoxy)phenyl]-3,6-diethyl-5-(1-propylbutoxy)pyrazine |
| 29 | 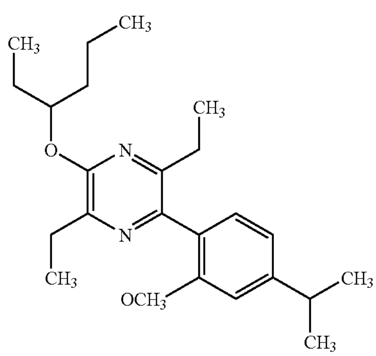 | 2,5-diethyl-3-(1-ethylbutoxy)-6-(4-isopropyl-2-methoxyphenyl)pyrazine |
| 30 | 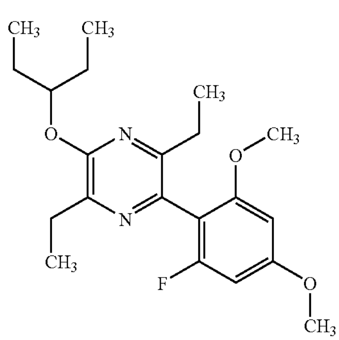 | 2,5-diethyl-3-(1-ethylpropoxy)-6-(2-fluoro-4,6-dimethoxyphenyl)pyrazine |

TABLE II-continued
| CMP # | STRUCTURE | IUPAC NAME |
|---|---|---|
| 31 | 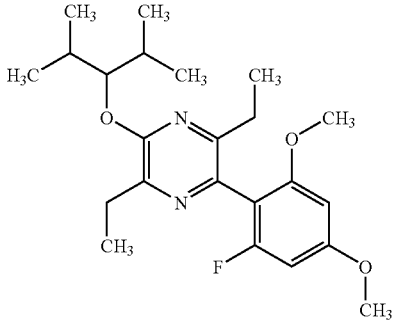 | 2,5-diethyl-3-(2-fluoro-4,6-dimethoxyphenyl)-6-(1-isopropyl-2-methylpropoxy)pyrazine |
| 32 | 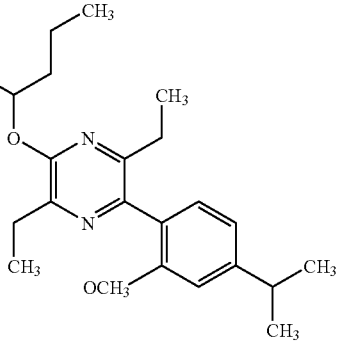 | 2,5-diethyl-3-(4-isopropyl-2-methoxyphenyl)-6-(1-propylbutoxy)pyrazine |
| 33 | 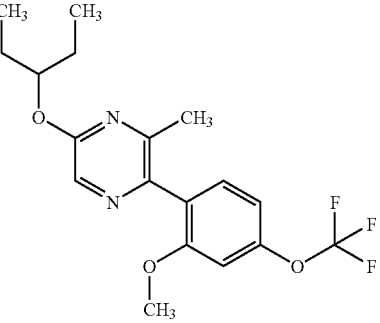 | 5-(1-ethylpropoxy)-2-[2-methoxy-4-(trifluoromethoxy)phenyl]-3-methylpyrazine |
| 34 | 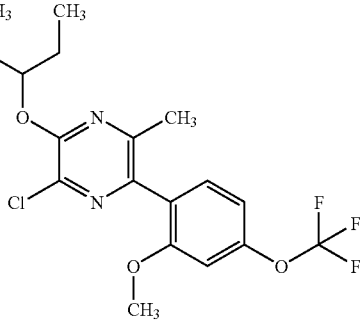 | 2-chloro-3-(1-ethylpropoxy)-6-[2-methoxy-4-(trifluoromethoxy)phenyl]-5-methylpyrazine |

TABLE II-continued

| CMP # | STRUCTURE | IUPAC NAME |
|---|---|---|
| 35 | 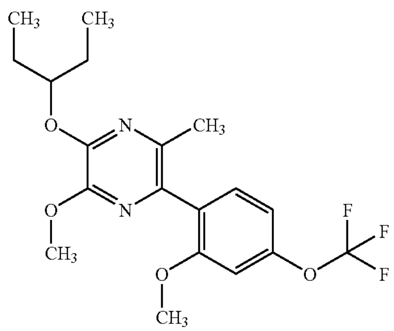 | 2-(1-ethylpropoxy)-3-methoxy-5-[2-methoxy-4-(trifluoromethoxy)phenyl]-6-methylpyrazine |
| 36 | 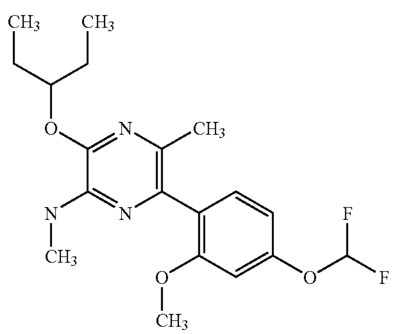 | 6-[4-(difluoromethoxy)-2-methoxyphenyl]-3-(1-ethylpropoxy)-N,5-dimethylpyrazin-2-amine |
| 37 | 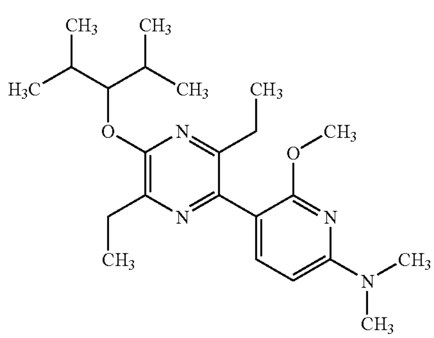 | 5-[3,6-diethyl-5-(1-isopropyl-2-methylpropoxy)pyrazin-2-yl]-6-methoxy-N,N-dimethylpyridin-2-amine |
| 38 | 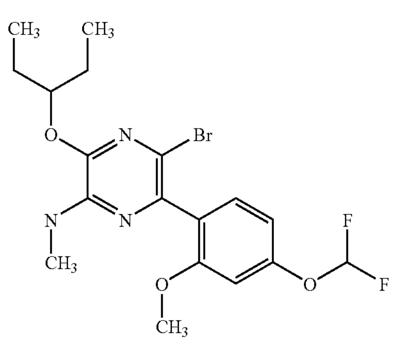 | 5-bromo-6-[4-(difluoromethoxy)-2-methoxyphenyl]-3-(1-ethylpropoxy)-N-methylpyrazin-2-amine |

TABLE II-continued

| CMP # | STRUCTURE | IUPAC NAME |
|---|---|---|
| 39 | 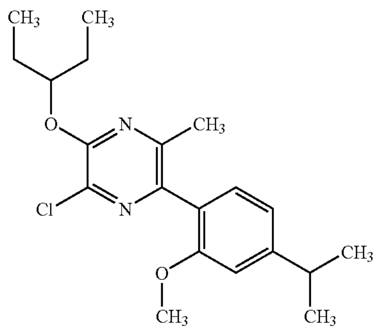 | 2-chloro-3-(1-ethylpropoxy)-6-(4-isopropyl-2-methoxyphenyl)-5-methylpyrazine |
| 40 | 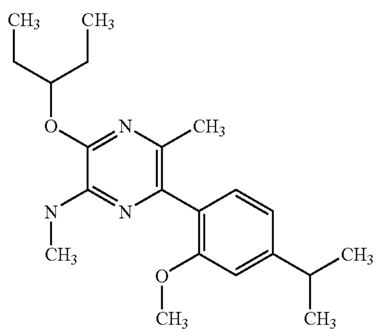 | 3-(1-ethylpropoxy)-6-(4-isopropyl-2-methoxyphenyl)-N,5-dimethylpyrazin-2-amine |
| 41 | 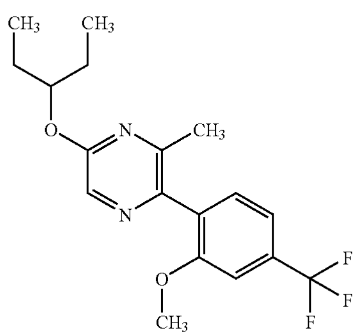 | 5-(1-ethylpropoxy)-2-[2-methoxy-4-(trifluoromethyl)phenyl]-3-methylpyrazine |
| 42 | 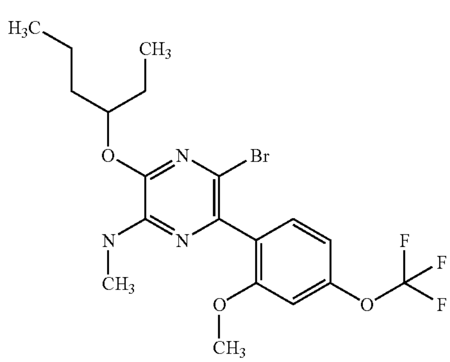 | 5-bromo-3-(1-ethylbutoxy)-6-[2-methoxy-4-(trifluoromethoxy)phenyl]-N-methylpyrazin-2-amine |

TABLE II-continued
| CMP # | STRUCTURE | IUPAC NAME |
|---|---|---|
| 43 | 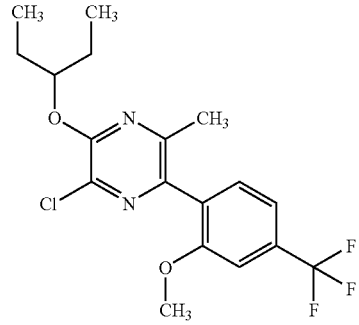 | 2-chloro-3-(1-ethylpropoxy)-6-[2-methoxy-4-(trifluoromethyl)phenyl]-5-methylpyrazine |
| 44 | 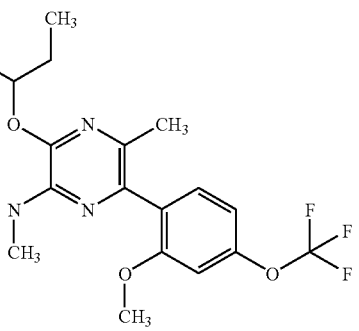 | 3-(1-ethylbutoxy)-6-[2-methoxy-4-(trifluoromethoxy)phenyl]-N,5-dimethylpyrazin-2-amine |
| 45 | 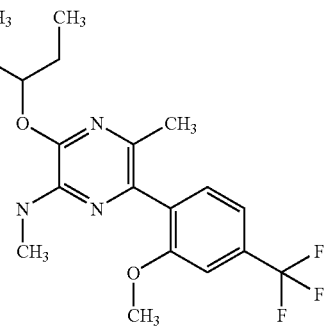 | 3-(1-ethylpropoxy)-6-[2-methoxy-4-(trifluoromethyl)phenyl]-N,5-dimethylpyrazin-2-amine |
| 46 | 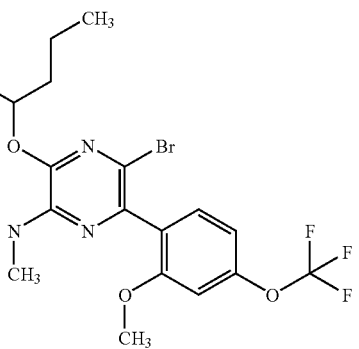 | 5-bromo-6-[2-methoxy-4-(trifluoromethoxy)phenyl]-N-methyl-3-(1-propylbutoxy)pyrazin-2-amine |

TABLE II-continued

| CMP # | STRUCTURE | IUPAC NAME |
|---|---|---|
| 47 | 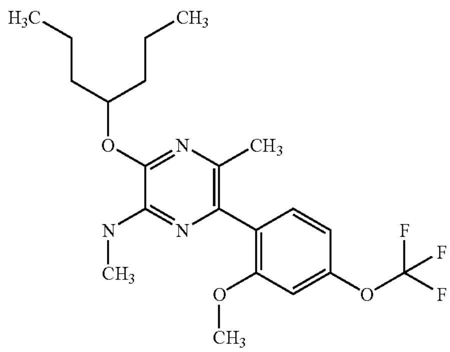 | 6-[2-methoxy-4-(trifluoromethoxy)phenyl]-N,5-dimethyl-3-(1-propylbutoxy)pyrazin-2-amine |
| 48 | 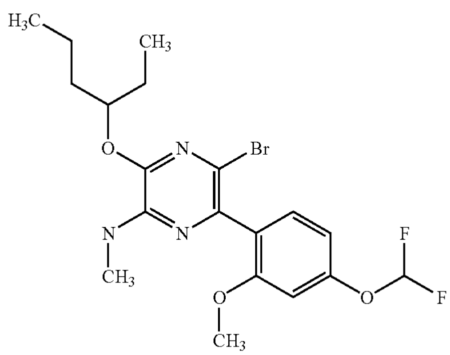 | 5-bromo-6-[4-(difluoromethoxy)-2-methoxyphenyl]-3-(1-ethylbutoxy)-N-methylpyrazin-2-amine |
| 49 | 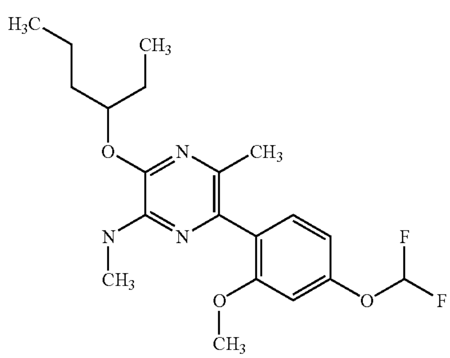 | 6-[4-(difluoromethoxy)-2-methoxyphenyl]-3-(1-ethylbutoxy)-N,5-dimethylpyrazin-2-amine |
| 50 | 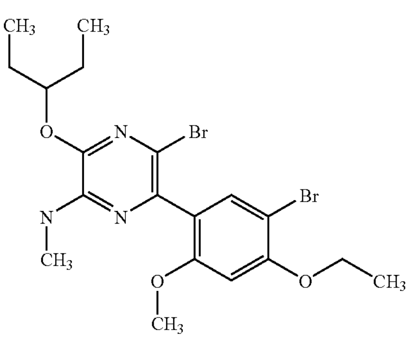 | 5-bromo-6-(5-bromo-4-ethoxy-2-methoxyphenyl)-3-(1-ethylpropoxy)-N-methylpyrazin-2-amine |

TABLE II-continued

| CMP # | STRUCTURE | IUPAC NAME |
|---|---|---|
| 51 | 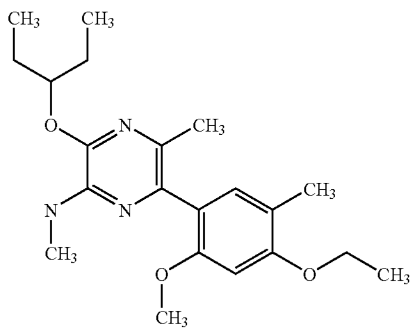 | 6-(4-ethoxy-2-methoxy-5-methylphenyl)-3-(1-ethylpropoxy)-N,5-dimethylpyrazin-2-amine |
| 52 | 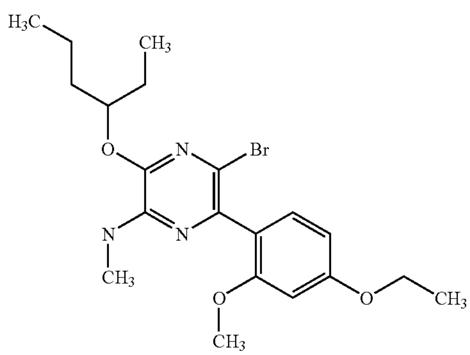 | 5-bromo-6-(4-ethoxy-2-methoxyphenyl)-3-(1-ethylbutoxy)-N-methylpyrazin-2-amine |
| 53 | 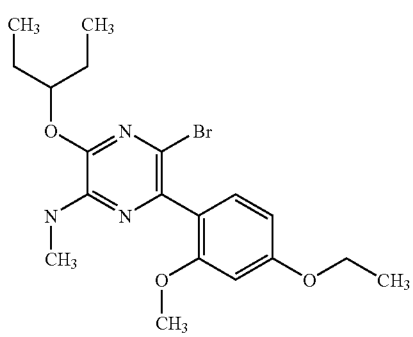 | 5-bromo-6-(4-ethoxy-2-methoxyphenyl)-3-(1-ethylpropoxy)-N-methylpyrazin-2-amine |
| 54 | 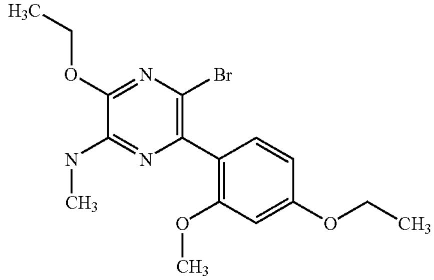 | 5-bromo-3-ethoxy-6-(4-ethoxy-2-methoxyphenyl)-N-methylpyrazin-2-amine |

TABLE II-continued

| CMP # | STRUCTURE | IUPAC NAME |
|---|---|---|
| 55 | 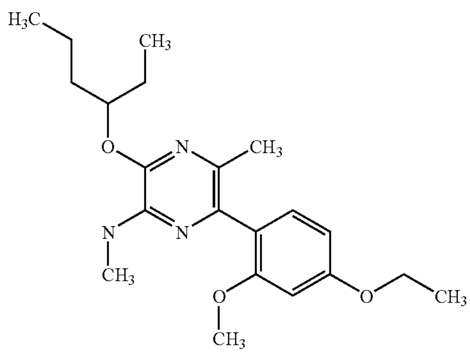 | 6-(4-ethoxy-2-methoxyphenyl)-3-(1-ethylbutoxy)-N,5-dimethylpyrazin-2-amine |
| 56 | 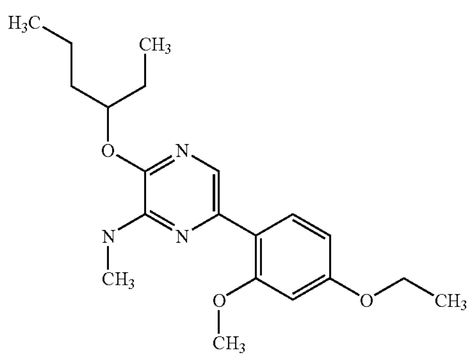 | 6-(4-ethoxy-2-methoxyphenyl)-3-(1-ethylbutoxy)-N-methylpyrazin-2-amine |
| 57 | 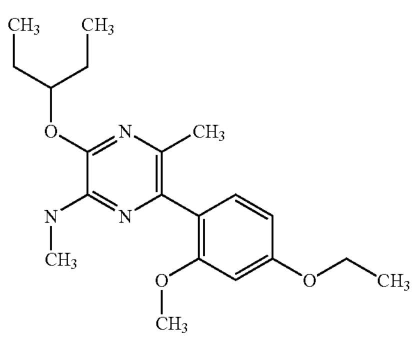 | 6-(4-ethoxy-2-methoxyphenyl)-3-(1-ethylpropoxy)-N,5-dimethylpyrazin-2-amine |
| 58 | 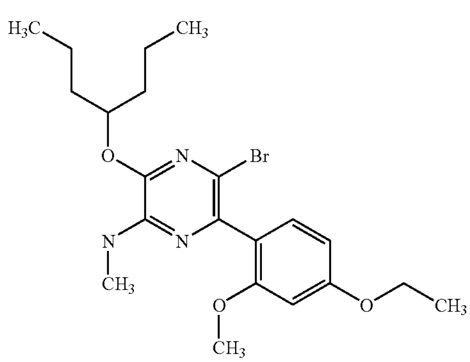 | 5-bromo-6-(4-ethoxy-2-methoxyphenyl)-N-methyl-3-(1-propylbutoxy)pyrazin-2-amine |

TABLE II-continued
| CMP # | STRUCTURE | IUPAC NAME |
|---|---|---|
| 59 | 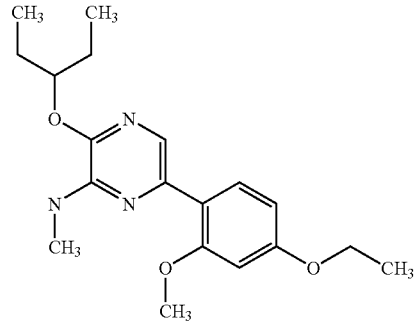 | 6-(4-ethoxy-2-methoxyphenyl)-3-(1-ethylpropoxy)-N-methylpyrazin-2-amine |
| 60 | 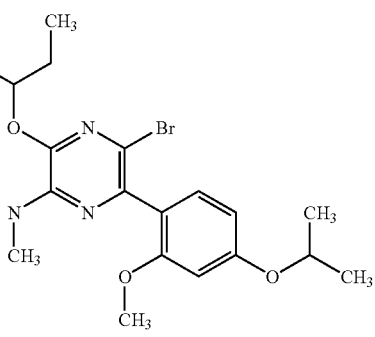 | 5-bromo-3-(1-ethylbutoxy)-6-(4-isopropoxy-2-methoxyphenyl)-N-methylpyrazin-2-amine |
| 61 | 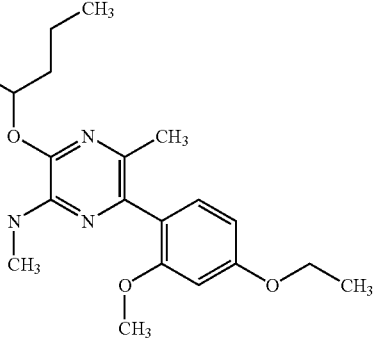 | 6-(4-ethoxy-2-methoxyphenyl)-N,5-dimethyl-3-(1-propylbutoxy)pyrazin-2-amine |
| 62 | 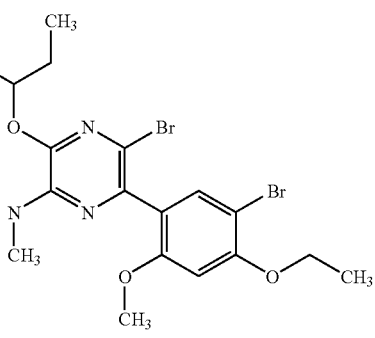 | 5-bromo-6-(5-bromo-4-ethoxy-2-methoxyphenyl)-3-(1-ethylbutoxy)-N-methylpyrazin-2-amine |

TABLE II-continued
| CMP # | STRUCTURE | IUPAC NAME |
|---|---|---|
| 63 | 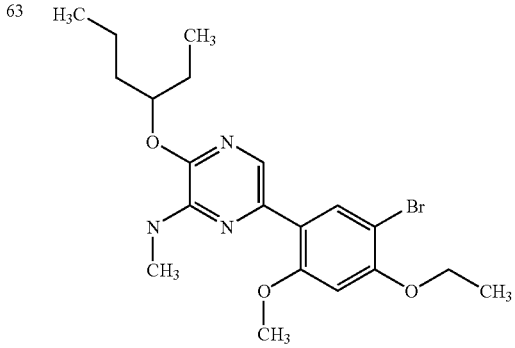 | 6-(5-bromo-4-ethoxy-2-methoxyphenyl)-3-(1-ethylbutoxy)-N-methylpyrazin-2-amine |
| 64 | 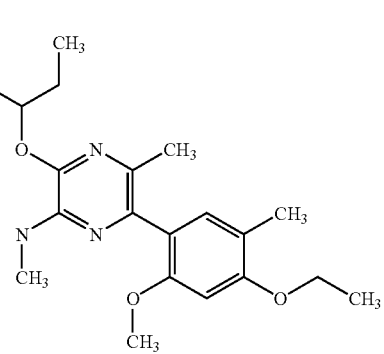 | 6-(4-ethoxy-2-methoxy-5-methylphenyl)-3-(1-ethylbutoxy)-N,5-dimethylpyrazin-2-amine |
| 65 | 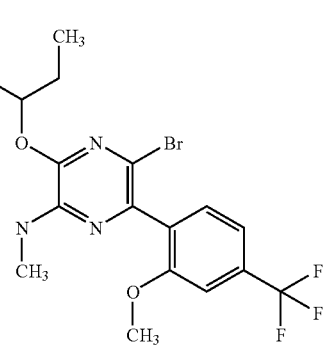 | 5-bromo-3-(1-ethylbutoxy)-6-[2-methoxy-4-(trifluoromethyl)phenyl]-N-methylpyrazin-2-amine |
| 66 | 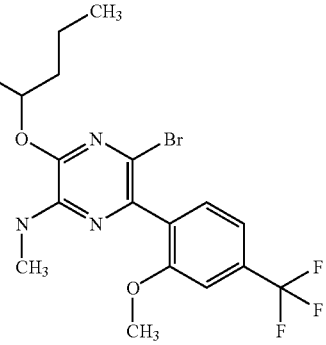 | 5-bromo-6-[2-methoxy-4-(trifluoromethyl)phenyl]-N-methyl-3-(1-propylbutoxy)pyrazin-2-amine |

TABLE II-continued

| CMP # | STRUCTURE | IUPAC NAME |
|---|---|---|
| 67 | 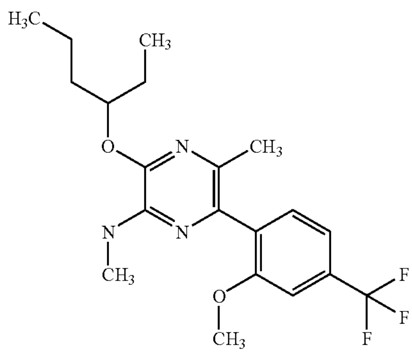 | 3-(1-ethylbutoxy)-6-[2-methoxy-4-(trifluoromethyl)phenyl]-N,5-dimethylpyrazin-2-amine |
| 68 | 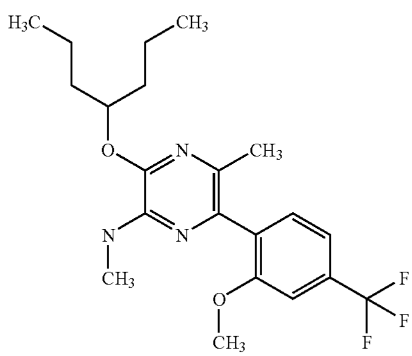 | 6-[2-methoxy-4-(trifluoromethyl)phenyl]-N,5-dimethyl-3-(1-propylbutoxy)pyrazin-2-amine |
| 69 | 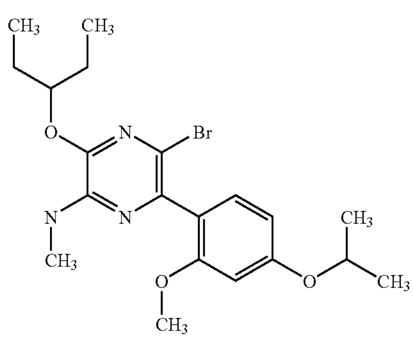 | 5-bromo-3-(1-ethylpropoxy)-6-(4-isopropoxy-2-methoxyphenyl)-N-methylpyrazin-2-amine |
| 70 | 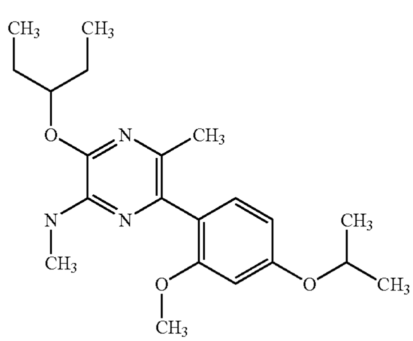 | 3-(1-ethylpropoxy)-6-(4-isopropoxy-2-methoxyphenyl)-N,5-dimethylpyrazin-2-amine |

TABLE II-continued

| CMP # | STRUCTURE | IUPAC NAME |
|---|---|---|
| 71 | 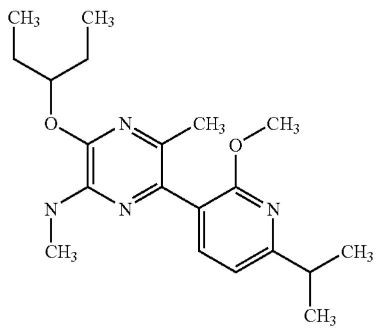 | 3-(1-ethylpropoxy)-6-(6-isopropyl-2-methoxypyridin-3-yl)-N,5-dimethylpyrazin-2-amine |
| 72 | 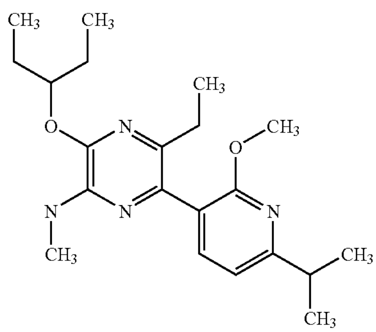 | 5-ethyl-3-(1-ethylpropoxy)-6-(6-isopropyl-2-methoxypyridin-3-yl)-N-methylpyrazin-2-amine |
| 73 | 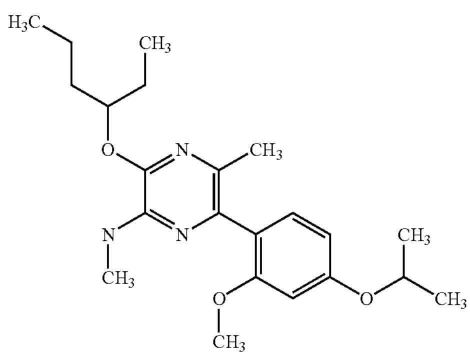 | 3-(1-ethylbutoxy)-6-(4-isopropoxy-2-methoxyphenyl)-N,5-dimethylpyrazin-2-amine |
| 74 | 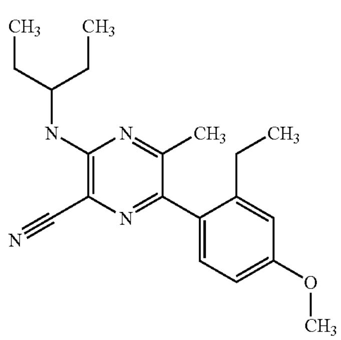 | 6-(2-ethyl-4-methoxyphenyl)-3-[(1-ethylpropyl)amino]-5-methylpyrazine-2-carbonitrile |

TABLE II-continued

| CMP # | STRUCTURE | IUPAC NAME |
|---|---|---|
| 75 | 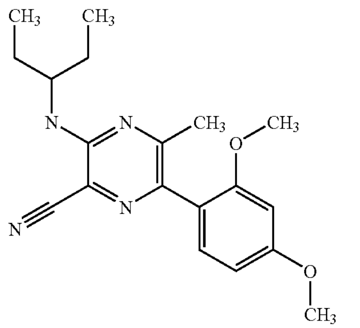 | 6-(2,4-dimethoxyphenyl)-3-[(1-ethylpropyl)amino]-5-methylpyrazine-2-carbonitrile |
| 76 | 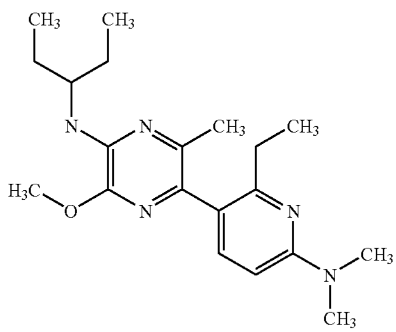 | 5-[6-(dimethylamino)-2-ethylpyridin-3-yl]-N-(1-ethylpropyl)-3-methoxy-6-methylpyrazin-2-amine |
| 77 | 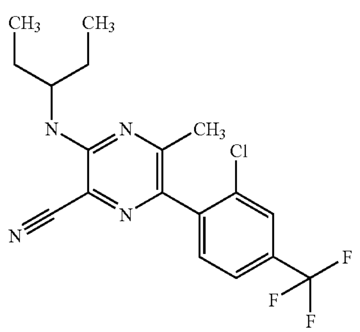 | 6-[2-chloro-4-(trifluoromethyl)phenyl]-3-[(1-ethylpropyl)amino]-5-methylpyrazine-2-carbonitrile |
| 78 | 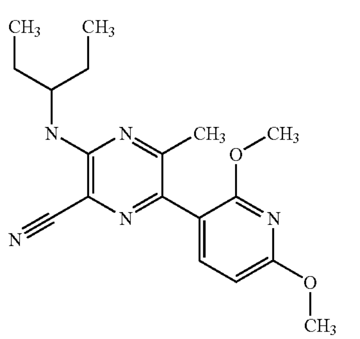 | 6-(2,6-dimethoxypyridin-3-yl)-3-[(1-ethylpropyl)amino]-5-methylpyrazine-2-carbonitrile |

TABLE II-continued

| CMP # | STRUCTURE | IUPAC NAME |
|---|---|---|
| 79 | 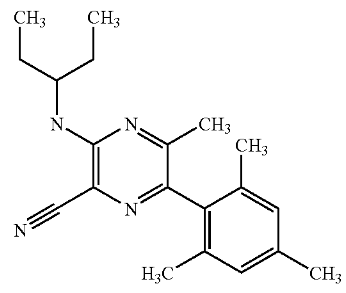 | 3-[(1-ethylpropyl)amino]-6-mesityl-5-methylpyrazine-2-carbonitrile |
| 80 | 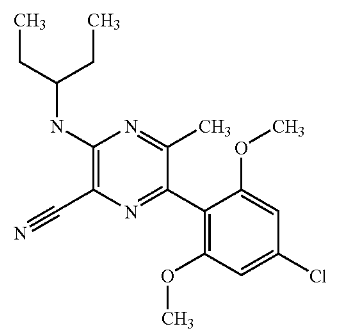 | 6-(4-chloro-2,6-dimethoxyphenyl)-3-[(1-ethylpropyl)amino]-5-methylpyrazine-2-carbonitrile |
| 81 | 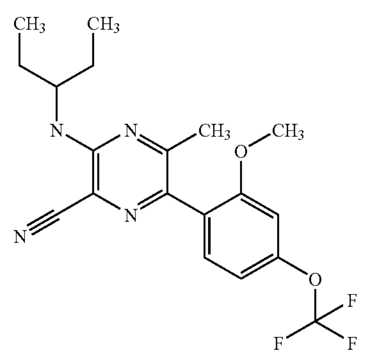 | 3-[(1-ethylpropyl)amino]-6-[2-methoxy-4-(trifluoromethoxy)phenyl]-5-methylpyrazine-2-carbonitrile |
| 82 | 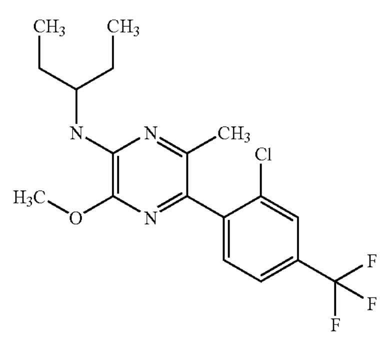 | 5-[2-chloro-4-(trifluoromethyl)phenyl]-N-(1-ethylpropyl)-3-methoxy-6-methylpyrazin-2-amine |

TABLE II-continued

| CMP # | STRUCTURE | IUPAC NAME |
|---|---|---|
| 83 | 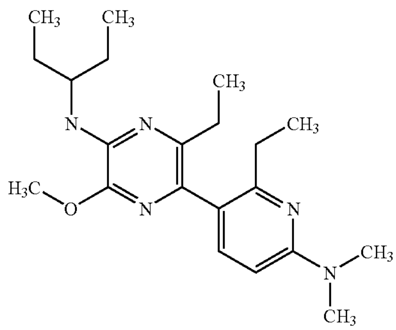 | 5-[6-(dimethylamino)-2-ethylpyridin-3-yl]-6-ethyl-N-(1-ethylpropyl)-3-methoxypyrazin-2-amine |
| 84 | 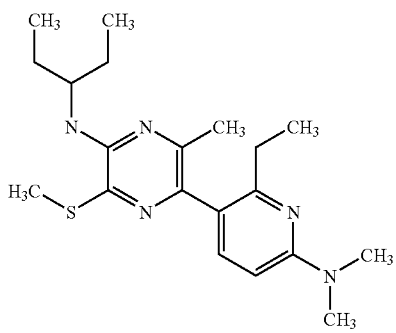 | 5-[6-(dimethylamino)-2-ethylpyridin-3-yl]-N-(1-ethylpropyl)-6-methyl-3-(methylthio)pyrazin-2-amine |
| 85 | 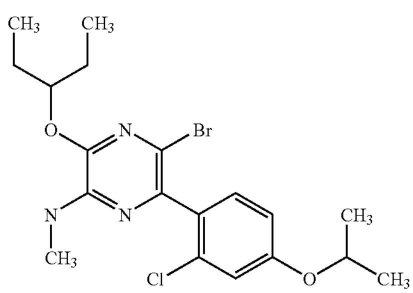 | 5-bromo-6-(2-chloro-4-isopropoxyphenyl)-3-(1-ethylpropoxy)-N-methylpyrazin-2-amine |
| 86 | 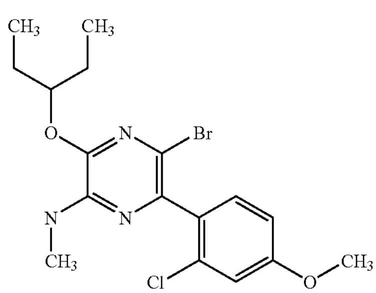 | 5-bromo-6-(2-chloro-4-methoxyphenyl)-3-(1-ethylpropoxy)-N-methylpyrazin-2-amine |
| 87 | 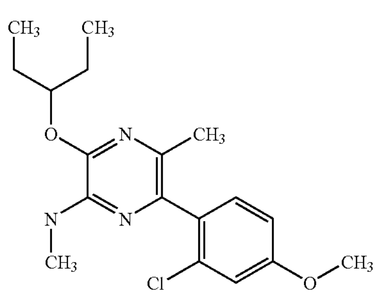 | 6-(2-chloro-4-methoxyphenyl)-3-(1-ethylpropoxy)-N,5-dimethylpyrazin-2-amine |

TABLE II-continued

| CMP # | STRUCTURE | IUPAC NAME |
|---|---|---|
| 88 | 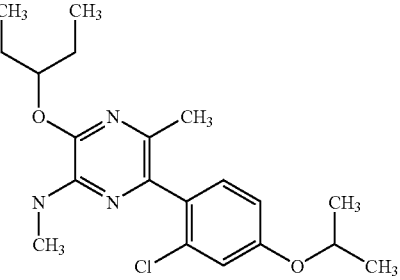 | 6-(2-chloro-4-isopropoxyphenyl)-3-(1-ethylpropoxy)-N,5-dimethylpyrazin-2-amine |
| 89 | 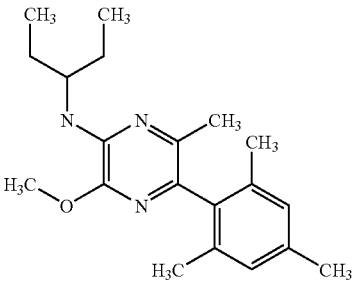 | N-(1-ethylpropyl)-5-mesityl-3-methoxy-6-methylpyrazin-2-amine |
| 90 | 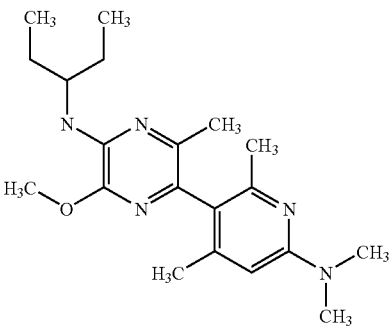 | 5-[6-(dimethylamino)-2,4-dimethylpyridin-3-yl]-N-(1-ethylpropyl)-3-methoxy-6-methylpyrazin-2-amine |
| 91 | 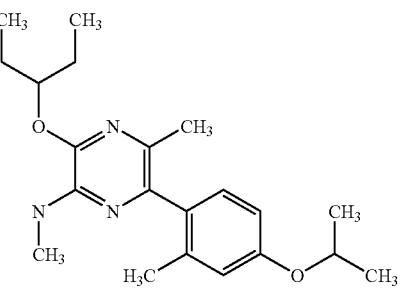 | 3-(1-ethylpropoxy)-6-(4-isopropoxy-2-methylphenyl)-N,5-dimethylpyrazin-2-amine |
| 92 | 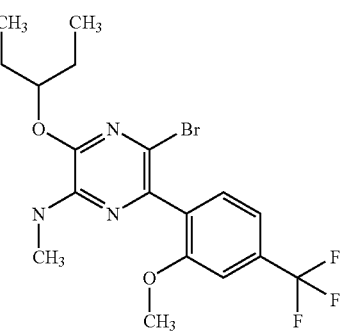 | 5-bromo-3-(1-ethylpropoxy)-6-[2-methoxy-4-(trifluoromethyl)phenyl]-N-methylpyrazin-2-amine |

TABLE II-continued

| CMP # | STRUCTURE | IUPAC NAME |
|---|---|---|
| 93 | 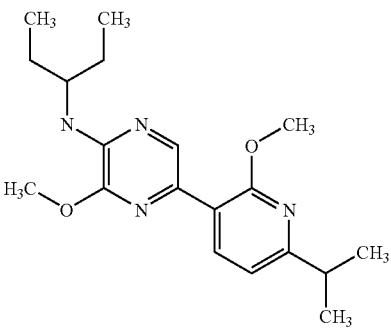 | N-(1-ethylpropyl)-5-(6-isopropyl-2-methoxypyridin-3-yl)-3-methoxypyrazin-2-amine |
| 94 | 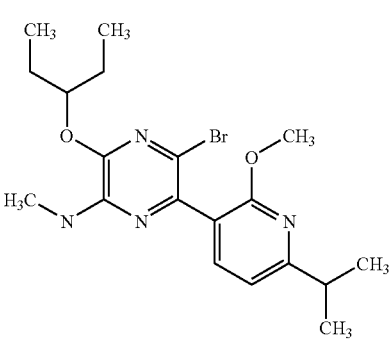 | 5-bromo-3-(1-ethylpropoxy)-6-(6-isopropyl-2-methoxypyridin-3-yl)-N-methylpyrazin-2-amine |
| 95 | 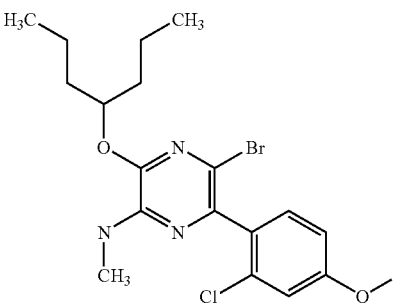 | 5-bromo-6-(2-chloro-4-methoxyphenyl)-N-methyl-3-(1-propylbutoxy)pyrazin-2-amine |
| 96 | 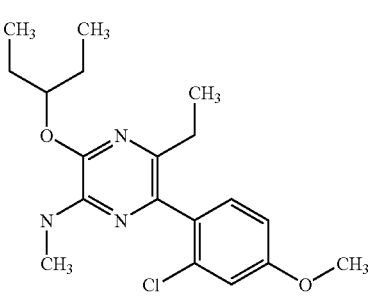 | 6-(2-chloro-4-methoxyphenyl)-5-ethyl-3-(1-ethylpropoxy)-N-methylpyrazin-2-amine |
| 97 | 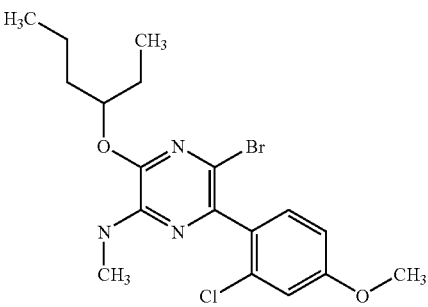 | 5-bromo-6-(2-chloro-4-methoxyphenyl)-3-(1-ethylbutoxy)-N-methylpyrazin-2-amine |

TABLE II-continued

| CMP # | STRUCTURE | | IUPAC NAME |
|---|---|---|---|
| 98 | 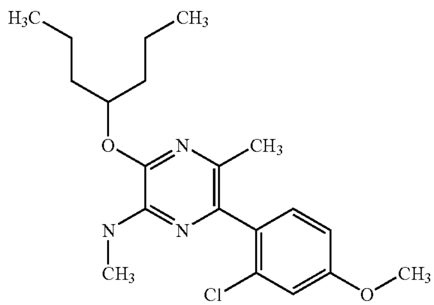 | | 6-(2-chloro-4-methoxyphenyl)-N,5-dimethyl-3-(1-propylbutoxy)pyrazin-2-amine |
| 99 | 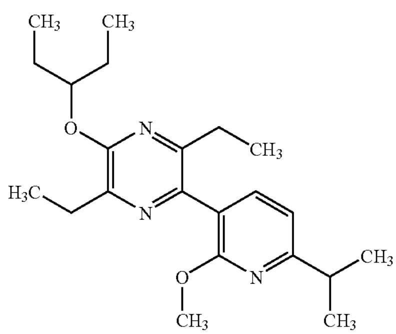 | | 2,5-diethyl-3-(1-ethylpropoxy)-6-(6-isopropyl-2-methoxypyridin-3-yl)pyrazine |
| 100 | 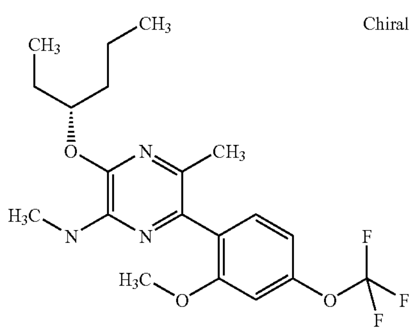 | Chiral | 3-{[(1R)-1-ethylbutyl]oxy}-6-[2-methoxy-4-(trifluoromethoxy)phenyl]-N,5-dimethylpyrazin-2-amine |
| 101 | 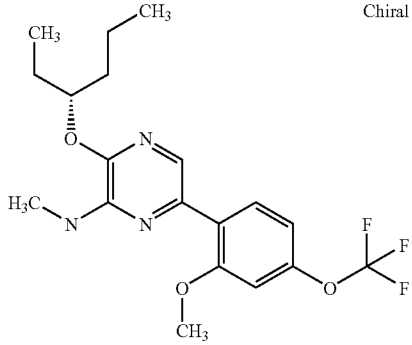 | Chiral | 3-{[(1R)-1-ethylbutyl]oxy}-6-[2-methoxy-4-(trifluoromethoxy)phenyl]-N-methylpyrazin-2-amine |

TABLE II-continued

| CMP # | STRUCTURE | | IUPAC NAME |
|---|---|---|---|
| 102 | (structure) | Chiral | 5-bromo-3-{[(1R)-1-ethylbutyl]oxy}-6-[2-methoxy-4-(trifluoromethoxy)phenyl]-N-methylpyrazin-2-amine |
| 103 | (structure) | Chiral | 3-{[(1S)-1-ethytbutyl]oxy}-6-[2-methoxy-4-(trifluoromethoxy)phenyl]-N,5-dimethylpyrazin-2-amine |
| 104 | (structure) | Chiral | 3-{[(1S)-1-ethylbutyl]oxy}-6-[2-methoxy-4-(trifluoromethoxy)phenyl]-N-methylpyrazin-2-amine |
| 105 | (structure) | Chiral | 5-bromo-3-{[(1S)-1-ethylbutyl]oxy}-6-[2-methoxy-4-(trifluoromethoxy)phenyl-]N-methylpyrazin-2-amine |

TABLE II-continued

| CMP # | STRUCTURE | IUPAC NAME |
|---|---|---|
| 106 | 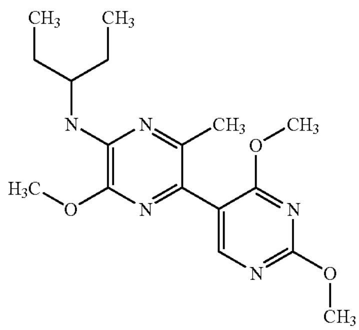 | 5-(2,4-dimethoxypyrimidin-5-yl)-N-(1-ethylpropyl)-3-methoxy-6-methylpyrazin-2-amine |
| 107 | 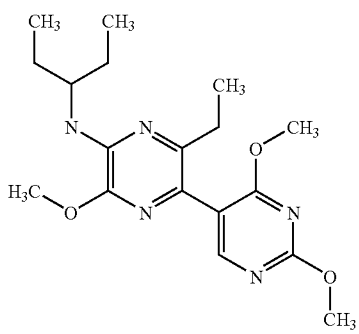 | 5-(2,4-dimethoxypyrimidin-5-yl)-6-ethyl-N-(1-ethylpropyl)-3-methoxypyrazin-2-amine |
| 108 | 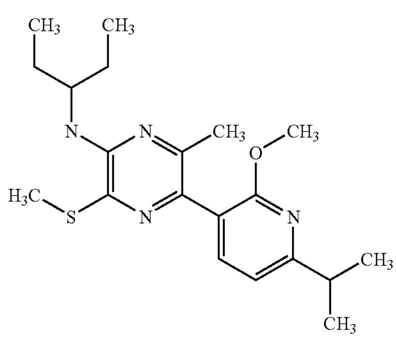 | N-(1-ethylpropyl)-5-(6-isopropyl-2-methoxypyridin-3-yl)-6-methyl-3-(methylthio)pyrazin-2-amine |
| 109 | 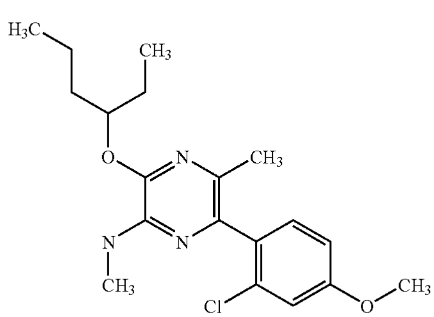 | 6-(2-chloro-4-methoxyphenyl)-3-(1-ethylbutoxy)-N,5-dimethylpyrazin-2-amine |

TABLE II-continued

| CMP # | STRUCTURE | IUPAC NAME |
|---|---|---|
| 110 | 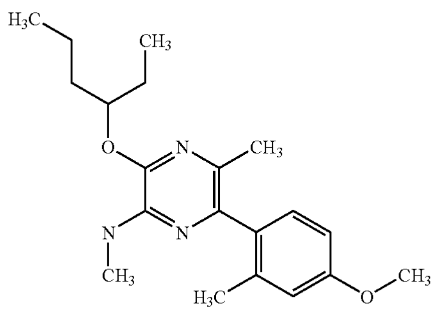 | 3-(1-ethylbutoxy)-6-(4-methoxy-2-methylphenyl)-N,5-dimethylpyrazin-2-amine |
| 111 | 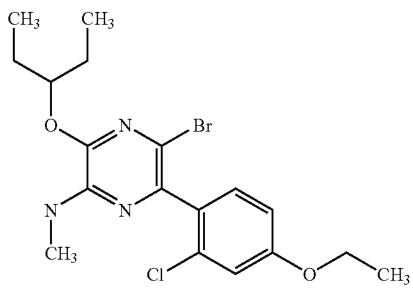 | 5-bromo-6-(2-chloro-4-ethoxyphenyl)-3-(1-ethylpropoxy)-N-methylpyrazin-2-amine |
| 112 | 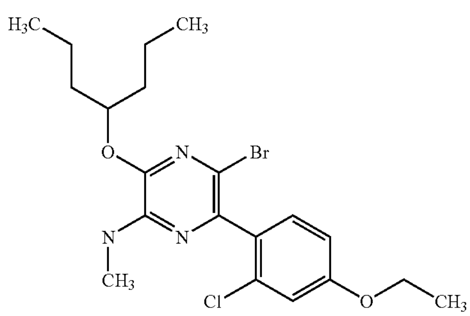 | 5-bromo-6-(2-chloro-4-ethoxyphenyl)-N-methyl-3-(1-propylbutoxy)pyrazin-2-amine |
| 113 | 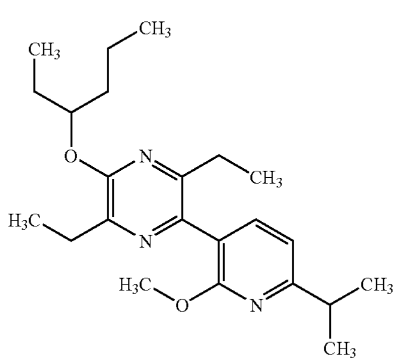 | 2,5-diethyl-3-(1-ethylbutoxy)-6-(6-isopropyl-2-methoxypyridin-3-yl)pyrazine |

TABLE II-continued

| CMP # | STRUCTURE | IUPAC NAME |
|---|---|---|
| 114 | 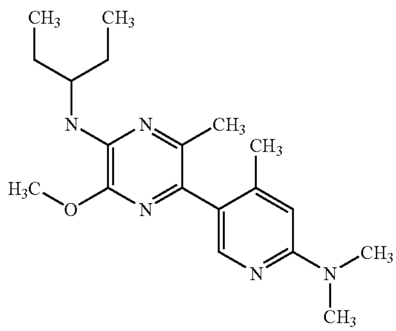 | 5-[6-(dimethylamino)-4-methylpyridin-3-yl]-N-(1-ethylpropyl)-3-methoxy-6-methylpyrazin-2-amine |
| 115 | 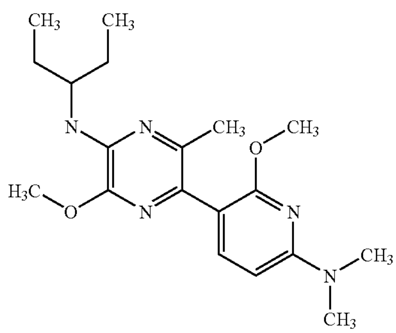 | 5-[6-(dimethylamino)-2-methoxypyridin-3-yl]-N-(1-ethylpropyl)-3-methoxy-6-methylpyrazin-2-amine |
| 116 | 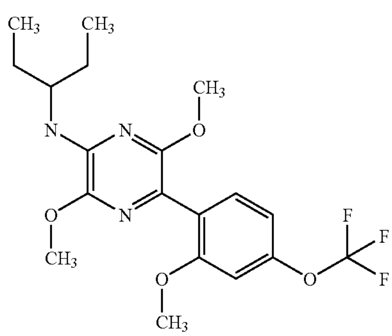 | N-(1-ethylpropyl)-3,6-dimethoxy-5-[2-methoxy-4-(trifluoromethoxy)phenyl]pyrazin-2-amine |
| 117 | 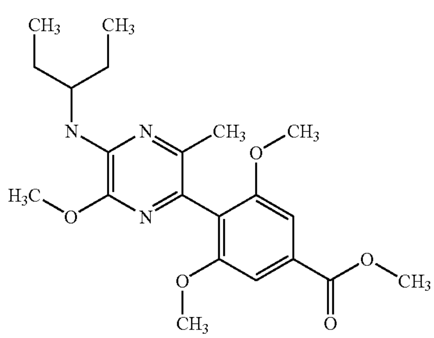 | methyl 4-{5-[(1-ethylpropyl)amino]-6-methoxy-3-methylpyrazin-2-yl}-3,5-dimethoxybenzoate |

TABLE II-continued

| CMP # | STRUCTURE | IUPAC NAME |
|---|---|---|
| 118 | 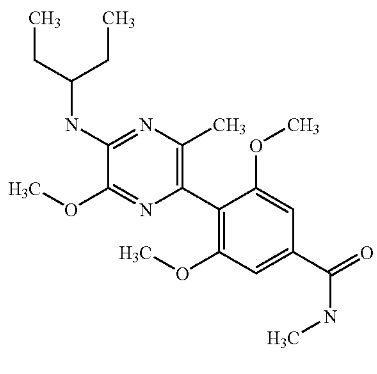 | 4-{5-[(1-ethylpropyl)amino]-6-methoxy-3-methylpyrazin-2-yl}-3,5-dimethoxy-N-methylbenzamide |
| 119 | 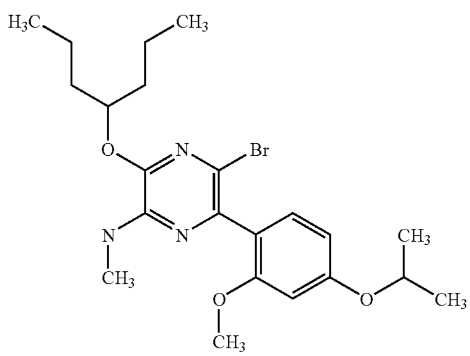 | 5-bromo-6-(4-isopropoxy-2-methoxyphenyl)-N-methyl-3-(1-propylbutoxy)pyrazin-2-amine |
| 120 | 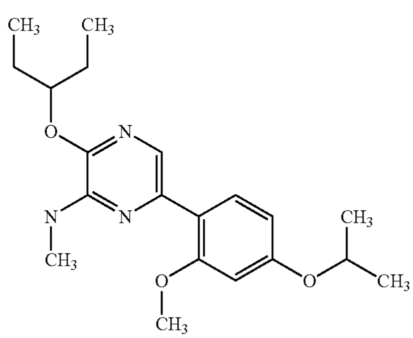 | 3-(1-ethylpropoxy)-6-(4-isopropoxy-2-methoxyphenyl)-N-metylpyrazin-2-amine |
| 121 | 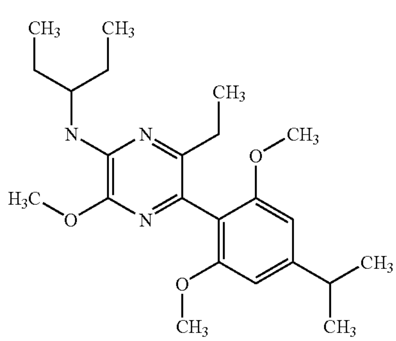 | 6-ethyl-N-(1-ethylpropyl)-5-(4-isopropyl-2,6-dimethoxyphenyl)-3-methoxypyrazin-2-amine |

TABLE II-continued

| CMP # | STRUCTURE | IUPAC NAME |
|---|---|---|
| 122 | 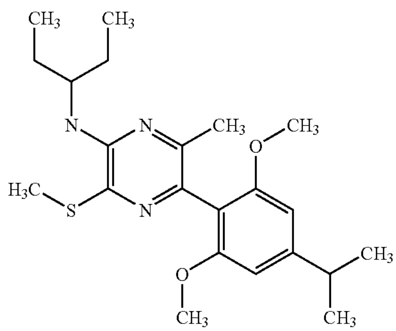 | N-(1-ethylpropyl)-5-(4-isopropyl-2,6-dimethoxyphenyl)-6-methyl-3-(methylthio)pyrazin-2-amine |
| 123 | 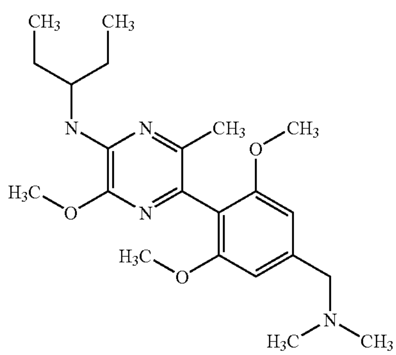 | 5-{4-[(dimethylamino)methyl]-2,6-dimethoxyphenyl}-N-(1-ethylpropyl)-3-methoxy-6-methylpyrazin-2-amine |
| 124 | 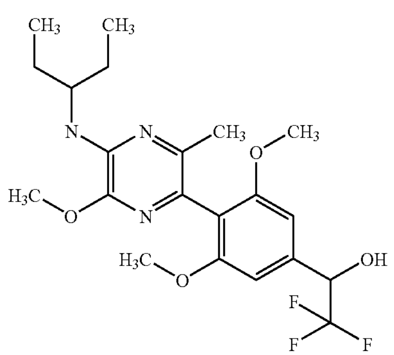 | 1-(4-{5-[(1-ethylpropyl)amino]-6-methoxy-3-methylpyrazin-2-yl}-3,5-dimethoxyphenyl)-2,2,2-trifluoroethanol |
| 125 | 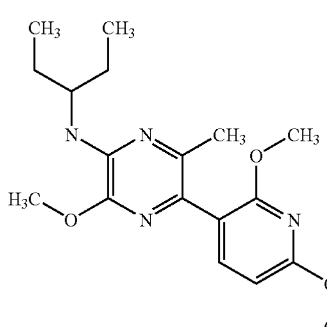 | 5-(2,6-dimethoxypyridin-3-yl)-N-(1-ethylpropyl)-3-methoxy-6-methylpyrazin-2-amine |

TABLE II-continued
| CMP # | STRUCTURE | IUPAC NAME |
|---|---|---|
| 126 | 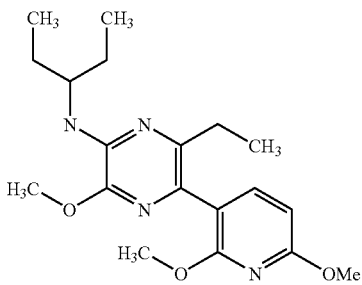 | 5-(2,6-dimethoxypyridin-3-yl)-6-ethyl-N-(1-ethylpropyl)-3-methoxypyrazin-2-amine |
| 127 | 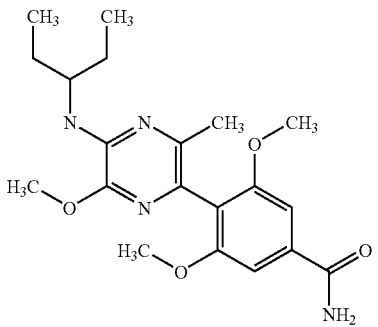 | 4-{5-[(1-ethylpropyl)amino]-6-methoxy-3-methylpyrazin-2-yl}-3,5-dimethoxybenzamide |
| 128 | 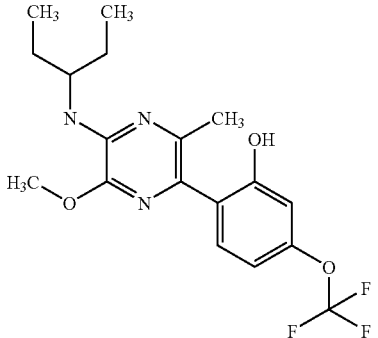 | 2-{5-[(1-ethylpropyl)amino]-6-methoxy-3-methylpyrazin-2-yl}-5-(trifluoromethoxy)phenol |
| 129 | 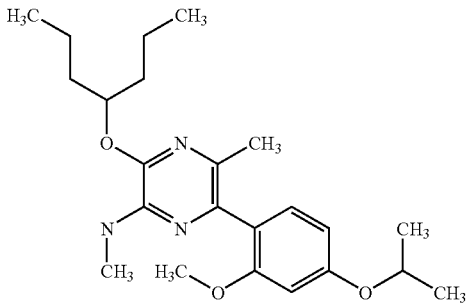 | 6-(4-isopropoxy-2-methoxyphenyl)-N,5-dimethyl-3-(1-propylbutoxy)pyrazin-2-amine |

TABLE II-continued
| CMP # | STRUCTURE | IUPAC NAME |
|---|---|---|
| 130 | 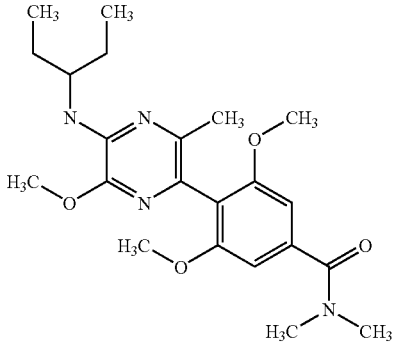 | 4-{5-[(1-ethylpropyl)amino]-6-methoxy-3-methylpyrazin-2-yl}-3,5-dimethoxy-N,N-dimethylbenzamide |
| 131 | 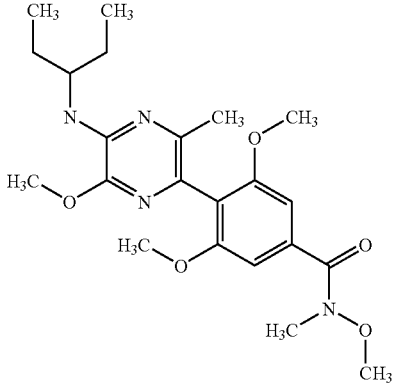 | 4-{5-[(1-ethylpropyl)amino]-6-methoxy-3-methylpyrazin-2-yl}-N,3,5-trimethoxy-N-methylbenzamide |
| 132 | 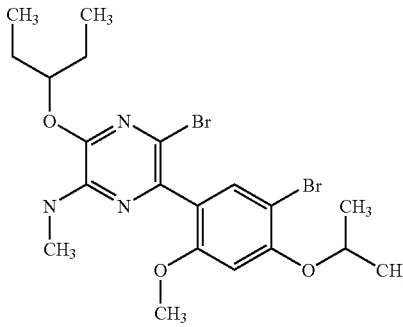 | 5-bromo-6-(5-bromo-4-isopropoxy-2-methoxyphenyl)-3-(1-ethylpropoxy)-N-methylpyrazin-2-amine |
| 133 | 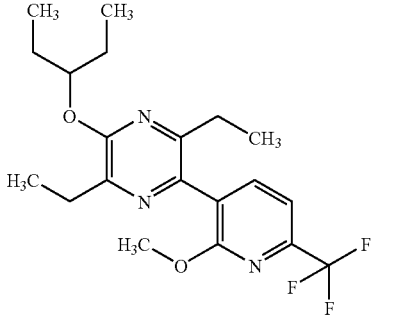 | 2,5-diethyl-3-(1-ethylpropoxy)-6-[2-methoxy-6-(trifluoromethyl)pyridin-3-yl]pyrazine |

TABLE II-continued

| CMP # | STRUCTURE | IUPAC NAME |
|---|---|---|
| 134 | 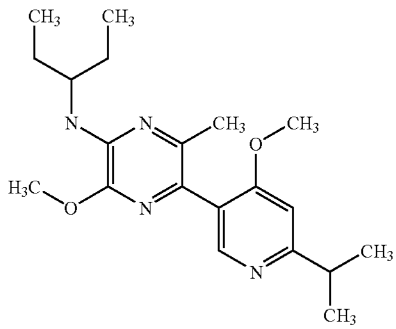 | N-(1-ethylpropyl)-5-(6-isopropyl-4-methoxypyridin-3-yl)-3-methoxy-6-methylpyrazin-2-amine |
| 135 | 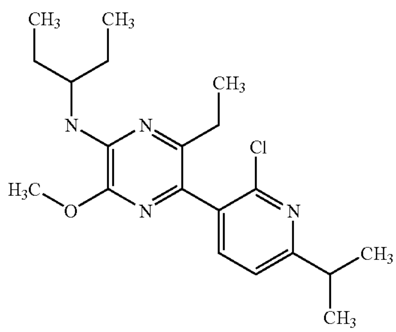 | 5-(2-chloro-6-isopropylpyridin-3-yl)-6-ethyl-N-(1-ethylpropyl)-3-methoxypyrazin-2-amine |
| 136 | 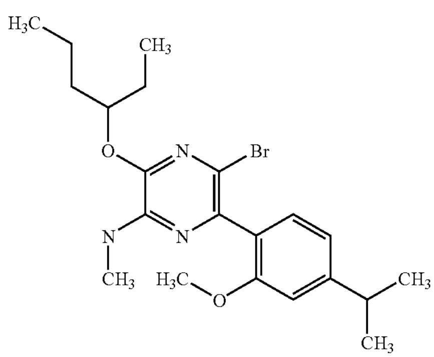 | 5-bromo-3-(1-ethylbutoxy)-6-(4-isopropyl-2-methoxyphenyl)-N-methylpyrazin-2-amine |
| 137 | 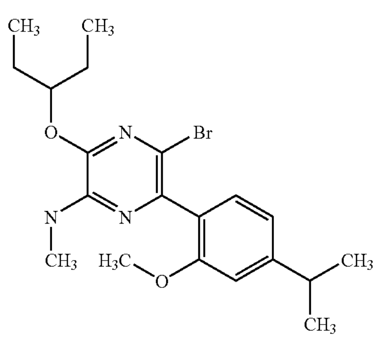 | 5-bromo-3-(1-ethylpropoxy)-6-(4-isopropyl-2-methoxyphenyl)-N-methylpyrazin-2-amine |

TABLE II-continued
| CMP # | STRUCTURE | IUPAC NAME |
|---|---|---|
| 138 | 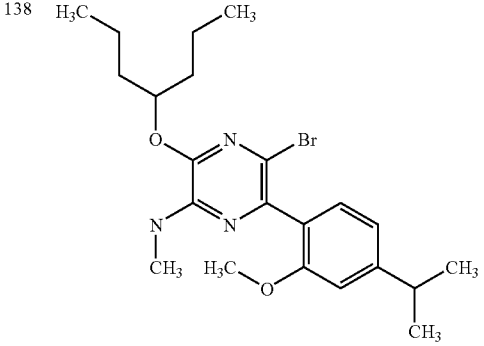 | 5-bromo-6-(4-isopropyl-2-methoxyphenyl)-N-methyl-3-(1-propylbutoxy)pyrazin-2-amine |
| 139 | 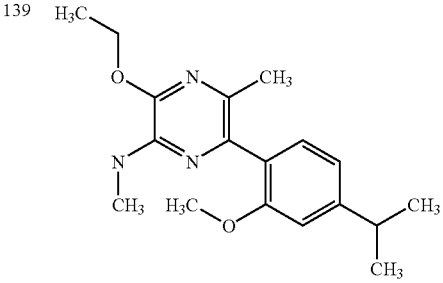 | 3-ethoxy-6-(4-isopropyl-2-methoxyphenyl)-N,5-dimethylpyrazin-2-amine |
| 140 | 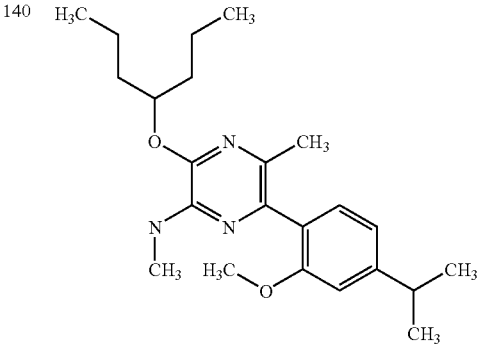 | 6-(4-isopropyl-2-methoxyphenyl)-N,5-dimethyl-3-(1-propylbutoxy)pyrazin-2-amine |
| 141 | 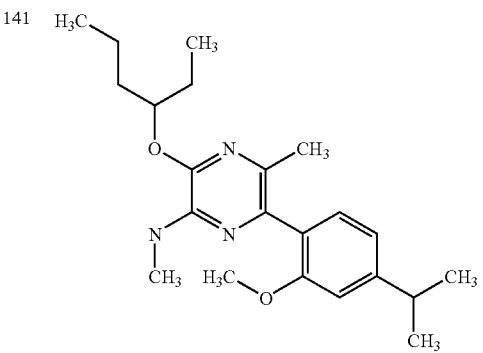 | 3-(1-ethylbutoxy)-6-(4-isopropyl-2-methoxyphenyl)-N,5-dimethylpyrazin-2-amine |

TABLE II-continued

| CMP # | STRUCTURE | IUPAC NAME |
|---|---|---|
| 142 | 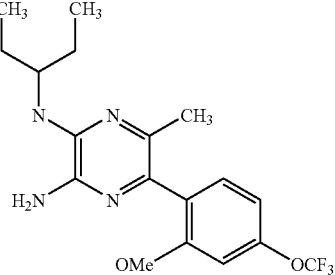 | $N^2$-(1-ethylpropyl)-5-[2-methoxy-4-(trifluoromethoxy)phenyl]-6-methylpyrazine-2,3-diamine |
| 143 | 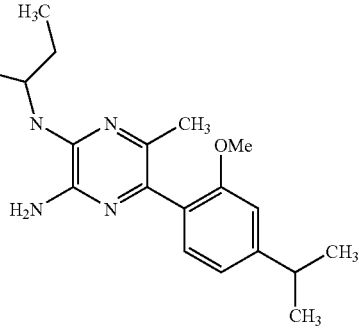 | $N^2$-(1-ethylpropyl)-5-(4-isopropyl-2-methoxyphenyl)-6-methylpyrazine-2,3-diamine |
| 144 | 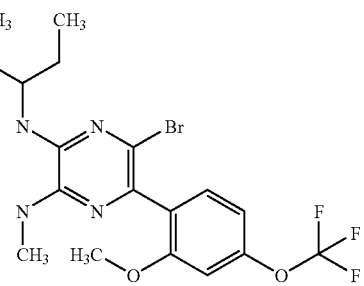 | 5-bromo-$N^3$-(1-ethylpropyl)-6-[2-methoxy-4-(trifluoromethoxy)phenyl]-$N^2$-methylpyrazine-2,3-diamine |
| 145 | 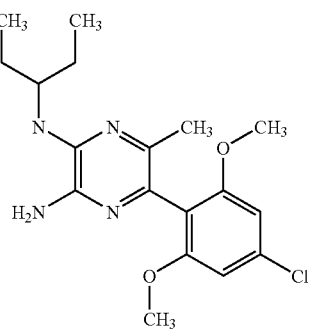 | 5-(4-chloro-2,6-dimethoxyphenyl)-$N^2$-(1-ethylpropyl)-6-methylpyrazine-2,3-diamine |
| 146 | 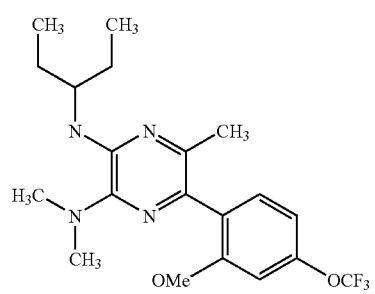 | $N^2$-(1-ethylpropyl)-5-[2-methoxy-4-(trifluoromethoxy)phenyl]-$N^3,N^3$,-6-trimethylpyrazine-2,3-diamine |

TABLE II-continued

| CMP # | STRUCTURE | IUPAC NAME |
|---|---|---|
| 147 | 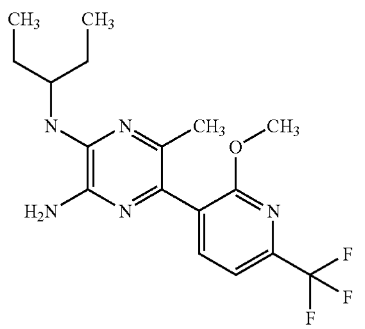 | $N^2$-(1-ethylpropyl)-5-[2-methoxy-6-(trifluoromethyl)pyridin-3-yl]-6-methylpyrazine-2,3-diamine |
| 148 | 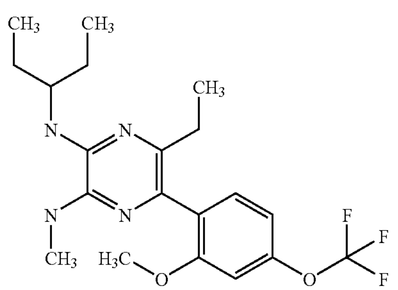 | 5-ethyl-$N^3$-(1-ethylpropyl)-6-[2-methoxy-4-(trifluoromethoxy)phenyl]-$N^2$-methylpyrazine-2,3-diamine |
| 149 | 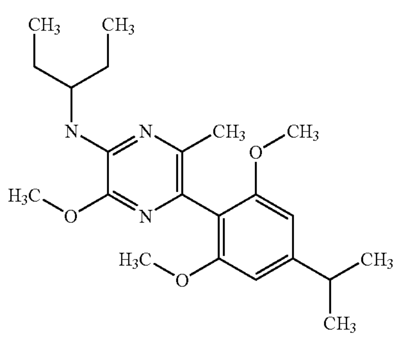 | N-(1-ethylpropyl)-5-(4-isopropyl-2,6-dimethoxyphenyl)-3-methoxy-6-methylpyrazin-2-amine |
| 150 | 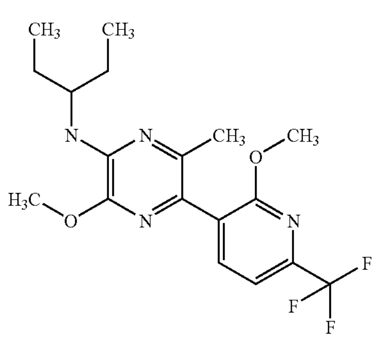 | N-(1-ethylpropyl)-3-methoxy-5-[(2-methoxy-6-(trifluoromethyl)pyridin-3-yl]-6-methylpyrazin-2-amine |

TABLE II-continued

| CMP # | STRUCTURE | IUPAC NAME |
|---|---|---|
| 151 | 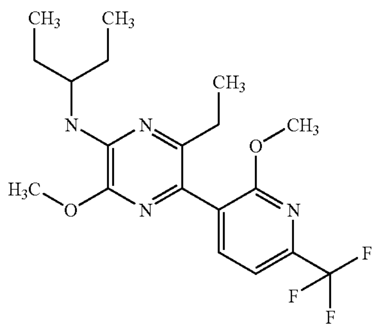 | 6-ethyl-N-(1-ethylpropyl)-3-methoxy-5-[2-methoxy-6-(trifluoromethyl)pyridin-3-yl]pyrazin-2-amine |
| 152 | 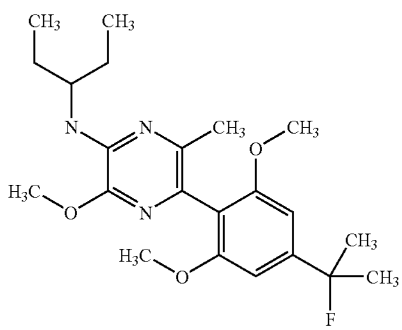 | N-(1-ethylpropyl)-5-[4-(1-fluoro-1-methylethyl)-2,6-dimethoxyphenyl]-3-methoxy-6-methylpyrazin-2-amine |
| 153 | 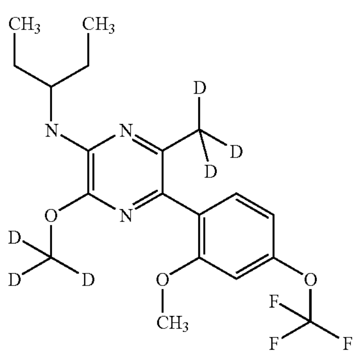 | N-(1-ethylpropyl)-3-methoxy-5-[2-methoxy-4-(trifluoromethoxy)phenyl]-6-methylpyrazin-2-amine d_6_ |
| 154 | 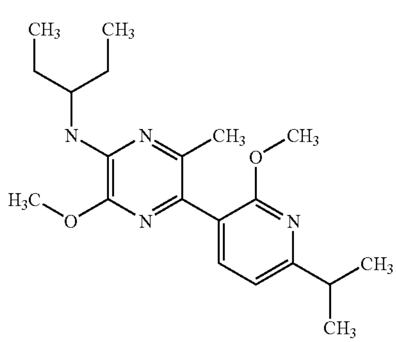 | N-(1-ethylpropyl)-5-(6-isopropyl-2-methoxypyridin-3-yl)-3-methoxy-6-methylpyrazin-2-amine |

TABLE II-continued

| CMP # | STRUCTURE | IUPAC NAME |
|---|---|---|
| 155 | 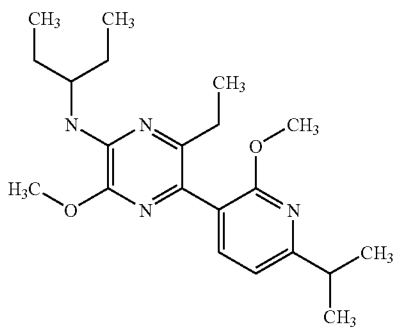 | 6-ethyl-N-(1-ethylpropyl)-5-(6-isopropyl-2-methoxypyridin-3-yl)-3-methoxypyrazin-2-amine |
| 156 | 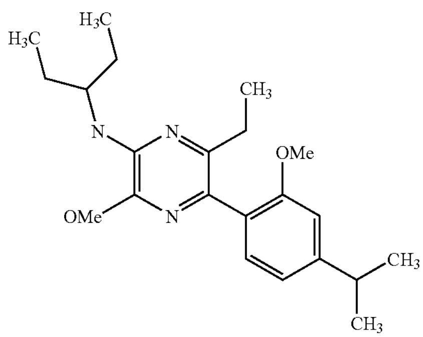 | 6-ethyl-N-(1-ethylpropyl)-5-(4-isopropyl-2-methoxyphenyl)-3-methoxypyrazin-2-amine |
| 157 | 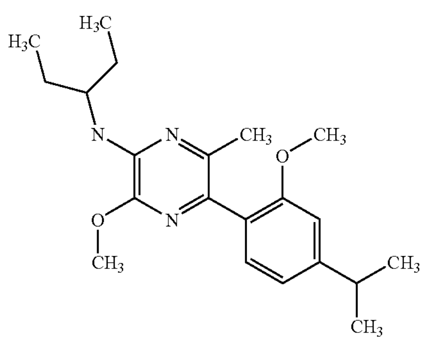 | N-(1-ethylpropyl)-5-(4-isopropyl-2-methoxyphenyl)-3-methoxy-6-methylpyrazin-2-amine |
| 158 | 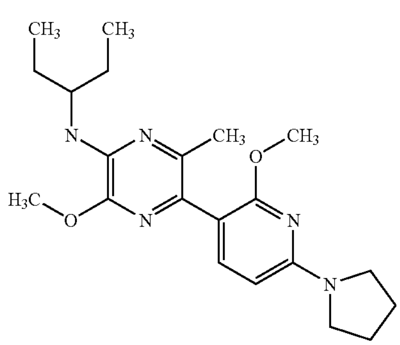 | N-(1-ethylpropyl)-3-methoxy-5-(2-methoxy-6-pyrrolidin-1-ylpyridin-3-yl)-6-methylpyrazin-2-amine |

TABLE II-continued

| CMP # | STRUCTURE | IUPAC NAME |
|---|---|---|
| 159 | 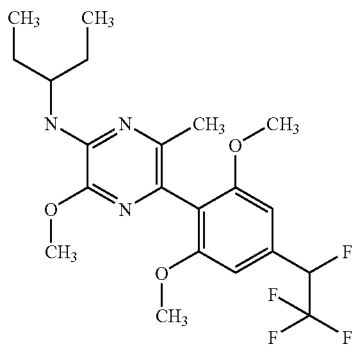 | 5-[2,6-dimethoxy-4-(1,2,2,2-tetrafluoroethyl)phenyl]-N-(1-ethylpropyl)-3-methoxy-6-methylpyrazin-2-amine |
| 160 | 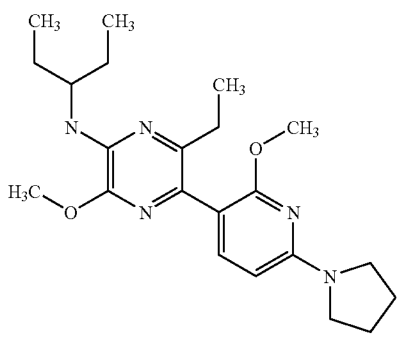 | 6-ethyl-N-(1-ethylpropyl)-3-methoxy-5-(2-methoxy-6-pyrrolidin-1-ylpyridin-3-yl)pyrazin-2-amine |
| 161 | 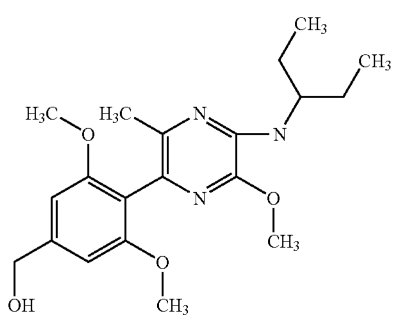 | (4-{5-[(1-ethylpropyl)amino]-6-methoxy-3-methylpyrazin-2-yl}-3,5-dimethoxyphenyl)methanol |
| 162 | 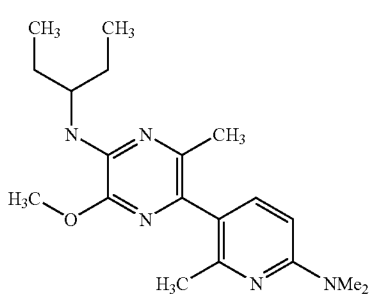 | 5-[6-(dimethylamino)-2-methylpyridin-3-yl]-N-(1-ethylpropyl)-3-methoxy-6-methylpyrazin-2-amine |

TABLE II-continued

| CMP # | STRUCTURE | IUPAC NAME |
|---|---|---|
| 163 | 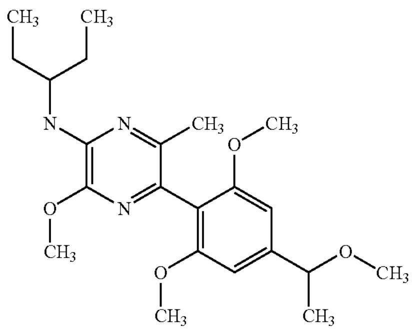 | 5-[2,6-dimethoxy-4-(1-methoxyethyl)phenyl]-N-(1-ethylpropyl)-3-methoxy-6-methylpyrazin-2-amine |
| 164 | 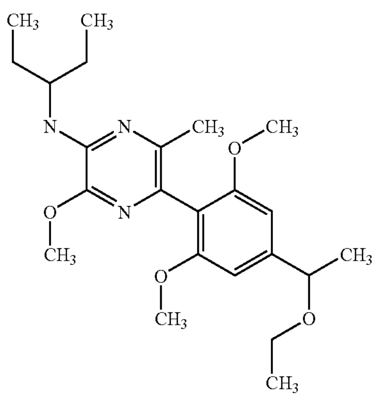 | 5-[4-(1-ethoxyethyl)-2,6-dimethoxyphenyl]-N-(1-ethylpropyl)-3-methoxy-6-methylpyrazin-2-amine |
| 165 | 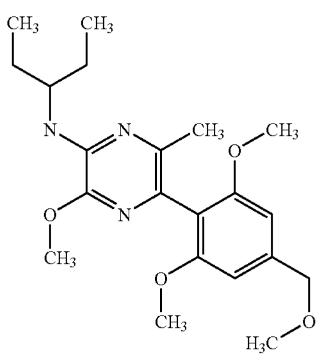 | 5-[2,6-dimethoxy-4-(methoxymethyl)phenyl]-N-(1-ethylpropyl)-3-methoxy-6-methylpyrazin-2-amine |
| 166 | 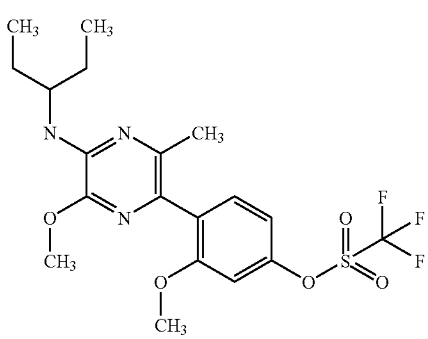 | 4-{5-[(1-ethylpropyl)amino]-6-methoxy-3-methylpyrazin-2-yl}-3-methoxyphenyl trifluoromethanesulfonate |

TABLE II-continued

| CMP # | STRUCTURE | IUPAC NAME |
|---|---|---|
| 167 | 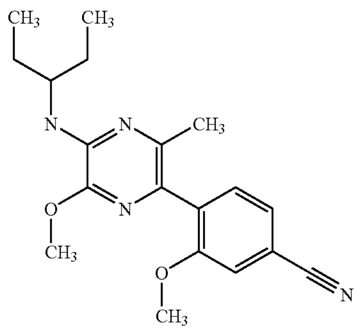 | 4-{5-[(1-ethylpropyl)amino]-6-methoxy-3-methylpyrazin-2-yl}-3-methoxybenzonitrile |
| 168 | 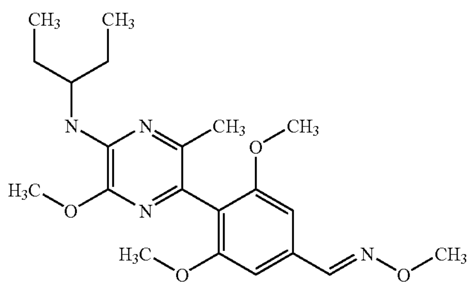 | 4-{5-[(1-ethylpropyl)amino]-6-methoxy-3-methylpyrazin-2-yl}-3,5-dimethoxybenzaldehyde O-methyloxime |
| 169 | 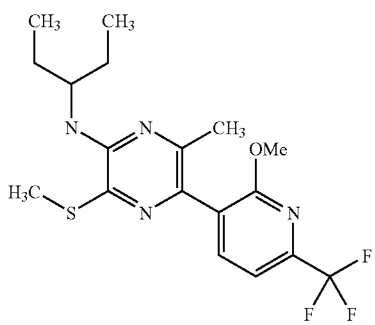 | N-(1-ethylpropyl)-5-[2-methoxy-6-(trifluoromethyl)pyridin-3-yl]-6-methyl-3-(methylthio)pyrazin-2-amine |
| 170 | 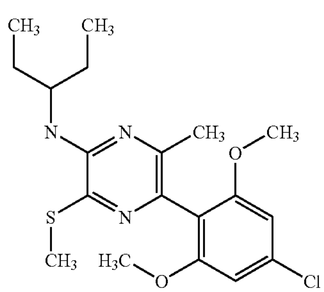 | 5-(4-chloro-2,6-dimethoxyphenyl)-N-(1-ethylpropyl)-6-methyl-3-(methylthio)pyrazin-2-amine |
| 171 | 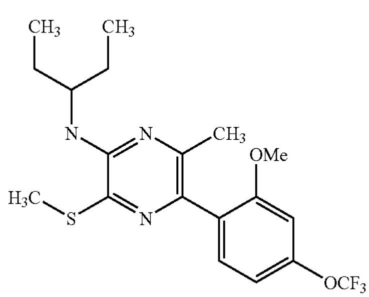 | N-(1-ethylpropyl)-5-[2-methoxy-4-(trifluoromethoxy)phenyl]-6-methyl-3-(methylthio)pyrazin-2-amine |

TABLE II-continued

| CMP # | STRUCTURE | IUPAC NAME |
|---|---|---|
| 172 | 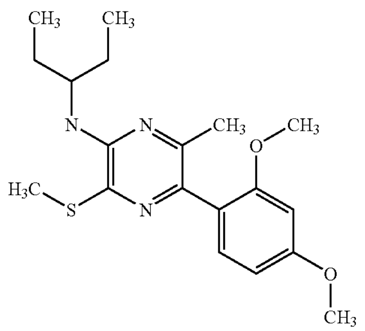 | 5-(2,4-dimethoxyphenyl)-N-(1-ethylpropyl)-6-methyl-3-(methylthio)pyrazin-2-amine |
| 173 | 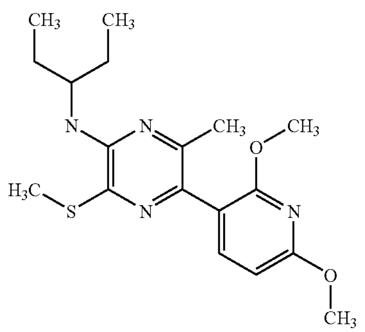 | 5-(2,6-dimethoxypyridin-3-yl)-N-(1-ethylpropyl)-6-methyl-3-(methylthio)pyrazin-2-amine |
| 174 | 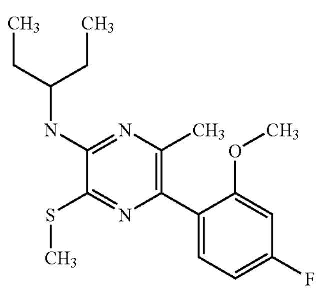 | N-(1-ethylpropyl)-5-(4-fluoro-2-methoxyphenyl)-6-methyl-3-(methylthio)pyrazin-2-amine |
| 175 | 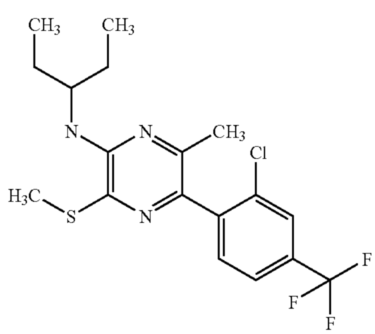 | 5-[2-chloro-4-(trifluoromethyl)phenyl]-N-(1-ethylpropyl)-6-methyl-3-(methylthio)pyrazin-2-amine |
| 176 | 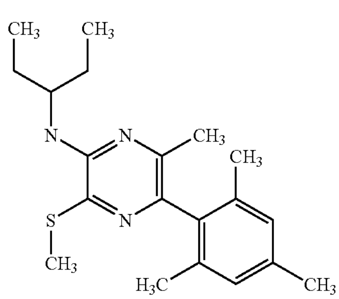 | N-(1-ethylpropyl)-5-mesityl-6-methyl-3-(methylthio)pyrazin-2-amine |

TABLE III

| Compound # | Structure | IUPAC Name |
|---|---|---|
| 177 | 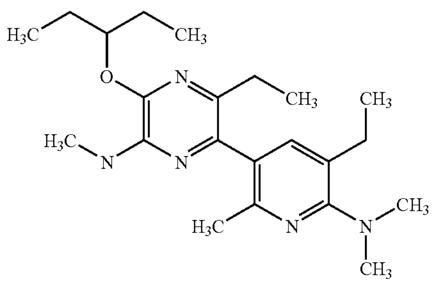 | [6-(6-Dimethylamino-4-ethyl-2-methyl-pyridin-3-yl)-5-ethyl-3-(1-ethyl-propoxy)-pyrazin-2-yl]-methyl-amine |
| 178 | 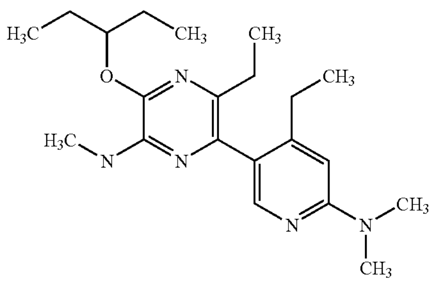 | [6-(6-Dimethylamino-4-ethyl-pyridin-3-yl)-5-ethyl-3-(1-ethyl-propoxy)-pyrazin-2-yl]-methyl-amine |
| 179 | 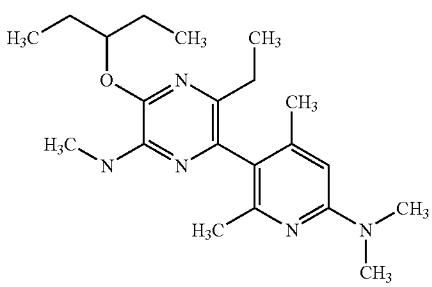 | [5-Ethyl-6-[2-(ethyl-methyl-amino)-6-isopropyl-pyridin-3-yl]-3-(1-ethyl-propoxy)-pyrazin-yl]-methyl-amine |
| 180 | 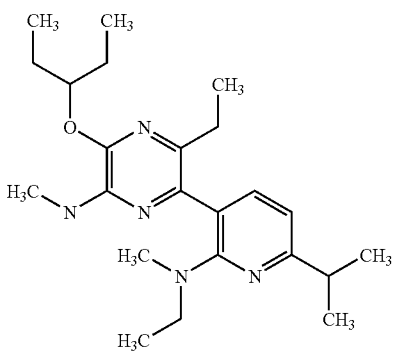 | [5-Ethyl-6-[2(ethyl-methyl-amino)-6-isopropyl-pyridin-3-yl]-3-(1-ethyl-propoxy)-pyrazin-2-yl]-methyl-amine |
| 181 | 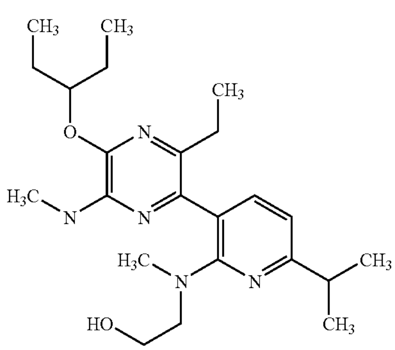 | 2-({3-[3-Ethyl-5-(1-ethyl-propoxy)-6-methylamino-pyrazin-2-yl]-6-isopropyl-pyridin-2-yl}-methyl-amino)-ethanol |

TABLE III-continued

| Compound # | Structure | IUPAC Name |
|---|---|---|
| 182 | 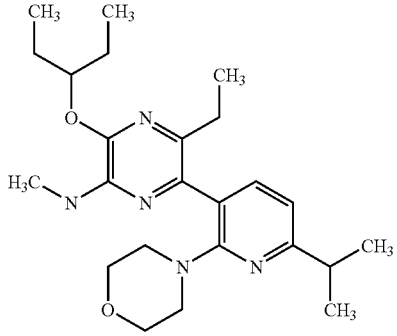 | [5-Ethyl-3-(1-ethyl-propoxy)-6-(6-isopropyl-2-morpholin-4-yl-pyridin-3-yl)-pyrazin-2-yl]-methyl-amine |
| 183 | 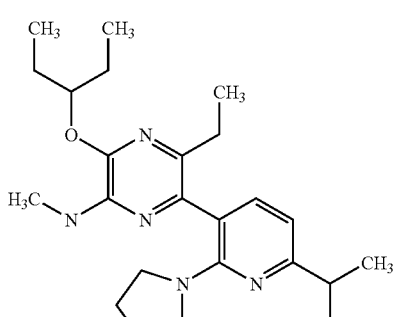 | [5-Ethyl-3-(1-ethyl-propoxy)-6-(6-isopropyl-2-pyrrolidin-1-yl-pyridin-3-yl)-pyrazin-2-yl]-methyl-amine |
| 184 | 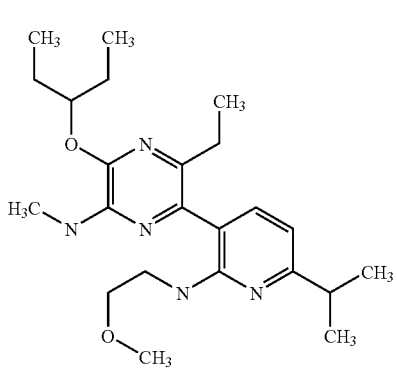 | {5-Ethyl-3-(1-ethyl-propoxy)-6-[6-isopropyl-2-(2-methoxy-ethylamino)-pyridin-3-yl]-pyrazin-2-yl}-methyl-amine |
| 185 | 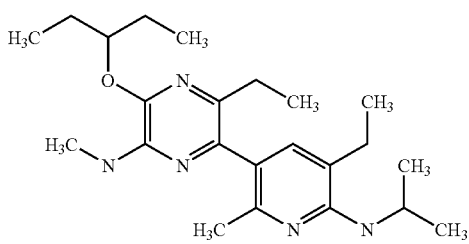 | [5-Ethyl-6-(5-ethyl-6-isopropylamino-2-methyl-pyridin-3-yl)-3-(1-ethyl-propoxy)-pyrazin-2-yl]-methyl-amine |

TABLE III-continued

| Compound # | Structure | IUPAC Name |
|---|---|---|
| 186 | 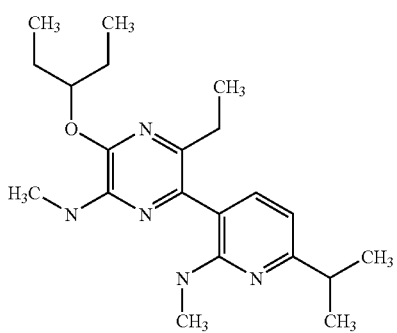 | [5-Ethyl-3-(1-ethyl-propoxy)-6-(6-isopropyl-2-methylamino-pyridin-3-yl)-pyrazin-2-yl]-methyl-amine |
| 187 | 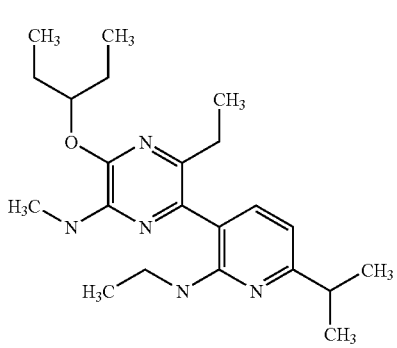 | [5-Ethyl-6-(2-ethylamino-6-isopropyl-pyridin-3-yl)-3-(1-ethyl-propoxy)-pyrazin-2-yl]-methyl-amine |
| 188 | 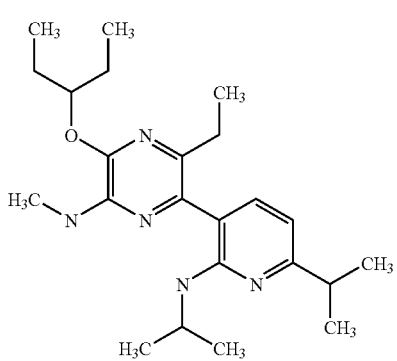 | [5-Ethyl-3-(1-ethyl-propoxy)-6-(6-isopropyl-2-isopropylamino-pyridin-3-yl)-pyrazin-2-yl]-methyl-amine |
| 189 | 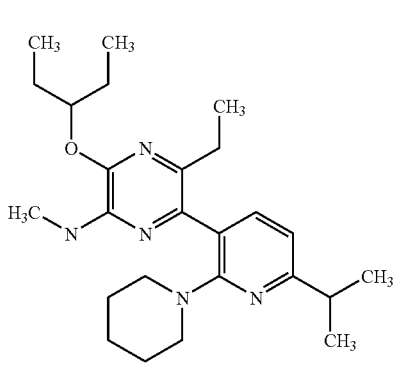 | [5-Ethyl-3-(1-ethyl-propoxy)-6-(6'-isopropyl-3,4,5,6-tetrahydro-2H-[1,2']bipyridinyl-3'-yl)-pyrazin-2-yl]-methyl-amine |

TABLE III-continued

| Compound # | Structure | IUPAC Name |
|---|---|---|
| 190 | 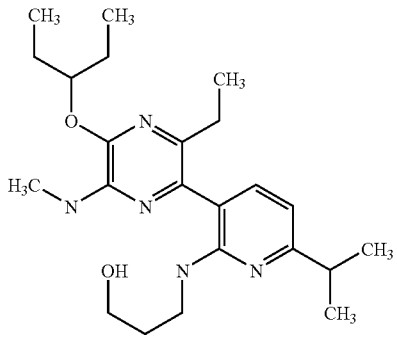 | 3-{3-[3-Ethyl-5-(1-ethyl-propoxy)-6-methylamino-pyrazin-2-yl]-6-isopropyl-pyridin-2-ylamino}-propan-1-ol |
| 191 | 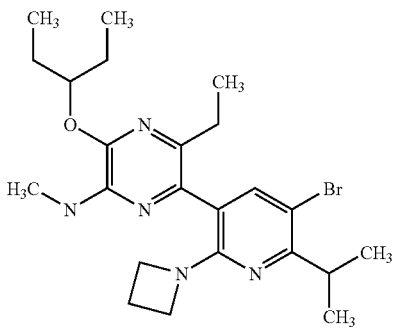 | [6-(2-Azetidin-1-yl-5-bromo-6-isopropyl-pyridin-3-yl)-5-ethyl-3-(1-ethyl-propoxy)-pyrazin-2-yl]-methyl-amine |
| 192 | 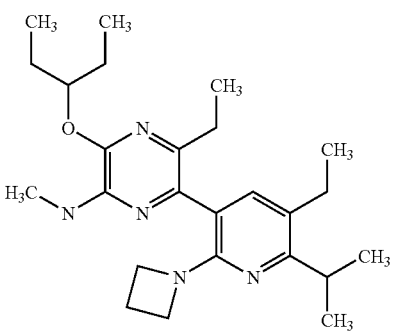 | [6-(2-Azetidin-1-yl-5-ethyl-6-isopropyl-pyridin-3-yl)-5-ethyl-3-(1-ethyl-propoxy)-pyrazin-2-yl]-methyl-amine |
| 193 | 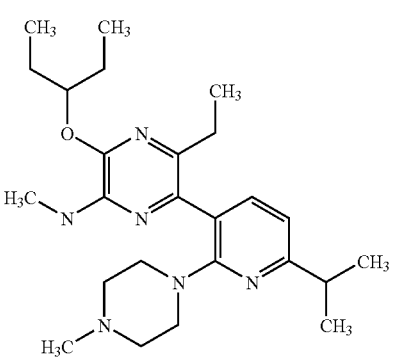 | {5-Ethyl-3-(1-ethyl-propoxy)-6-[6-isopropyl-2-(4-methyl-piperazin-1-yl)-pyridin-3-yl]-pyrazin-2-yl}-methyl-amine |

TABLE III-continued

| Compound # | Structure | IUPAC Name |
|---|---|---|
| 194 | 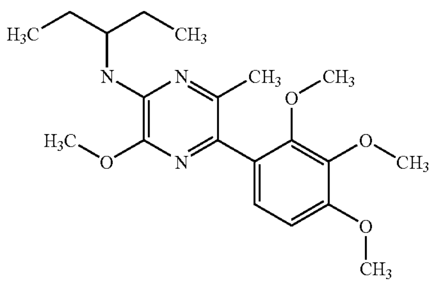 | (1-Ethyl-propyl)-[3-methoxy-6-methyl-5-(2,3,4-trimethoxy-phenyl)-pyrazin-2-yl]-amine |
| 195 | 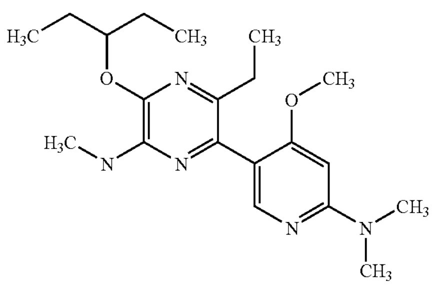 | [6-(6-Dimethylamino-4-methoxy-pyridin-3-yl)-5-ethyl-3-(1-ethyl-propoxy)-pyrazin-2-yl]-methyl-amine |
| 196 | 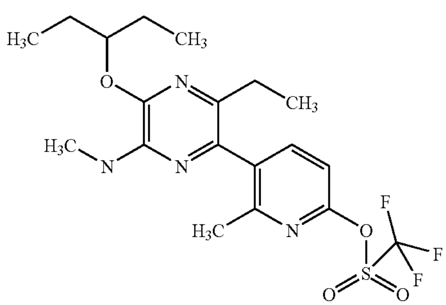 | Trifluoro-methanesulfonic acid 5-[3-ethyl-5-(1-ethyl-propoxy)-6-methylamino-pyrazin-2-yl]-6-methyl-pyridin-2-yl ester |
| 197 | 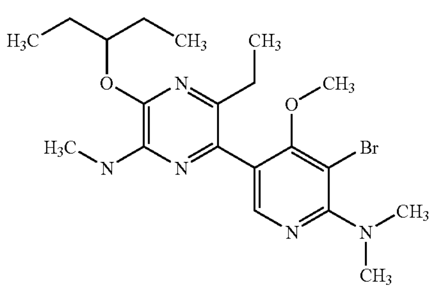 | [6-(5-Bromo-6-dimethylamino-4-methoxy-pyridin-3-yl)-5-ethyl-3-(1-ethyl-propoxy)-pyrazin-2-yl]-methyl-amine |
| 198 | 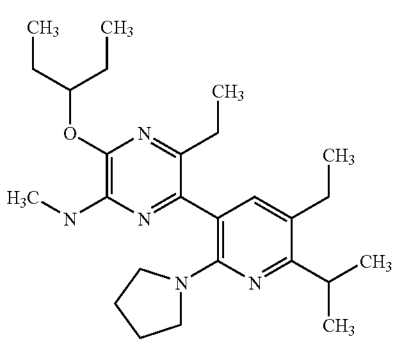 | [5-Ethyl-6-(5-ethyl-6-isopropyl-2-pyrrolidin-1-yl-pyridin-3-yl)-3-(1-ethyl-propoxy)-pyrazin-2-yl]-methyl-amine |

TABLE III-continued

| Compound # | Structure | IUPAC Name |
|---|---|---|
| 199 | 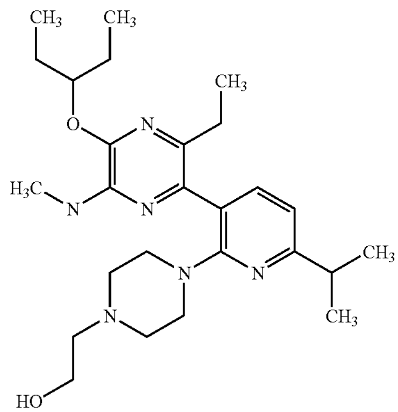 | 2-(4-{3-[3-Ethyl-5-(1-ethyl-propoxy)-6-methylamino-pyrazin-2-yl]-6-isopropyl-pyridin-2-yl}-piperazin-1-yl)-ethanol |
| 200 | 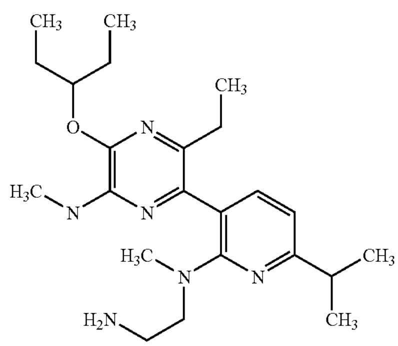 | N1-{3-[3-Ethyl-5-(1-ethyl-propoxy)-6-methylamino-pyrazin-2-yl]-6-isopropyl-pyridin-2-yl}-N1-methyl-ethane-1,2-diamine |
| 201 | 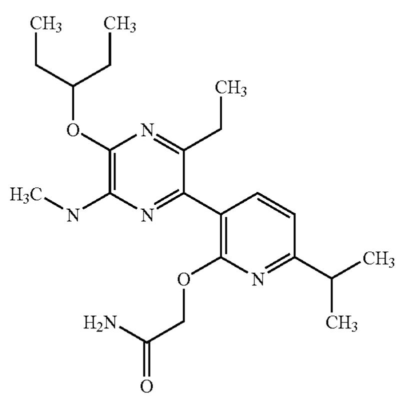 | 2-{3-[3-Ethyl-5-(1-ethyl-propoxy)-6-methylamino-pyrazin-2-yl]-6-isopropyl-pyridin-2-yloxy}-acetamide |
| 202 | 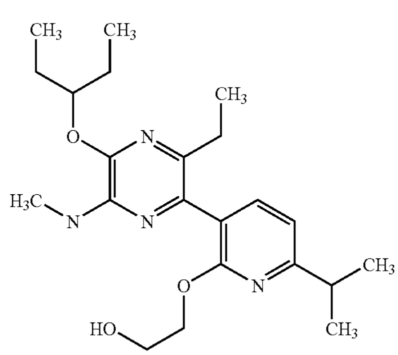 | 2-{3-[3-Ethyl-5-(1-ethyl-propoxy)-6-methylamino-pyrazin-2-yl]-6-isopropyl-pyridin-2-yloxy}-ethanol |

TABLE III-continued

| Compound # | Structure | IUPAC Name |
|---|---|---|
| 203 | 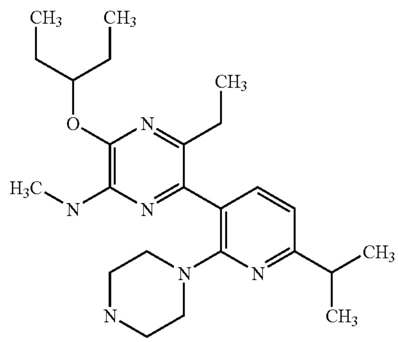 | [5-Ethyl-3-(1-ethyl-propoxy)-6-(6-isopropyl-2-piperazin-1-yl-pyridin-3-yl)-pyrazin-2-yl]-methyl-amine |
| 204 | 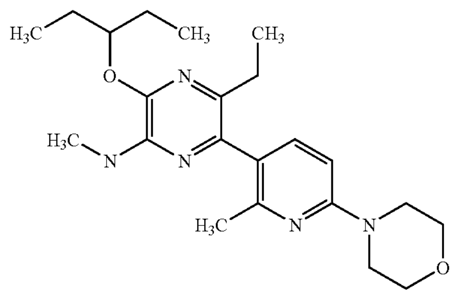 | [5-Ethyl-3-(1-ethyl-propoxy)-6-(2-methyl-6-morpholin-4-yl-pyridin-3-yl)-pyrizin-2-yl]-methyl-amine |
| 205 | 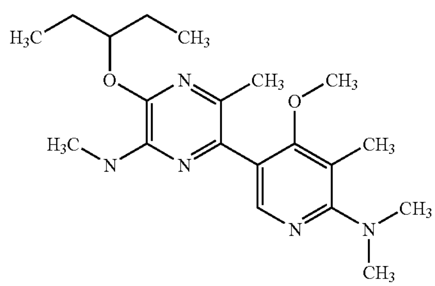 | [6-(6-Dimethylamino-4-methoxy-5-methyl-pyridin-3-yl)-3-(1-ethyl-propoxy)-5-methyl-pyrazin-2-yl]-methyl-amine |
| 206 | 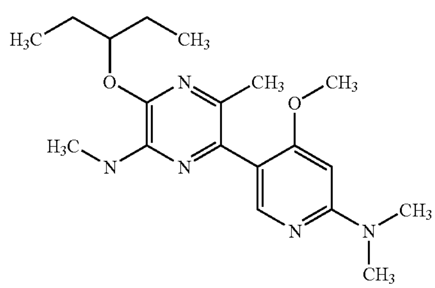 | [6-(6-Dimethylamino-4-methoxy-pyridin-3-yl)-3-(1-ethyl-propoxy)-5-methyl-pyrazin-2-yl]-methyl-amine |
| 207 | 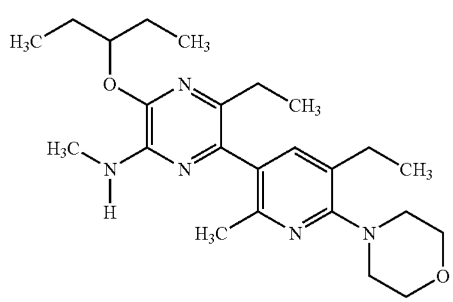 | [5-Ethyl-6-(5-ethyl-2-methyl-6-morpholin-4-yl-pyridin-3-yl)-3-(1-ethyl-propoxy)-pyrazin-2-yl]-methyl-amine |

TABLE III-continued

| Compound # | Structure | IUPAC Name |
|---|---|---|
| 208 | 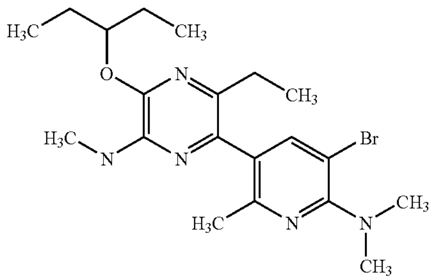 | [6-(5-Bromo-6-dimethylamino-2-methyl-pyridin-3-yl)-5-ethyl-3-(1-ethyl-propoxy)-pyrazin-2-yl]-methyl-amine |
| 209 | 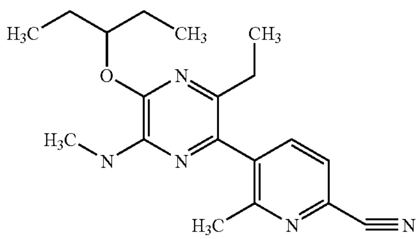 | [5-[3-Ethyl-5-(1-ethyl-propoxy)-6-methylamino-pyrazin-2-yl]-6-methyl-pyridine-2-carbonitrile |
| 210 | 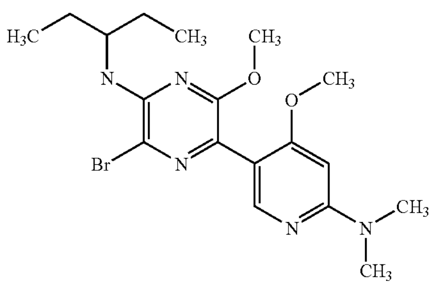 | [3-Bromo-5-(6-dimethylamino-4-methoxy-pyridin-3-yl)-6-methoxy-pyrazin-2-yl]-(1-ethyl-propyl)-amine |
| 211 | 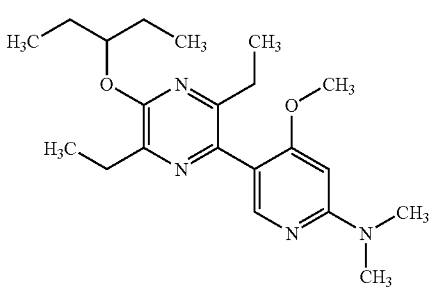 | {5-[3,6-Diethyl-5-(1-ethyl-propoxy)-pyrazin-2-yl]-4-methoxy-pyridin-2-yl}-dimethyl-amine |
| 212 | 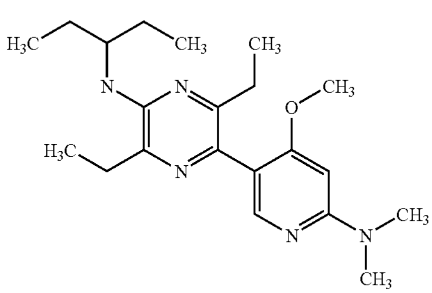 | [5-(6-Dimethylamino-4-methoxy-pyridin-3-yl)-3,6-diethyl-pyrazin-2-yl]-(1-ethyl-propyl)-amine |

TABLE III-continued

| Compound # | Structure | IUPAC Name |
|---|---|---|
| 213 | 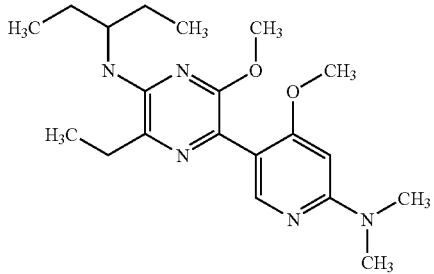 | [5-(6-Dimethylamino-4-methoxy-pyridin-3-yl)-3-ethyl-6-methoxy-pyrazin-2-yl]-(1-ethyl-propyl)-amine |
| 214 | 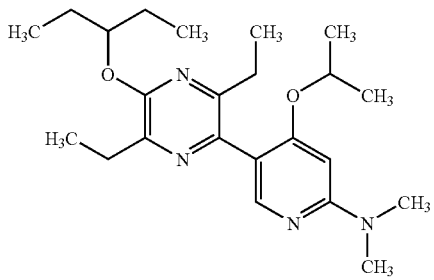 | {5-[3,6-Diethyl-5-(1-ethyl-propoxy)-pyrazin-2-yl]-4-isopropoxy-pyridin-2-yl}-dimethyl-amine |
| 215 | 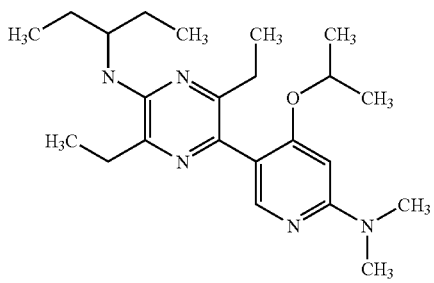 | [5-(6-Dimethylamino-4-isopropoxy-pyridin-3-yl)-3,6-diethyl-pyrazin-2-yl]-(1-ethyl-propyl)-amine |
| 216 | 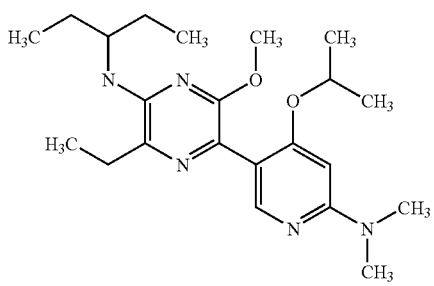 | [5-(6-Dimethylamino-4-isopropoxy-pyridin-3-yl)-3-ethyl-6-methoxy-pyrazin-2-yl]-(1-ethyl-propyl)-amine |
| 217 | 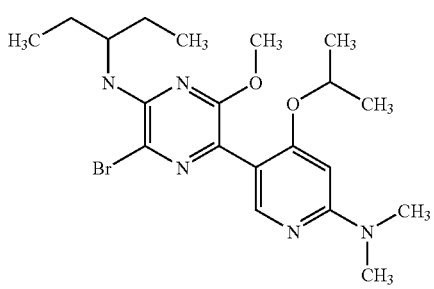 | [3-Bromo-5-(6-dimethylamino-4-isopropoxy-pyridin-3-yl)-6-methoxy-pyrazin-2-yl]-(1-ethyl-propyl)-amine |

TABLE III-continued

| Compound # | Structure | IUPAC Name |
|---|---|---|
| 218 | 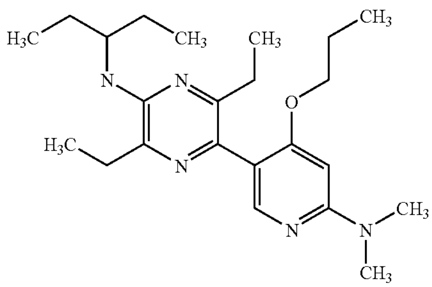 | [5-(6-Dimethylamino-4-propoxy-pyridin-3-yl)-3,6-diethyl-pyrazin-2-yl]-(1-ethyl-propyl)-amine |
| 219 | 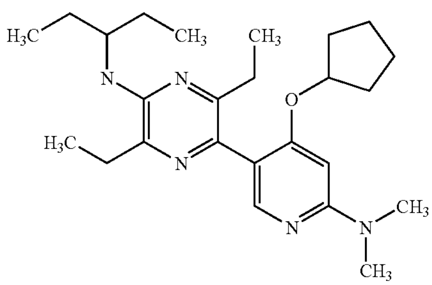 | [5-(4-Cyclopentyloxy-6-dimethylamino-pyridin-3-yl)-3,6-diethyl-pyrazin-2-yl]-(1-ethyl-propyl)-amine |
| 220 | 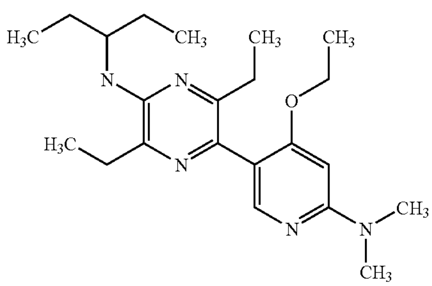 | [5-(6-Dimethylamino-4-ethoxy-pyridin-3-yl)-3,6-diethyl-pyrazin-2-yl]-(1-ethyl-propyl)-amine |
| 221 | 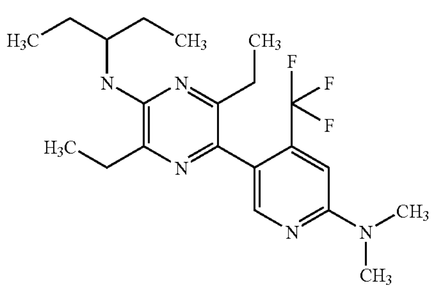 | [5-(6-Dimethylamino-4-trifluoromethyl-pyridin-3-yl)-3,6-diethyl-pyrazin-2-yl]-(1-ethyl-propyl)amine |
| 222 | 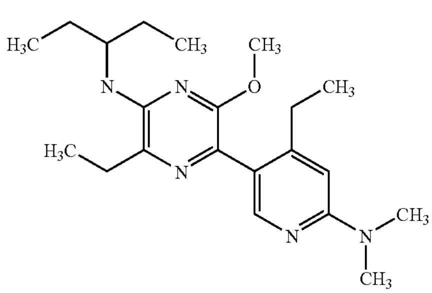 | [5-(6-Dimethylamino-4-ethyl-pyridin-3-yl)-3-ethyl-6-methoxy-pyrazin-2-yl]-(1-ethyl-propyl)-amine |

TABLE III-continued

| Compound # | Structure | IUPAC Name |
|---|---|---|
| 223 | 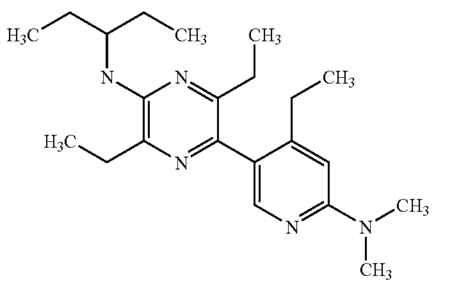 | [5-(6-Dimethylamino-4-ethyl-pyridin-3-yl)-3,6-diethyl-pyrazin-2-yl]-(1-ethyl-propyl)-amine |
| 224 | 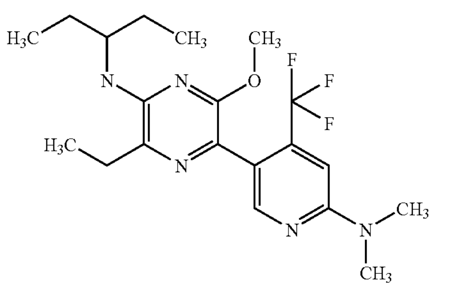 | [5-(6-Dimethylamino-4-trifluoromethyl-pyridin-3-yl)-3-ethyl-6-methoxy-pyrazin-2-yl]-(1-ethyl-propyl)-amine |
| 225 | 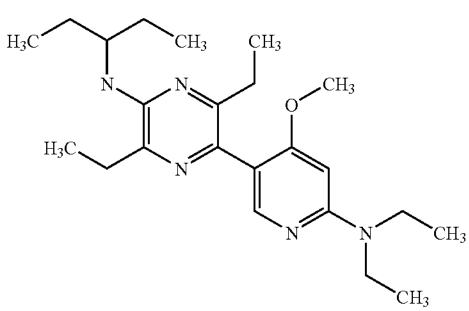 | [5-(6-Diethylamino-4-methoxy-pyridin-3-yl)-3,6-diethyl-pyrazin-2-yl]-(1-ethyl-propyl)-amine |
| 226 | 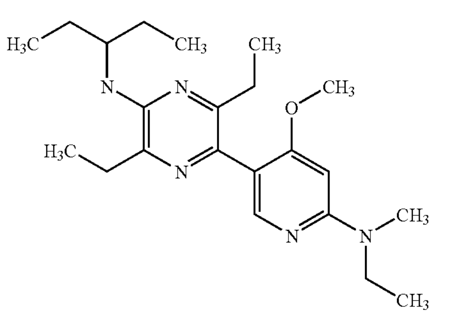 | {3,6-Diethyl-5-[6-(ethyl-methyl-amino)-4-methoxy-pyridin-3-yl]-pyrazin-2-yl}-(1-ethyl-propyl)-amine |
| 227 | 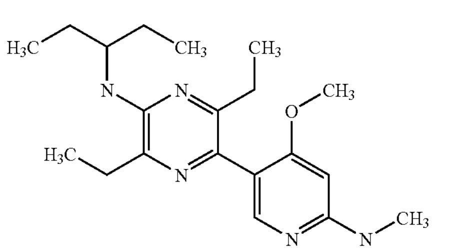 | [3,6-Diethyl-5-(4-methoxy-6-methylamino-pyridin-3-yl)-pyrazin-2-yl]-(1-ethyl-propyl)-amine |

TABLE III-continued

| Compound # | Structure | IUPAC Name |
|---|---|---|
| 228 | 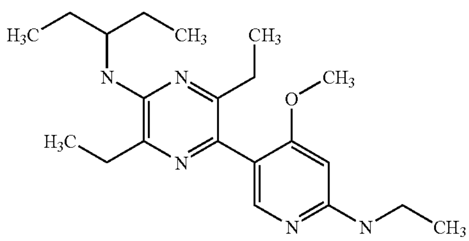 | [3,6-Diethyl-5-(6-ethylamino-4-methoxy-pyridin-3-yl)-pyrazin-2-yl]-(1-ethyl-propyl)-amine |
| 229 | 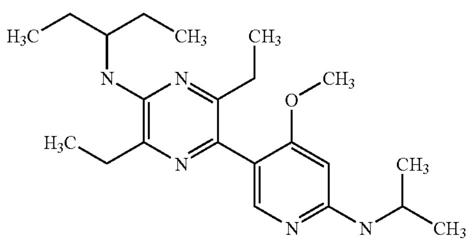 | [3,6-Diethyl-5-(6-isopropylamino-4-methoxy-pyridin-3-yl)-pyrazin-2-yl]-(1-ethyl-propyl)-amine |
| 230 | 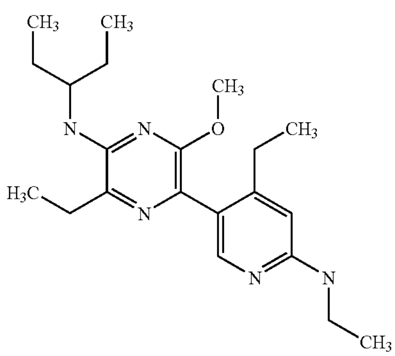 | [3-Ethyl-5-(4-ethyl-6-ethylamino-pyridin-3-yl)-6-methoxy-pyrazin-2-yl]-(1-ethyl-propyl)-amine |
| 231 | 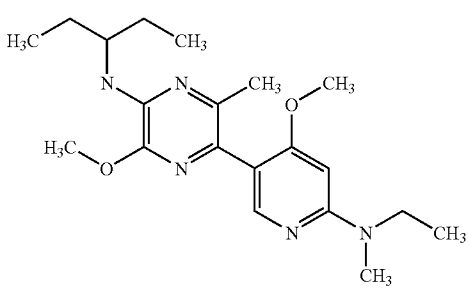 | {5-[6-(Ethyl-methyl-amino)-4-methoxy-pyridin-3-yl]-3-methoxy-6-methyl-pyrazin-2-yl}-(1-ethyl-propyl)-amine |
| 232 | 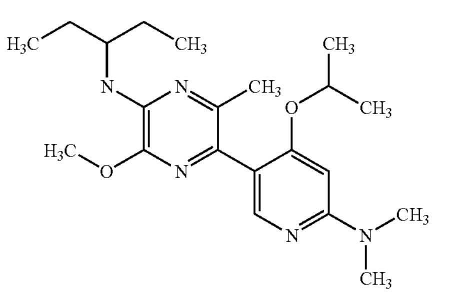 | [5-(6-Dimethylamino-4-isopropoxy-pyridin-3-yl)-3-methoxy-6-methyl-pyrazin-2-yl]-(1-ethyl-propyl)-amine |

TABLE III-continued

| Compound # | Structure | IUPAC Name |
|---|---|---|
| 233 | 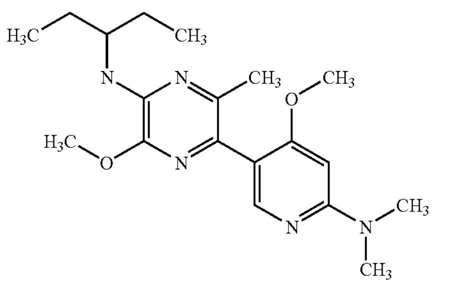 | [5-(6-Dimethylamino-4-methoxy-pyridin-3-yl)-3-methoxy-6-methyl-pyrazin-2-yl]-(1-ethyl-propyl)-amine |
| 234 | 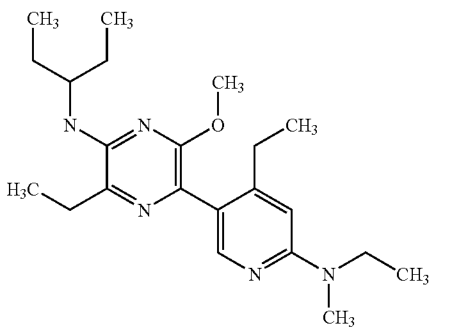 | {3-Ethyl-5-[4-ethyl-6-(ethyl-methyl-amino)-pyridin-3-yl]-6-methoxy-pyrazin-2-yl}-(1-ethyl-propyl)-amine |
| 235 | 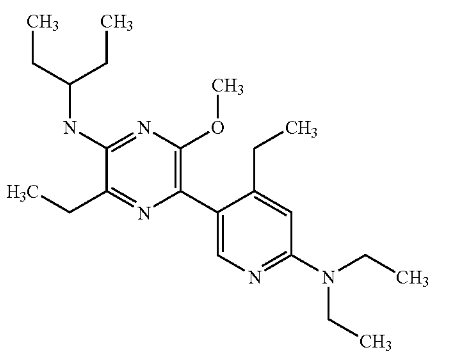 | [5-(6-Diethylamino-4-ethyl-pyridin-3-yl)-3-ethyl-6-methoxy-pyrazin-2-yl]-(1-ethyl-propyl)-amine |
| 236 | 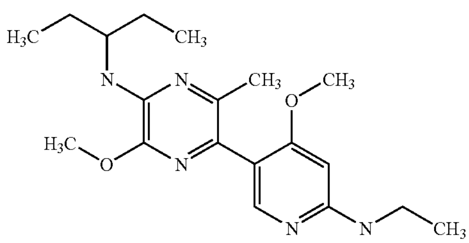 | [5-(6-Ethylamino-4-methoxy-pyridin-3-yl)-3-methoxy-6-methyl-pyrazin-2-yl]-(1-ethyl-propyl)-amine |
| 237 | 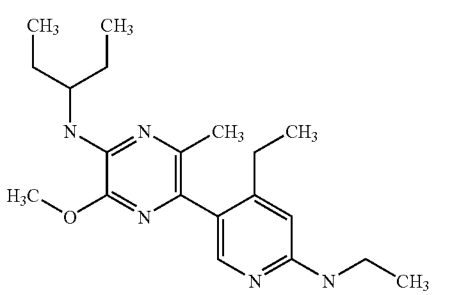 | [5-(4-Ethyl-6-ethylamino-pyridin-3-yl)-3-methoxy-6-methyl-pyrazin-2-yl]-(1-ethyl-propyl)-amine |

TABLE III-continued

| Compound # | Structure | IUPAC Name |
|---|---|---|
| 238 | 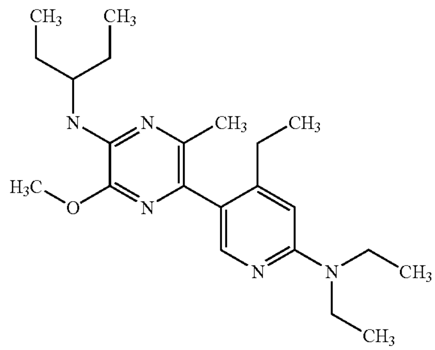 | [5-(6-Diethylamino-4-ethyl-pyridin-3-yl)-3-methoxy-6-methyl-pyrazin-2-yl]-(1-ethyl-propyl)-amine |
| 239 | 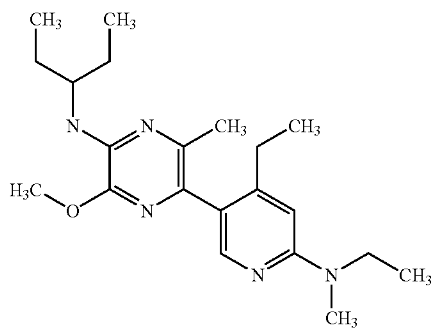 | {5-[4-Ethyl-6-(ethyl-methyl-amino)-pyridin-3-yl]-3-methoxy-6-methyl-pyrazin-2-yl}-(1-ethyl-propyl)-amine |
| 240 | 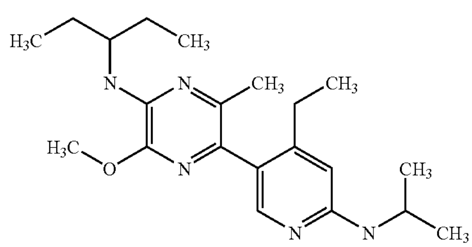 | [5-(4-Ethyl-6-isopropylamino-pyridin-3-yl)-3-methoxy-6-methyl-pyrazin-2-yl]-(1-ethyl-propyl)-amine |
| 241 | 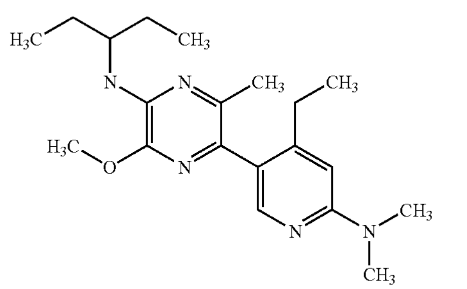 | [5-(6-Dimethylamino-4-ethyl-pyridin-3-yl)-3-methoxy-6-methyl-pyrazin-2-yl]-(1-ethyl-propyl)-amine |
| 242 | 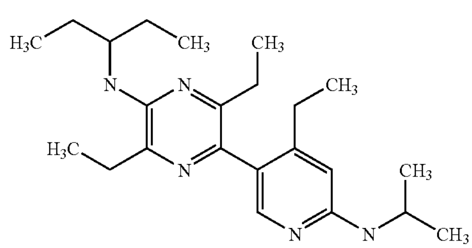 | [3,6-Diethyl-5-(4-ethyl-6-isopropylamino-pyridin-3-yl)-pyrazin-2-yl]-(1-ethyl-propyl)-amine |

TABLE III-continued

| Compound # | Structure | IUPAC Name |
|---|---|---|
| 243 | 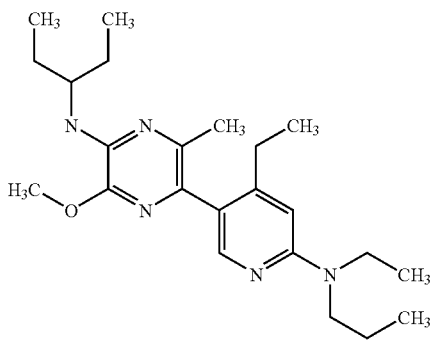 | {5-[4-Ethyl-6-(ethyl-propyl-amino)-pyridin-3-yl]-3-methoxy-6-methyl-pyrazin-2-yl}-(1-ethyl-propyl)-amine |
| 244 | 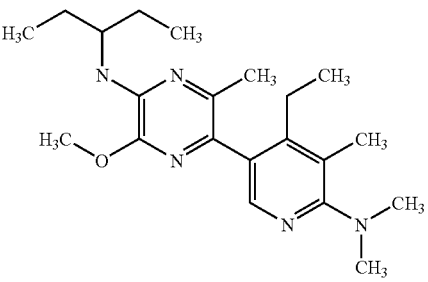 | [5-(6-Dimethylamino-4-ethyl-5-methyl-pyridin-3-yl)-3-methoxy-6-methyl-pyrazin-2-yl]-(1-ethyl-propyl)-amine |
| 245 | 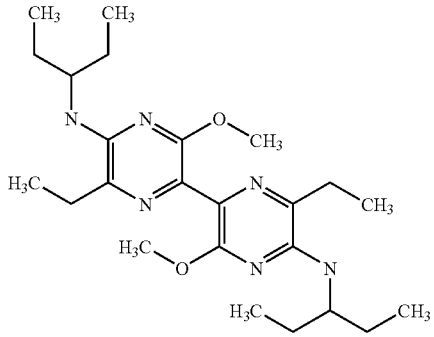 | 6,6'-Diethyl-N5,N5'-bis-(1-ethyl-propyl)-3,3'-dimethoxy-[2,2']bipyrazinyl-5,5'-diamine |
| 246 | 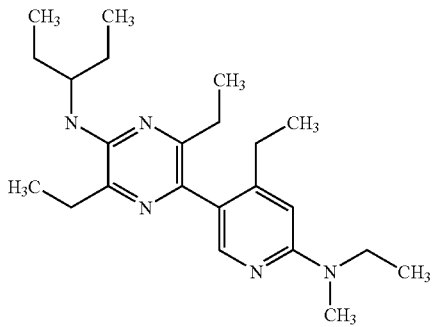 | {3,6-Diethyl-5-[4-ethyl-6-(ethyl-methyl-amino)-pyridin-3-yl]-pyrazin-2-yl}-(1-ethyl-propyl)-amine |
| 247 | 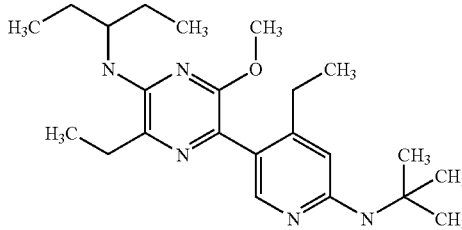 | [5-(6-tert-Butylamino-4-ethyl-pyridin-3-yl)-3-ethyl-6-methoxy-pyrazin-2-yl]-(1-ethyl-propyl)-amine |

TABLE III-continued

| Compound # | Structure | IUPAC Name |
|---|---|---|
| 248 | 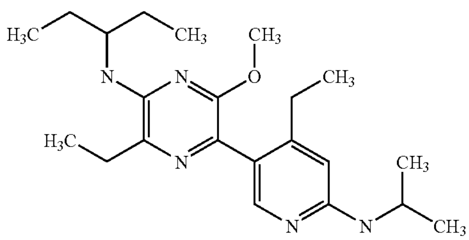 | [3-Ethyl-5-(4-ethyl-6-isopropylamino-pyridin-3-yl)-6-methoxy-pyrazin-2-yl]-(1-ethyl-propyl)-amine |
| 249 | 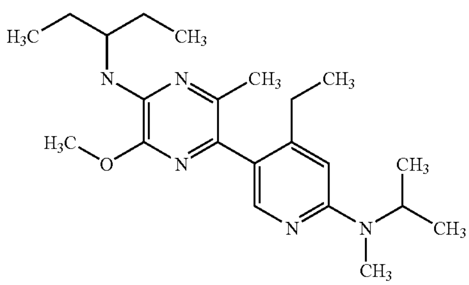 | {5-[4-Ethyl-6-(isopropyl-methyl-amino)-pyridin-3-yl]-3-methoxy-6-methyl-pyrazin-2-yl}-(1-ethyl-propyl)-amine |
| 250 | 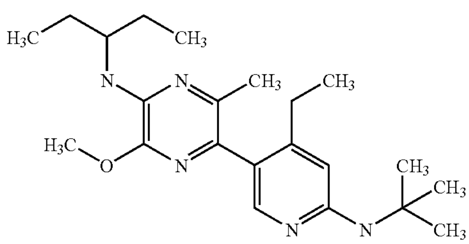 | [5-(6-tert-Butylamino-4-ethyl-pyridin-3-yl)-3-methoxy-6-methyl-pyrazin-2-yl]-(1-ethyl-propyl)-amine |
| 251 | 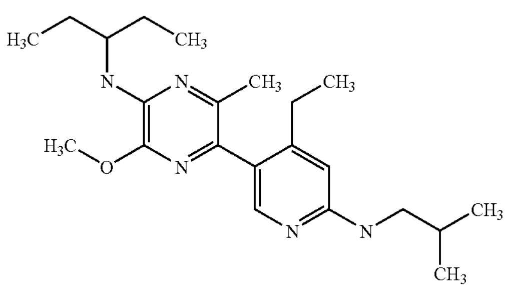 | [5-(4-Ethyl-6-isobutylamino-pyridin-3-yl)-3-methoxy-6-methyl-pyrazin-2-yl]-(1-ethyl-propyl)-amine |
| 252 | 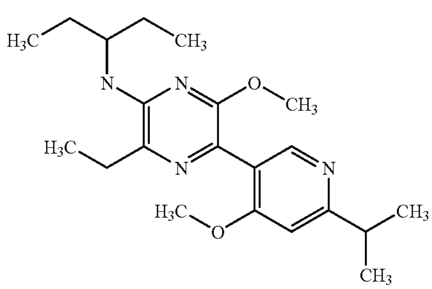 | [3-Ethyl-5-(6-isopropyl-4-methoxy-pyridin-3-yl)-6-methoxy-pyrazin-2-yl]-(1-ethyl-propyl)-amine |
| 253 | 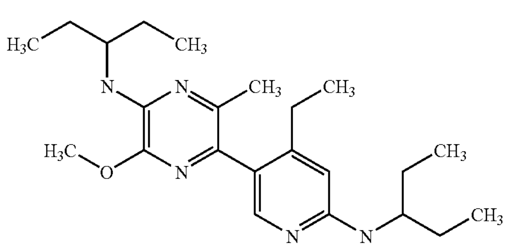 | {5-[4-Ethyl-6-(1-ethyl-propylamino)-pyridin-3-yl]-3-methoxy-6-methyl-pyrazin-2-yl}-(1-ethyl-propyl)-amine |

TABLE III-continued

| Compound # | Structure | IUPAC Name |
|---|---|---|
| 254 | 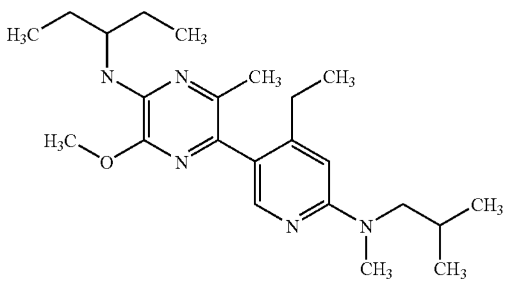 | {5-[4-Ethyl-6-(isobutyl-methyl-amino)-pyridin-3-yl]-3-methoxy-6-methyl-pyrazin-2-yl}-(1-ethyl-propyl)-amine |
| 255 | 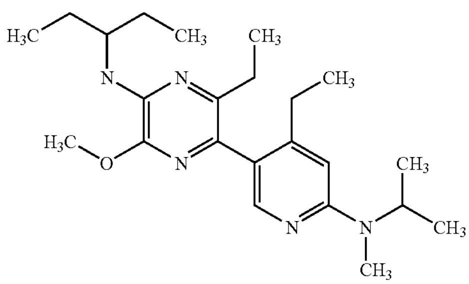 | {6-Ethyl-5-[4-ethyl-6-(isopropyl-methyl-amino)-pyridin-3-yl]-3-methoxy-pyrazin-2-yl}-(1-ethyl-propyl)-amine |
| 256 | 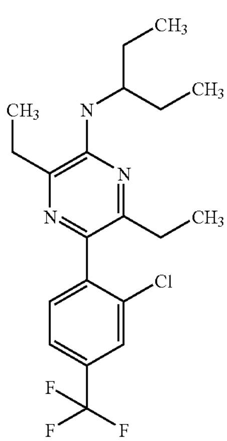 | [5-(2-Chloro-4-trifluoromethyl-phenyl)-3,6-diethyl-pyrazin-2-yl]-(1-ethyl-propyl)-amine |
| 257 | 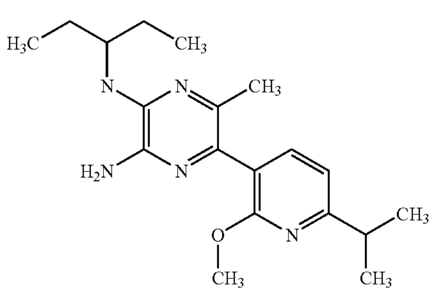 | N2-(1-Ethyl-propyl)-5-(6-isopropyl-2-methoxy-pyridin-3-yl)-6-methyl-pyrazine-2,3-diamine |

TABLE III-continued

| Compound # | Structure | IUPAC Name |
|---|---|---|
| 258 | 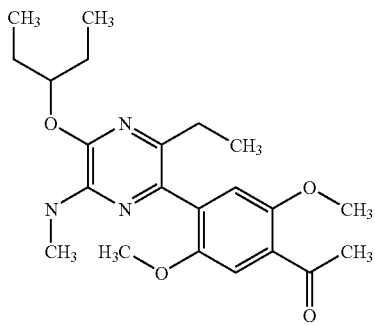 | 1-{4-[3-Ethyl-5-(1-ethyl-propoxy)-6-methylamino-pyrazin-2-yl]-2,5-dimethoxy-phenyl}-ethanone |
| 259 | 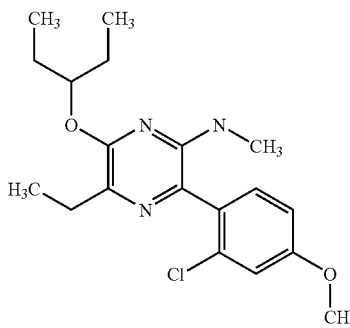 | [3-(2-Chloro-4-methoxy-phenyl)-5-ethyl-6-(1-ethyl-propoxy)-pyrazin-2-yl]-methyl-amine |
| 260 | 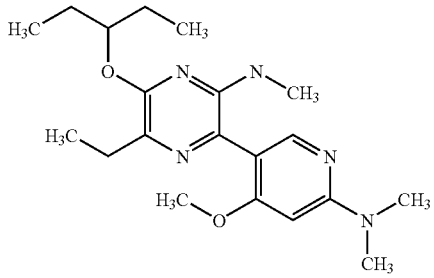 | [3-(6-Dimethylamino-4-methoxy-pyridin-3-yl)-5-ethyl-6-(1-ethyl-propoxy)-pyrazin-2-yl]-methyl-amine |
| 261 | 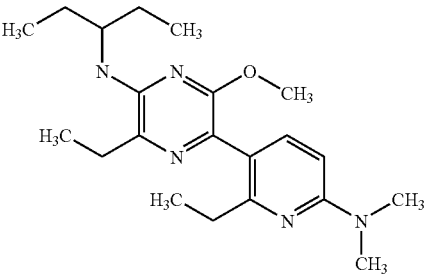 | [5-(6-Dimethylamino-2-ethyl-pyridin-3-yl)-3-ethyl-6-methoxy-pyrazin-2-yl]-(1-ethyl-propyl)-amine |
| 262 | 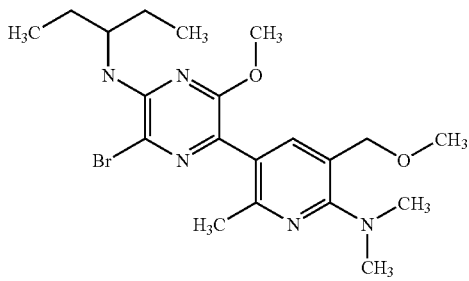 | [3-Bromo-5-(6-dimethylamino-5-methoxymethyl-2-methyl-pyridin-3-yl)-6-methoxy-pyrazin-2-yl]-(1-ethyl-propyl)-amine |

TABLE III-continued

| Compound # | Structure | IUPAC Name |
|---|---|---|
| 263 | 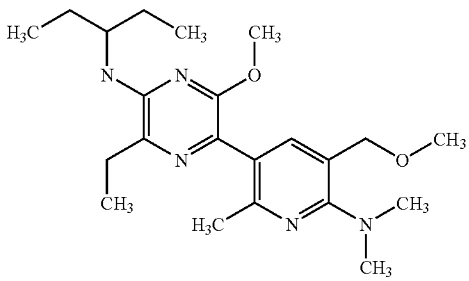 | [5-(6-Dimethylamino-5-methoxymethyl-2-methyl-pyridin-3-yl)-3-ethyl-6-methoxy-pyrazin-2-yl]-(1-ethyl-propyl)-amine |
| 264 | 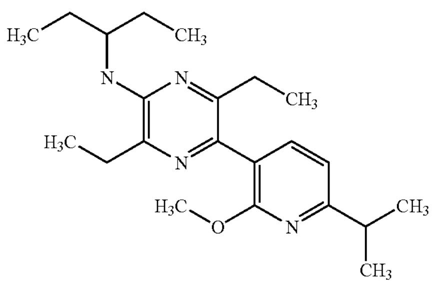 | [3,6-Diethyl-5-(6-isopropyl-2-methoxy-pyridin-3-yl)-pyrazin-2-yl]-(1-ethyl-propyl)-amine |
| 265 | 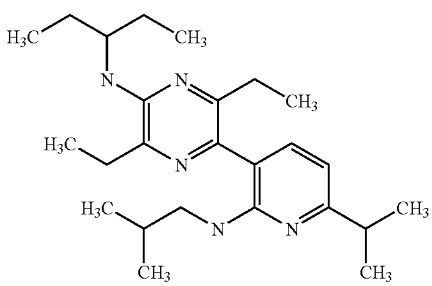 | 1-{3-[3,6-Diethyl-5-(1-ethyl-propylamino)-pyrazin-2-yl]-6-isopropyl-pyridin-2-ylamino}-propan-2-ol |
| 266 | 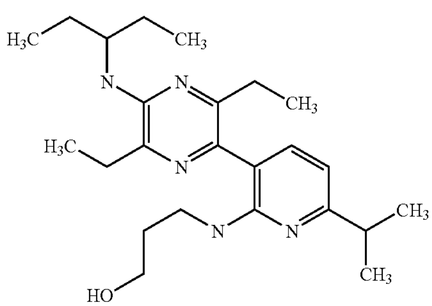 | 3-{3-[3,6-Diethyl-5-(1-ethyl-propylamino)-pyrazin-2-yl]-6-isopropyl-pyridin-2-ylamino}propan-1-ol |
| 267 | 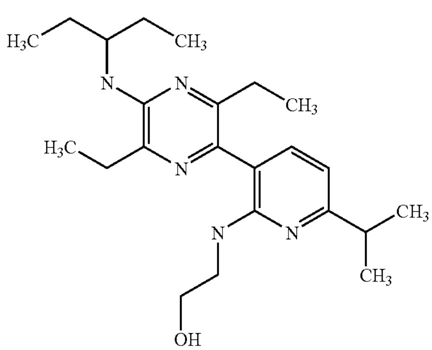 | 2-{3-[3,6-Diethyl-5-(1-ethyl-propylamino)-pyrazin-2-yl]-6-isopropyl-pyridin-2-ylamino}-ethanol |

TABLE III-continued

| Compound # | Structure | IUPAC Name |
|---|---|---|
| 268 | 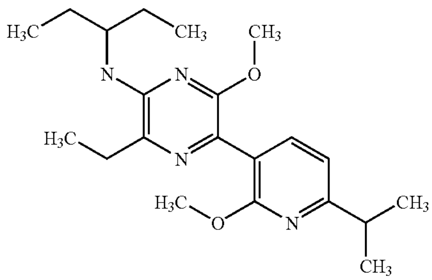 | [3-Ethyl-5-(6-isopropyl-2-methoxy-pyridin-3-yl)-6-methoxy-pyrazin-2-yl]-(1-ethyl-propyl)-amine |
| 269 | 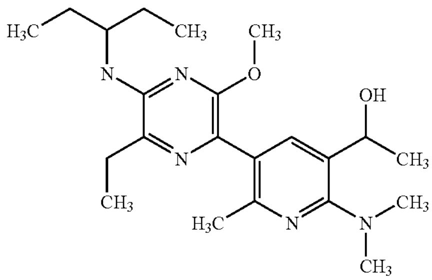 | 1-{2-Dimethylamino-5-[6-ethyl-5-(1-ethyl-propylamino)-3-methoxy-pyrazin-2-yl]-6-methyl-pyridin-3-yl}-ethanol |
| 270 | 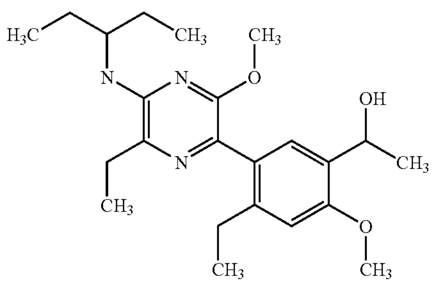 | 1-{4-Ethyl-5-[6-ethyl-5-(1-ethyl-propylamino)-3-methoxy-pyrazin-2-yl]-2-methoxy-phenyl}-ethanol |
| 271 | 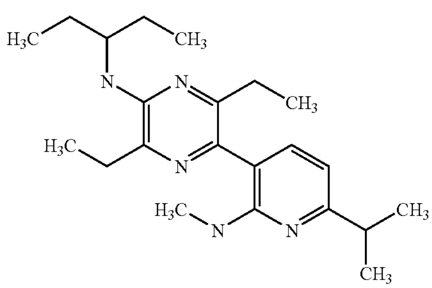 | [3,6-Diethyl-5-(6-isopropyl-2-methylamino-pyridin-3-yl)-pyrazin-2-yl]-(1-ethyl-propyl)-amine |
| 272 | 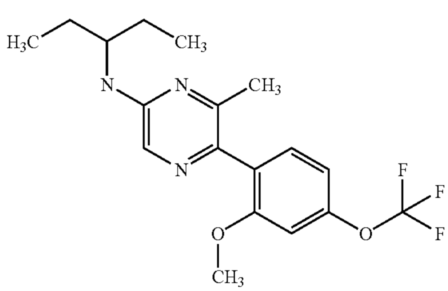 | (1-Ethyl-propyl)-[5-(2-methoxy-4-trifluoromethoxy-phenyl)-6-methyl-pyrazin-2-yl]-amine |

TABLE III-continued

| Compound # | Structure | IUPAC Name |
|---|---|---|
| 273 | 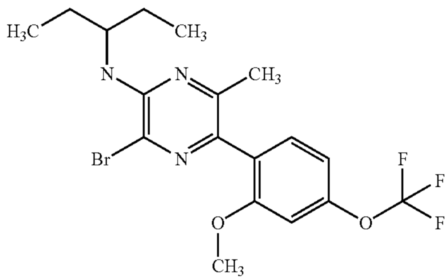 | [3-Bromo-5-(2-methoxy-4-trifluoromethoxy-phenyl)-6-methyl-pyrazin-2-yl]-(1-ethyl-propyl)-amine |
| 274 | 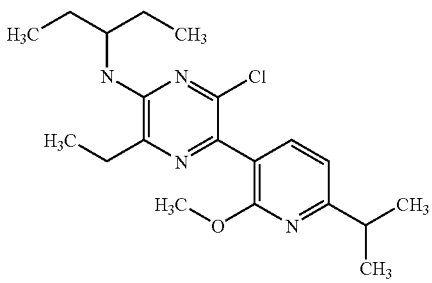 | [6-Chloro-3-ethyl-5-(6-isopropyl-2-methoxy-pyridin-3-yl)-pyrazin-2-yl]-(1-ethyl-propyl)-amine |
| 275 | 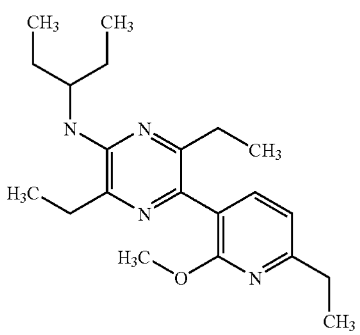 | [3,6-Diethyl-5-(6-ethyl-2-methoxy-pyridin-3-yl)-pyrazin-2-yl]-(1-ethyl-propyl)-amine |
| 276 | 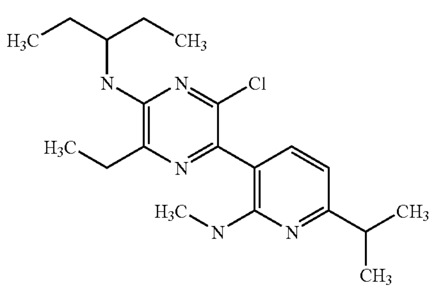 | [6-Chloro-3-ethyl-5-(6-isopropyl-2-methylamino-pyridin-3-yl)-pyrazin-2-yl]-(1-ethyl-propyl)-amine |
| 277 | 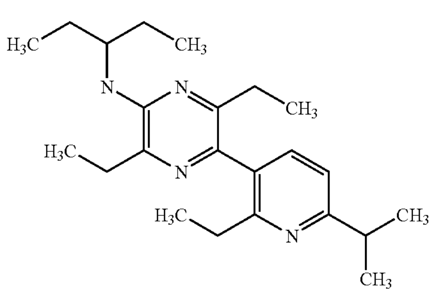 | [3,6-Diethyl-5-(2-ethyl-6-isopropyl-pyridin-3-yl)-pyrazin-2-yl]-(1-ethyl-propyl)-amine |

| Compound # | Structure | IUPAC Name |
|---|---|---|
| 278 | 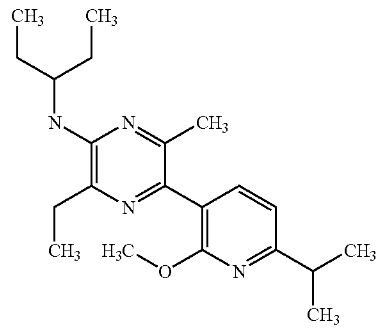 | [3-Ethyl-5-(6-isopropyl-2-methoxy-pyridin-3-yl)-6-methyl-pyrazin-2-yl]-(1-ethyl-propyl)-amine |
| 279 | 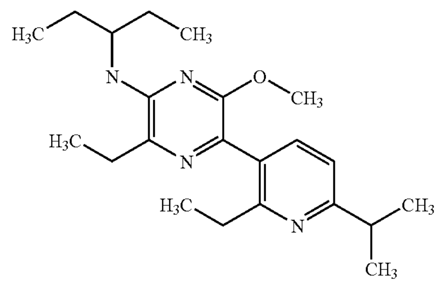 | [3-Ethyl-5-(2-ethyl-6-isopropyl-pyridin-3-yl)-6-methoxy-pyrazin-2-yl]-(1-ethyl-propyl)-amine |
| 280 | 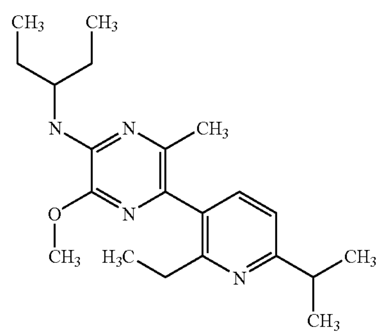 | [5-(2-Ethyl-6-isopropyl-pyridin-3-yl)-3-methoxy-6-methyl-pyrazin-2-yl]-(1-ethyl-propyl)-amine |
| 281 | 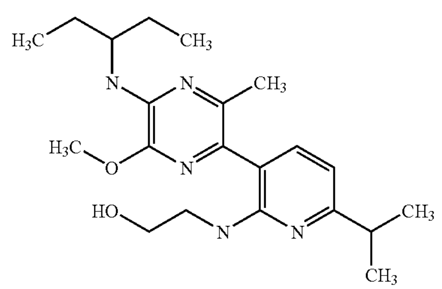 | 2-{3-[5-(1-Ethyl-propylamino)-6-methoxy-3-methyl-pyrazin-2-yl]-6-isopropyl-pyridin-2-ylamino}-ethanol |
| 282 | 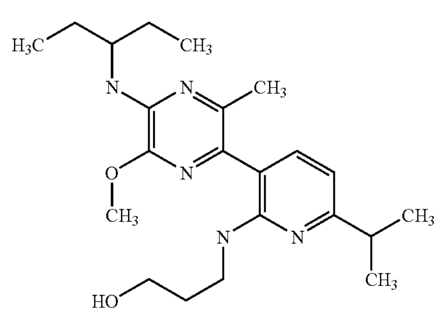 | 3-{3-[5-(1-Ethyl-propylamino)-6-methoxy-3-methyl-pyrazin-2-yl]-6-isopropyl-pyridin-2-ylamino}-propan-1-ol |

TABLE III-continued

| Compound # | Structure | IUPAC Name |
|---|---|---|
| 283 | 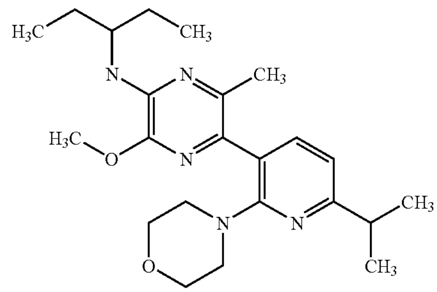 | (1-Ethyl-propyl)-[5-(6-isopropyl-2-morpholin-4-yl-pyridin-3-yl)-3-methoxy-6-methyl-pyrazin-2-yl]-amine |
| 284 | 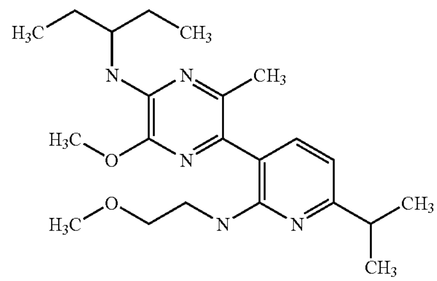 | (1-Ethyl-propyl)-{5-[6-isopropyl-2-(2-methoxy-ethylamino)-pyridin-3-yl]-3-methoxy-6-methyl-pyrazin-2-yl}-amine |
| 285 | 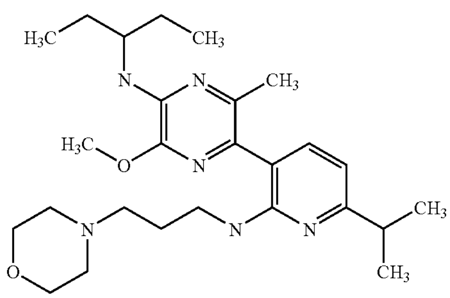 | (1-Ethyl-propyl)-{5-[6-isopropyl-2-(3-morpholin-4-yl-propylamino)-pyridin-3-yl]-3-methoxy-6-methyl-pyrazin-2-yl}-amine |
| 286 | 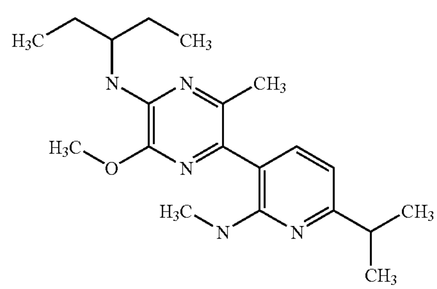 | (1-Ethyl-propyl)-[5-(6-isopropyl-2-methylamino-pyridin-3-yl)-3-methoxy-6-methyl-pyrazin-2-yl]-amine |
| 287 | 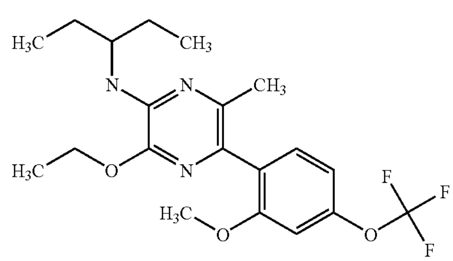 | [3-Ethoxy-5-(2-methoxy-4-trifluoromethoxy-phenyl)-6-methyl-pyrazin-2-yl]-(1-ethyl-propyl)-amine |

TABLE III-continued

| Compound # | Structure | IUPAC Name |
|---|---|---|
| 288 | 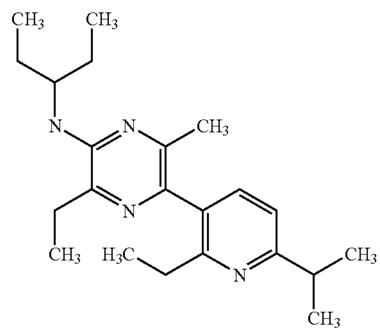 | [3-Ethyl-5-(2-ethyl-6-isopropyl-pyridin-3-yl)-6-methyl-pyrazin-2-yl]-(1-ethyl-propyl)-amine |
| 289 | 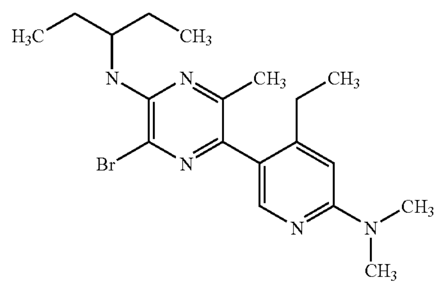 | [3-Bromo-5-(6-dimethylamino-4-ethyl-pyridin-3-yl)-6-methyl-pyrazin-2-yl]-(1-ethyl-propyl)-amine |
| 290 | 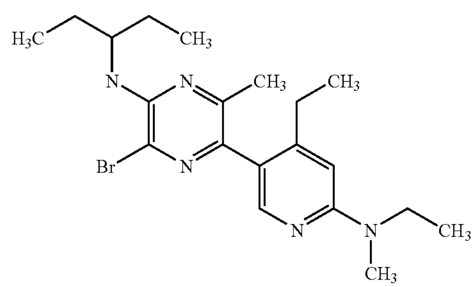 | {3-Bromo-5-[4-ethyl-6-(ethyl-methyl-amino)-pyridin-3-yl]-6-methyl-pyrazin-2-yl}-(1-ethyl-propyl)-amine |
| 291 | 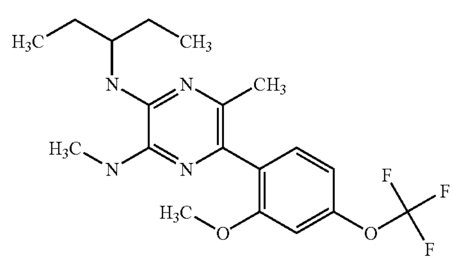 | N2-(1-Ethyl-propyl)-5-(2-methyoxy-4-trifluoromethoxy-phenyl)-6,N3-dimethyl-pyrazine-2,3-diamine |
| 292 | 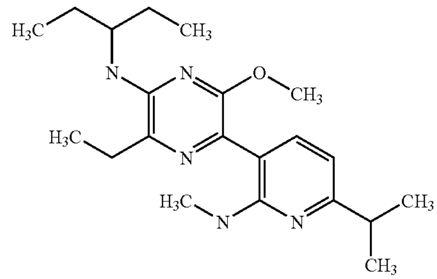 | [3-Ethyl-5-(6-isopropyl-2-methylamino-pyridin-3-yl)-6-methoxy-pyrazin-2-yl]-(1-ethyl-propyl)-amine |

TABLE III-continued

| Compound # | Structure | IUPAC Name |
|---|---|---|
| 293 | 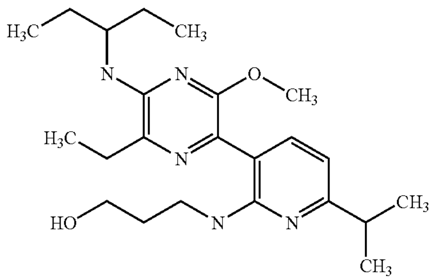 | 3-{3-[6-Ethyl-5-(1-ethyl-propylamino)-3-methoxy-pyrazin-2-yl]-6-isopropyl-pyridin-2-ylamino}-propan-1-ol |
| 294 | 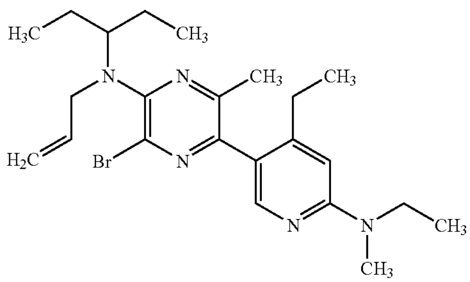 | Allyl-{3-bromo-5-[4-ethyl-6-(ethyl-methyl-amino)-pyridin-3-yl]-6-methyl-pyrazin-2-yl}-(1-ethyl-propyl)-amine |
| 295 | 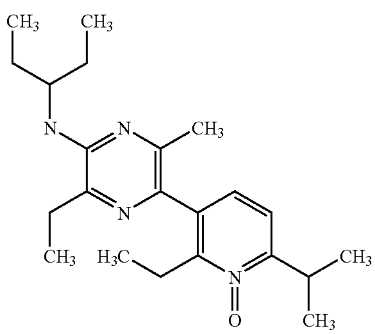 | 6-Ethyl-5-[6-ethyl-5-(1-ethyl-propylamino)-3-methyl-pyrazin-2-yl]-2-isopropyl-2H-pyridin-1-ol |
| 296 | 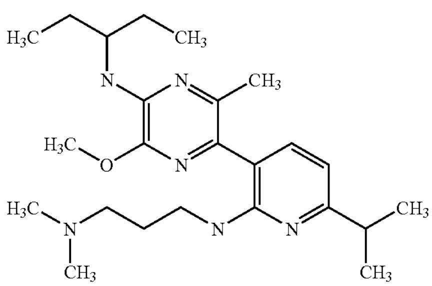 | N-{3-[5-(1-Ethyl-propylamino)-6-methoxy-3-methyl-pyrazin-2-yl]-6-isopropyl-pyridin-2-yl}-N',N'-dimethyl-propane-1,3-diamine |
| 297 | 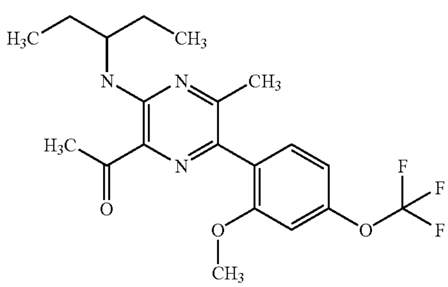 | 1-[3-(1-Ethyl-propylamino)-6-(2-methoxy-4-trifluoromethoxy-phenyl)-5-methyl-pyrazin-2-yl]-ethanone |

TABLE III-continued

| Compound # | Structure | IUPAC Name |
|---|---|---|
| 298 | 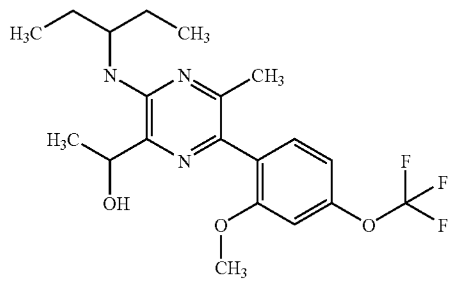 | 1-[3-(1-Ethyl-propylamino)-6-(2-methoxy-4-trifluoromethoxy-phenyl)-5-methyl-pyrazin-2-yl]-ethanol |
| 299 | 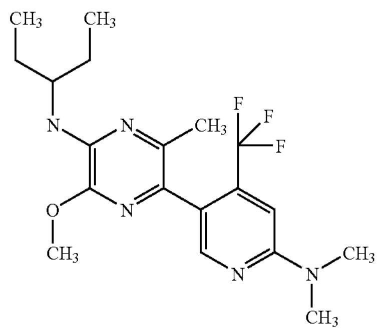 | [5-(6-Dimethylamino-4-trifluoromethyl-pyridin-3-yl)-3-methoxy-6-methyl-pyrazin-2-yl]-(1-ethyl-propyl)-amine |
| 300 | 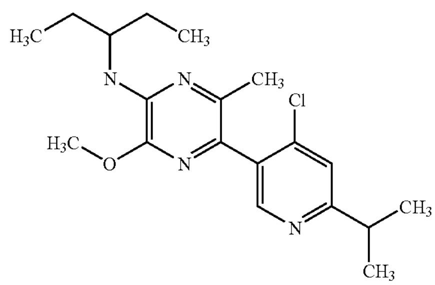 | [5-(4-Chloro-6-isopropyl-pyridin-3-yl)-3-methoxy-6-methyl-pyrazin-2-yl]-(1-ethyl-propyl)-amine |
| 301 | 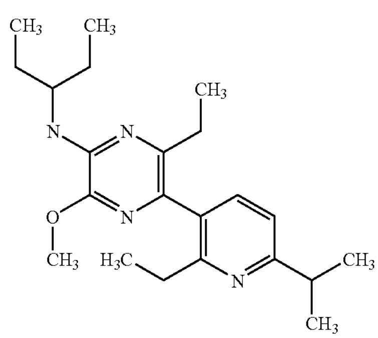 | [6-Ethyl-5-(2-ethyl-6-isopropyl-pyridin-3-yl)-3-methoxy-pyrazin-2-yl]-(1-ethyl-propyl)-amine |
| 302 | 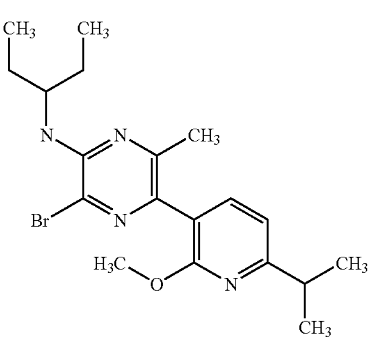 | [3-Bromo-5-(6-isopropyl-2-methoxy-pyridin-3-yl)-6-methyl-pyrazin-2-yl]-(1-ethyl-propyl)-amine |

TABLE III-continued

| Compound # | Structure | IUPAC Name |
|---|---|---|
| 303 | 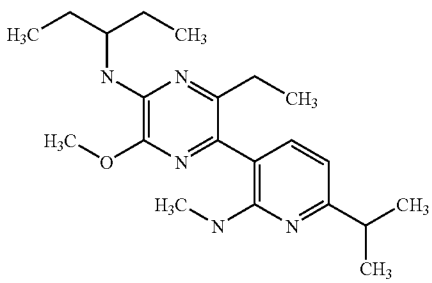 | [6-Ethyl-5-(6-isopropyl-2-methylamino-pyridin-3-yl)-3-methoxy-pyrazin-2-yl]-(1-ethyl-propyl)-amine |
| 304 | 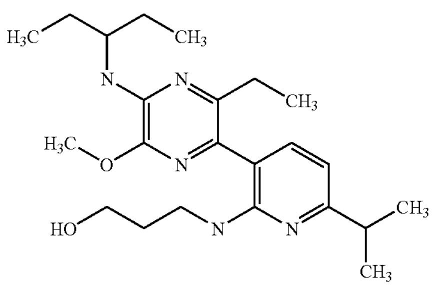 | 3-{3-[3-Ethyl-5-(1-ethyl-propylamino)-6-methoxy-pyrazin-2-yl]-6-isopropyl-pyridin-2-ylamino}-propan-1-ol |
| 305 | 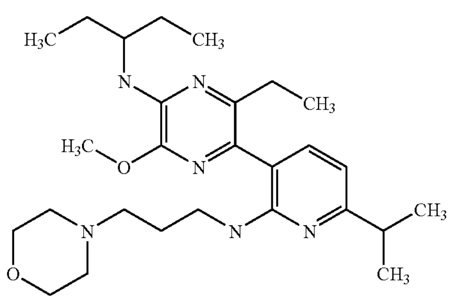 | {6-Ethyl-5-[6-isopropyl-2-(3-morpholin-4-yl-propylamino)-pyridin-3-yl]-3-methoxy-pyrazin-2-yl}-(1-ethyl-propyl)-amine |
| 306 | 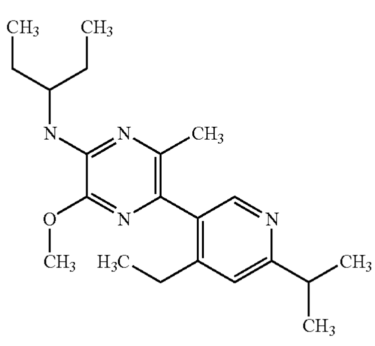 | [5-(4-Ethyl-6-isopropyl-pyridin-3-yl)-3-methoxy-6-methyl-pyrazin-2-yl]-(1-ethyl-propyl)-amine |
| 307 | 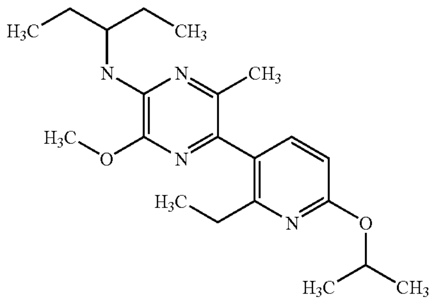 | [5-(2-Ethyl-6-isopropoxy-pyridin-3-yl)-3-methoxy-6-methyl-pyrazin-2-yl]-(1-ethyl-propyl)-amine |

TABLE III-continued

| Compound # | Structure | IUPAC Name |
|---|---|---|
| 308 | 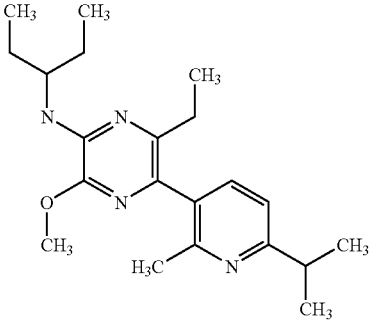 | [6-Ethyl-5-(6-isopropyl-2-methyl-pyridin-3-yl)-3-methoxy-pyrazin-2-yl]-(1-ethyl-propyl)-amine |
| 309 | 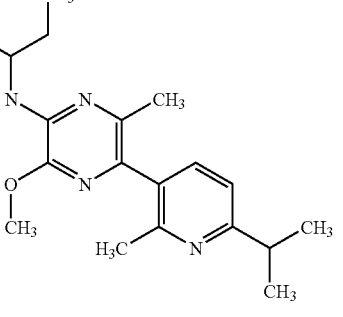 | (1-Ethyl-propyl)-[5-(6-isopropyl-2-methyl-pyridin-3-yl)-3-methoxy-6-methyl-pyrazin-2-yl]-amine |
| 310 | 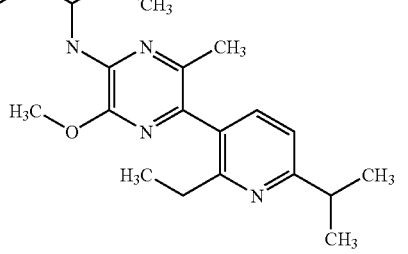 | (1-Ethyl-butyl)-[5-(2-ethyl-6-isopropyl-pyridin-3-yl)-3-methoxy-6-methyl-pyrazin-2-yl]-amine |
| 311 | 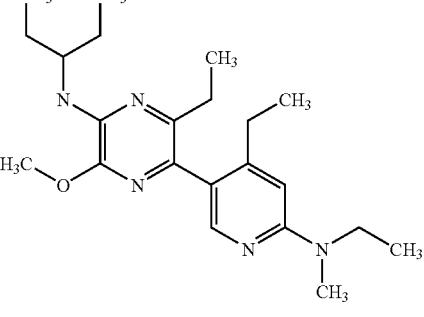 | {6-Ethyl-5-[4-ethyl-6-(ethyl-methyl-amino)-pyridin-3-yl]-3-methoxy-pyrazin-2-yl}-(1-ethyl-propyl)-amine |
| 312 | 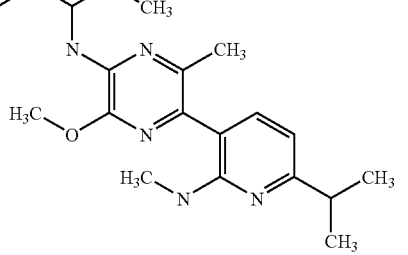 | (1-Ethyl-butyl)-[5-(6-isopropyl-2-methylamino-pyridin-3-yl)-3-methoxy-6-methyl-pyrazin-2-yl]-amine |

TABLE III-continued

| Compound # | Structure | IUPAC Name |
|---|---|---|
| 313 | 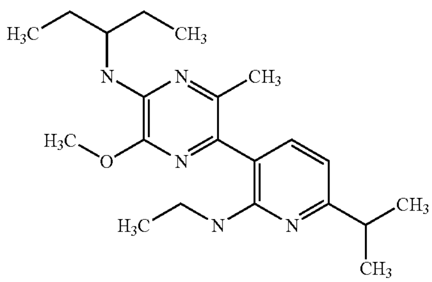 | [5-(2-Ethylamino-6-isopropyl-pyridin-3-yl)-3-methoxy-6-methyl-pyrazin-2-yl]-(1-ethyl-propyl)-amine |
| 314 | 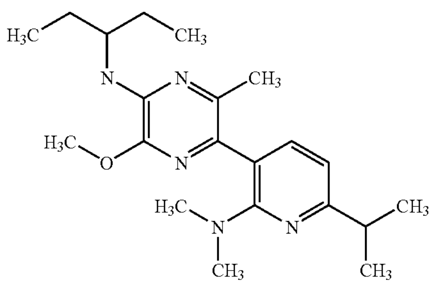 | [5-(2-Dimethylamino-6-isopropyl-pyridin-3-yl)-3-methoxy-6-methyl-pyrazin-2-yl]-(1-ethyl-propyl)-amine |
| 315 | 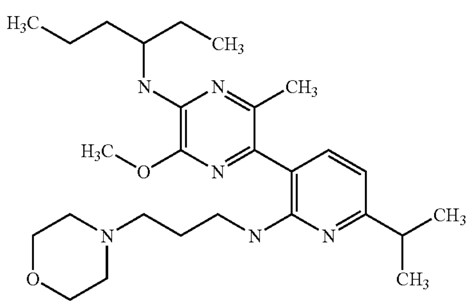 | (1-Ethyl-butyl)-{5-[6-isopropyl-2-(3-morpholin-4-yl-propylamino)-pyridin-3-yl-3-]methoxy-6-methyl-pyrazin-2-yl}-amine |
| 316 | 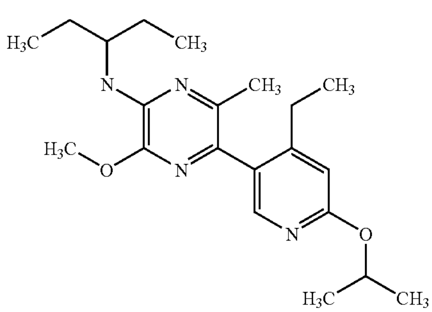 | [5-(4-Ethyl-6-isopropoxy-pyridin-3-yl)-3-methoxy-6-methyl-pyrazin-2-yl]-(1-ethyl-propyl)-amine |
| 317 | 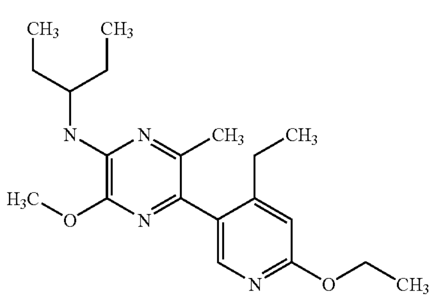 | [5-(6-Ethoxy-4-ethyl-pyridin-3-yl)-3-methoxy-6-methyl-pyrazin-2-yl]-(1-ethyl-propyl)-amine |

Example 30

Assay for CRF Receptor Binding Activity

As discussed above, the following assay is defined herein as a standard in vitro CRF binding assay. The pharmaceutical utility of compounds of this invention is indicated by the following assay for CRF1 receptor activity.

The CRF receptor binding is performed using a modified version of the assay described by Grigoriadis and De Souza (*Methods in Neurosciences*, Vol. 5, 1991). IMR-32 human neuroblastoma cells, a cell line that can be induced to express the CRF1 receptor, are cultured in growth medium consisting of EMEM w/Earle's BSS (JRH Biosciences, Cat# 51411) supplemented with 10% Fetal Bovine Serum, 25 mM HEPES (pH 7.2), 1 mM Sodium Pyruvate, and Non-Essential Amino Acids (JRH Biosciences, Cat# 58572). Stock cultures of cells are grown to confluence and subcultured twice per week at split ratios of 1:2 to 1:4 (cells are dislodged during subculturing using No-Zyme, JRH Biosciences, Cat# 59226). To induce CRF1 receptor expression, the cells are grown to approximately 80% confluence and then changed to growth media containing 2.5 µM 5-bromo-2'deoxyuridine (BrdU, Sigma, Cat# B9285). Growth media containing BrdU is replaced every 3–4 days and the cells are harvested via centrifugation (using No-Zyme) after 10 days of BrdU treatment. Harvested cells are stored frozen at −80° C. until needed for the preparation of membrane homogenates.

To prepare receptor-containing membranes cells are homogenized in wash buffer (50 mM Tris HCl, 10 mM $MgCl_2$, 2 mM EGTA, pH 7.4) and centrifuged at 48,000×g for 10 minutes at 4° C. The pellet is re-suspended in wash buffer and the homogenization and centrifugation steps are performed once more.

Membrane pellets (containing CRF receptors) are resuspended and brought to a final concentration of 1.0 mg membrane protein/ml in binding buffer (Tris buffer above with 0.1% BSA and 0.1 mM bacitracin). For the binding assay, 150 microliters of the membrane preparation is added to 96 well microtube plates containing 50 microliters of $^{125}I$-CRF (SA 2200 Ci/mmol, final concentration of 100 pM) and 2 microliters of test compound. Binding is carried out at room temperature for 2 hours. Plates are then harvested using 50 mM Tris buffer pH 7.4, on a BRANDEL 96 well cell harvester and filters (soaked in 1% PEI for 1.5 hours) are counted for gamma emissions on a Wallac 1205 BETA-PLATE liquid scintillation counter. Non-specific binding is defined by 2 micromolar cold CRF. $K_i$ values are calculated with the non-linear curve fitting program RS/1 (BBN Software Products Corp., Cambridge, Mass.).

The binding affinity for the compounds of Formula I expressed as a $K_i$ value, generally ranges from about 0.5 nanomolar to about 10 micromolar. Preferred compounds of Formula I exhibit $K_i$ values of less than or equal to 1.5 micromolar, more preferred compounds of Formula I exhibit $K_i$ values of less than 500 nanomolar, still more preferred compounds of Formula I exhibit $K_i$ values of less than 100 nanomolar, and most preferred compound of Formula I exhibit $K_i$ values of less than 10 nanomolar.

Compounds in Table I which have an asterisk in the column labeled "$K_i$<1 µM" have been tested in this assay and found to exhibit a $K_i$ value of less than 1 micromolar. All compounds shown in Table II have also been tested in this assay and found to exhibit a $K_i$ value of less than 1 micromolar.

Example 31

Preparation of Radiolabeled Probe Compounds of Formula I

The compounds of Formula I are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of Formula I as substrate. In addition, certain precursors may be subjected to tritium-halogen exchange with tritium gas, tritium gas reduction of unsaturated bonds, or reduction using sodium borotritide, as appropriate.

Example 32

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of Formula I prepared as described in the preceding Examples.

Example 33

Additional Aspects of Preferred Compounds of Formula I

The most preferred compounds of Formula I are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of Formula I at certain doses (e.g., doses yielding therapeutically effective in vivo concentrations or preferably doses of 10, 50, 100, 150, or 200 mg/kg—preferably 150 mg/kg—administered parenterally or preferably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably not more than 25%, and more preferably not more than 10% over matched untreated controls in dogs or other non-rodent animals.

In yet another aspect such doses of such preferred compounds also preferably do not promote the release of liver enzymes (e.g., ALT, LDH, or AST) from hepatocytes in vivo. Preferably such doses do not elevate such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro.

Because side effects are often due to undesirable receptor activation or antagonism, preferred compounds of Formula I exert their receptor-modulatory effects and bind to the CRF1 receptor with high selectivity. This means that they do not bind to certain other receptors (i.e., other than CRF receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity also includes $GABA_A$ receptors, bioactive peptide receptors (including NPY and VIP receptors), neurokinin receptors, bradykinin receptors (e.g., BK1 receptors and BK2 receptors), and hormone receptors (including thyrotropin releasing hormone receptors and melanocyte-concentrating hormone receptors).

Example 34

Absence of Sodium Ion Channel Activity

Preferred compounds of Formula I do not exhibit activity as sodium ion channel blockers. Sodium channel activity may be measured a standard in vitro sodium channel binding assays such as the assay given by Brown et al. (J. Neurosci. (1986) 265: 17995–18004). Preferred compounds of Formula I exhibit less than 15 percent inhibition, and more preferably less than 10 percent inhibition, of sodium channel specific ligand binding when present at a concentration of 4 µM. The sodium ion channel specific ligand used may be labeled batrachotoxinin, tetrodotoxin, or saxitoxin. Such assays, including the assay of Brown referred to above, are performed as a commercial service by CEREP, INC., Redmond, Wash.

Alternatively, sodium ion channel activity may be measured in vivo in an assay of anti-epileptic activity. Anti-epileptic activity of compounds may be measured by the ability of the compounds to inhibit hind limb extension in the supramaximal electroshock model. Male Han Wistar rats (150–200 mg) are dosed i.p. with a suspension of 1 to 20 mg of test compound in 0.25% methylcellulose 2 hr. prior to test. A visual observation is carried out just prior to testing for the presence of ataxia. Using auricular electrodes a current of 200 mA, duration 200 milliseconds, is applied and the presence or absence of hind limb extension is noted. Preferred compounds of Formula I do not exhibit significant anti-epileptic activity at the $p<0.1$ level of significance or more preferably at the $p<0.05$ level of significance as measured using a standard parametric assay of statistical significance such as a student's T test.

Example 35

Optimal In Vitro Half-Life

Compound half-life values ($t_{1/2}$ values) may be determined via the following standard liver microsomal half-life assay. Liver microsomes are obtained from pooled liver samples and prepared so that the P-450 enzyme content is approximately 0.5 mmol/mg protein. Reactions are preformed in a 5 ml well deep-well plate as follows:

Phosphate buffer: 19 mL 0.1 M $NaH_2PO_4$, 81 mL 0.1 $Na_2HPO_4$, pH 7.4 with $H_3PO_4$.

CoFactor Mixture: 16.2 mg NADP, 45.4 mg Glucose-6-phosphate in 4 mL 100 mM $MgCl_2$.

Glucose-6-phosphate dehydrogenase: 214.3 microliters glucose-6-phosphate dehydrogenase, 1285.7 microliters distilled water Starting Reaction Mixture: 3 mL CoFactor Mixture, 1.2 mL Glucose-6-phosphate dehydrogenase 6 identical sample wells each containing 25 microliters microsomes, 5 microliters test compound (from a 100 uM stock), and 399 microliters 0.1 M phosphate buffer, pH 7.4, are prepared. A seventh well containing 25 microliters microsomes, 399 microliters 0.1 M phosphate buffer, pH 7.4, and 5 microliters (from a 100 uM stock) of a compound, e.g. diazapam, clozapine, with known metabolic properties is used as a positive control. Reactions are preincubated at 39° C. for 10 minutes. 71 microliters Starting Reaction Mixture is added to 5 of the 6 reaction wells and to the positive control well, 71 microliters 100 mM $MgCl_2$ is added to the sixth reaction well, which is used as a negative control. At each time point (0, 1, 3, 5, and 10 minutes) 75 microliters reaction is pipetted into a 96-well deep-well plate reaction well containing 75 microliters ice-cold acetonitrile. Samples are vortexed and centrifuged 10 minutes at 6000 rpm (Sorval T 6000D rotor). Supernatant, 75 microliters from each reaction well, is transferred to a 96-well plate containing 150 microliters internal standard per well. The remaining test compound is quantitated via LCMS. Compound concentration vs time is plotted and commercially available statistical software is used to extrapolate to the $t_{1/2}$ value of the test compound.

Preferred compounds of Formula I exhibit in vitro $t_{1/2}$ values of greater than 10 minutes and less than 4 hours. Most preferred compounds of Formula I exhibit in vitro $t_{1/2}$ values of between 30 minutes and 1 hour in human liver microsomes.

Example 36

MDCK Toxicity

Compounds causing acute cytotoxicity will decrease ATP production by Madin Darby canine kidney (MDCK) cells in the following assay.

MDCK cells, ATCC no. CCL-34 (American Type Culture Collection, Manassas, Va.) are maintained in sterile conditions following the instructions in the ATCC production information sheet. The PACKARD, (Meriden, Conn.) ATP-LITE-M Luminescent ATP detection kit, product no. 6016941, allows measurement ATP production in MDCK cells.

Prior to assay 1 microliter of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug or other compounds having known toxicity properties.

Confluent MDCK cells are trypsinized, harvested, and diluted to a concentration of $0.1 \times 10^6$ cells/ml with warm (37° C.) VITACELL Minimum Essential Medium Eagle (ATCC catalog # 30–2003). 100 microliters of cells in medium is pipetted into each of all but five wells of each 96-well plate. Warm medium without cells (100 ul) is pipetted in the remaining five wells of each plate. These wells, to which no cells are added, are used to determine the standard curve. The plates are then incubated at 37° C. under 95% $O_2$, 5% $CO_2$ for 2 hours with constant shaking. After incubation, 50 microliters of mammalian cell lysis solution is added per well, the wells are covered with PACKARD TOPSEAL stickers, and plates are shaken at approximately 700 rpm on a suitable shaker for 2 minutes.

During the incubation, PACKARD ATP LITE-M reagents are allowed to equilibrate to room temperature. Once equilibrated the lyophilized substrate solution is reconstituted in 5.5 ml of substrate buffer solution (from kit). Lyophilized ATP standard solution is reconstituted in deionized water to give a 10 mM stock. For the five control wells, 10 microliters of serially diluted PACKARD standard is added to each of the five standard curve control wells to yield a final concentration in each subsequent well of 200 nM, 100 nM, 50 nM, 25 nM, and 12.5 nM.

PACKARD substrate solution (50 ul) is added to all wells. Wells are covered with PACKARD TOPSEAL stickers, and plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter, e.g. PACKARD TOPCOUNT Microplate Scintillation and Luminescense Counter or TECAN SPECTRAFLUOR PLUS.

Luminescence values at each drug concentration are compared to the values computed from the standard curve for that concentration. Preferred test compounds exhibit luminescence values 80% or more of the standard, or preferably 90% or more of the standard, when a 10 micromolar (uM) concentration of the test compound is used. When a 100 micromolar concentration of the test compound is used, preferred test compounds exhibit luminescence values 50% or more of the standard, or more preferably 80% or more of the standard.

What is claimed is:

1. A compound of the Formula:

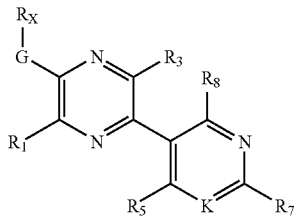

or a pharmaceutically acceptable salt thereof, wherein:

G is oxygen or NH;

$R_X$ is straight or branched chain $C_{1-8}$alkyl;

$R_1$ and $R_3$ are independently selected from hydrogen, cyano, $C_{1-4}$alkyl, halogen, $C_{1-2}$haloalkyl, $C_{1-2}$haloalkoxy, mono- and di-$C_{1-4}$alkylamino, $C_{1-4}$alkoxy, and $C_{1-4}$alkylthio;

$R_5$ is hydrogen, halogen, hydroxy, $C_{1-4}$alkyl, or $C_{1-4}$alkoxy;

K is N or CH;

$R_7$ is halogen, cyano, $C_{1-4}$alkyl, $C_{1-2}$ haloalkyl, $C_{1-2}$haloalkoxy, mono- and di-$C_{1-4}$alkylamino, $C_{1-2}$alkoxyC$_{1-4}$ alkyl, $C_{1-2}$alkoxycarbonyl, mono- and di-$C_{1-2}$alkylcarboxamido, —C(=O)NH$_2$, hydroxyC$_{1-2}$ alkyl, trifluoromethylsulfonyl, 2,2,2trifluoro-1-hydroxyethyl, or a 4–7 member heterocycloalkyl group containing 1 or 2 atoms independently chosen from N, O, and S;

$R_8$ is halogen, hydroxy, $C_{1-2}$alkyl, $C_{1-2}$alkoxy, or mono- and di-($C_{1-2}$alkyl)amino.

2. A compound or salt according to claim 1 wherein $R_1$ and $R_3$ are not hydrogen.

3. A compound or salt according to claim 1 wherein G is NH and $R_X$ is 1-ethyl propyl.

4. A compound or salt according to claim 3 wherein $R_1$ is cyano, methoxy, or methylthio and $R_3$ is methyl or ethyl.

5. A compound or salt according to claim 1 wherein G is oxygen and $R_X$ is 1-ethylpropyl, 1-isopropyl-2-methypropyl, 1-propylbutyl, or 1-ethylbutyl.

6. A compound or salt according to claim 5 wherein $R_3$ is halogen, $C_{1-2}$alkyl, or methylamino.

7. A compound or salt according to claim 5 wherein $R_1$ is halogen, methyl, methoxy, ethyl, ethoxy, or $C_{1-2}$alkylamino.

8. A compound or salt according to claim 5 wherein $R_1$ is methylamino.

9. A compound or salt according to claim 1 wherein, in a standard in vitro CRF receptor binding assay the compound exhibits a $K_i$ value for CRF receptors of less than or equal to 1 micromolar.

10. A compound or salt according to claim 1 wherein, in a standard in vitro CRF receptor binding assay the compound exhibits a $K_i$ value for CRF receptors of less than or equal to 100 nanomolar.

11. A compound or salt according to claims 1 wherein, in a standard in vitro CRF receptor binding assay, the compound exhibits a $K_i$ value for CRF receptors of less than or equal to 10 nanomolar.

12. A method for treating anxiety, or depression, comprising administering to a patient in need of such treatment a therapeutically effective amount of a compound or salt according to claim 1.

13. A pharmaceutical composition comprising a pharmaceutically acceptable carrier and a compound or salt of claim 1.

14. A pharmaceutical composition according to claim 13, wherein the composition is formulated as an injectable fluid, an aerosol, a cream, a gel, a tablet, a capsule, a syrup or a transdermal patch.

15. A package comprising a pharmaceutical composition of claim 13 in a container and further comprising indicia comprising at least one of:
- instructions for using the composition to treat a patient suffering from anxiety, or
- instructions for using the composition to treat a patient suffering from depression.

* * * * *